(12) United States Patent
Yarden et al.

(10) Patent No.: US 10,011,659 B2
(45) Date of Patent: Jul. 3, 2018

(54) COMPOSITIONS AND METHODS FOR TREATING CANCER RESISTANT TO A TYROSINE KINASE INHIBITOR (TKI)

(71) Applicant: Yeda Research and Development Co. Ltd., Rehovot (IL)

(72) Inventors: Yosef Yarden, Rehovot (IL); Maicol Mancini, Rehovot (IL); Nadège Gaborit, Rehovot (IL)

(73) Assignee: Yeda Research and Development Co. Ltd., Rehovot (IL)

(*) Notice: Subject to any disclaimer, the term of this patent is extended or adjusted under 35 U.S.C. 154(b) by 0 days.

(21) Appl. No.: 14/956,585

(22) Filed: Dec. 2, 2015

(65) Prior Publication Data

US 2016/0152712 A1    Jun. 2, 2016

Related U.S. Application Data

(63) Continuation-in-part of application No. PCT/IL2015/050916, filed on Sep. 8, 2015.

(60) Provisional application No. 62/047,150, filed on Sep. 8, 2014.

(51) Int. Cl.
| | | |
|---|---|---|
| C07K 16/28 | (2006.01) | |
| C07K 16/30 | (2006.01) | |
| C07K 16/32 | (2006.01) | |
| A61K 31/506 | (2006.01) | |
| A61K 31/517 | (2006.01) | |
| A61K 39/395 | (2006.01) | |
| A61N 5/10 | (2006.01) | |
| C07K 16/40 | (2006.01) | |
| A61K 39/00 | (2006.01) | |

(52) U.S. Cl.
CPC ........ *C07K 16/2863* (2013.01); *A61K 31/506* (2013.01); *A61K 31/517* (2013.01); *A61K 39/39558* (2013.01); *A61N 5/10* (2013.01); *C07K 16/30* (2013.01); *C07K 16/3023* (2013.01); *C07K 16/32* (2013.01); *C07K 16/40* (2013.01); *A61K 2039/507* (2013.01); *C07K 2317/24* (2013.01); *C07K 2317/565* (2013.01); *C07K 2317/73* (2013.01); *C07K 2317/76* (2013.01)

(58) Field of Classification Search
CPC ............ C07K 16/2863; C07K 2317/24; C07K 2317/565; A61K 39/39558
USPC ................ 424/133.1, 148.1, 173.1
See application file for complete search history.

(56) References Cited

U.S. PATENT DOCUMENTS

| 7,498,142 B2 | 3/2009 | Yarden et al. |
|---|---|---|
| 2010/0016296 A1 | 1/2010 | Singh et al. |
| 2013/0195870 A1 | 8/2013 | Jaiswal et al. |
| 2017/0306049 A1 | 10/2017 | Yarden et al. |

FOREIGN PATENT DOCUMENTS

| EP | 2727943 | 5/2014 |
|---|---|---|
| WO | WO 2011/022727 | 2/2011 |
| WO | WO 2011/060206 | 5/2011 |
| WO | WO 2011/136911 | 11/2011 |
| WO | WO 2011/144749 | 11/2011 |
| WO | WO 2012/031198 | 3/2012 |
| WO | WO 2012/059224 | 5/2012 |
| WO | WO 2012/059857 | 5/2012 |
| WO | WO 2012/059858 | 5/2012 |
| WO | WO 2012/125864 | 9/2012 |
| WO | WO 2012/156532 | 11/2012 |
| WO | WO 2012/156975 | 11/2012 |
| WO | WO 2013/048883 | 4/2013 |
| WO | WO 2013/164689 | 11/2013 |
| WO | WO 2016/038609 | 3/2016 |
| WO | WO 2016/038610 | 3/2016 |

OTHER PUBLICATIONS

Gaborit et al. Human Vaccines & Immunotherapeutics 2016, vol. 12, No. 3, 576-592.*
Gaborit et al. PNAS ( Jan. 20, 2015 ) vol. 112 ( No. 3 ): 839-844.*
Mancini et al. Science Signaling 8 (379), ra53. [doi: 10.1126/scisignal.aaa0725].*
Yarden et al. (Clin Cancer Res; 21(18); 4030-2 (2015).*
Huang et al. (Appl Microbiol Biotechnol (2010) 87:401-410).*
Voskoglou-Nomikos (Clin. Can. Res. 9:4227-4239 (2003)).*
Dennis (Nature 442:739-741 (2006)).*
Cespdes et al. (Clin. Transl. Oncol. 8(5):318-329 (2006)).*
Talmadge et al. (Am. J. Pathol 170(3):793-804 (2007)).*
Fujimori et al. (J. Nuc. Med. 31:1191-1198 (1990)).*
Beckman et al. (Can. 109:170-179 (2007)).*
Thurber et al. (Adv. Drug Deliv. Rev. 60:1421-1434 (2008)).*
Rudnick et al. (Can. Biotherp. & Radiopharm. 24: 155-162 (2009)).*
Clinicaltrials.gov website (search, pp. 1-3; Mar. 24, 2017).*
U.S. Appl. No. 15/508,112 (has not published as a pre-grant publication; discloses SEQ ID No. 5 and 6 for Clone NG33 as corresponding SEQ ID Nos. 19 and 20.*
Communication Relating to the Results of the Partial International Search dated Dec. 21, 2015 From the International Searching Authority Re. Application No. PCT/IL2015/050916.
Andersen et al. Examples, Claims.

(Continued)

*Primary Examiner* — Lynn A Bristol

(57) ABSTRACT

Methods of treating a subject having cancer exhibiting a resistance to a tyrosine kinase inhibitor (TKI) are provided. Accordingly, there is provided a method comprising administering to the subject a therapeutically effective amount of antibodies comprising an anti-EGFR antibody, an anti-HER2 antibody and an anti-HER3 antibody. Also provided are compositions and articles of manufacture for treating cancer resistance to a TKI. Also provided are methods of treating non-resistant tumors.

15 Claims, 14 Drawing Sheets
(11 of 14 Drawing Sheet(s) Filed in Color)

(56) References Cited

OTHER PUBLICATIONS

Huang et al. "Dual Targeting of EGFR and HER3 With MEHD7945A Overcomes Acquired Resistance to EGFR Inhibitors and Radiation", Cancer Research, XP055101487, 73(2): 824-833, Published Online Nov. 20, 2012. Abstract, Discussion.
Kruser et al. "Mechanisms of Resistance to HER Family Targeting Antibodies", Experimental Cell Research, XP009155414, 316(2010): 1083-1100, Published Online Jan. 11, 2010. p. 1093, r-h Col, Para 2.
Lazrek et al. "Anti-HER3 Domain 1 and 3 Antibodies Reduce Tumor Growth by Hindering HER2/HER3 Dimerization and AKT-Induced MDM2, XIAP, and Fox01 Phosphorylation", Neoplasia, XP002727137, 15(3): 335-347, Mar. 2013. Abstract, p. 343, r-h Col, Para 3, Fig 5.
Schoeberl et al "An ErbB3 Antibody, MM-1231, Is Active in Cancers With Ligand-Dependent Activation", Cancer Research, XP002581703, 70(6): 2485-2494, Mar. 15, 2010. Abstract, Discussion, Last Para.
International Search Report and the Written Opinion dated Jan. 18, 2016 From the International Searching Authority Re. Application No. PCT/IL2015/050915.
International Search Report and the Written Opinion dated Feb. 26, 2016 From the International Searching Authority Re. Application No. PCT/IL2015/050916.
European Search Report and the European Search Opinion dated May 2, 2017 From the European Patent Office Re. Application No. 16201602.6. (9 Pages).
International Preliminary Report on Patentability dated Mar. 23, 2017 From the International Bureau of WIPO Re. Application No. PCT/IL2015/050915. (13 Pages).
International Preliminary Report on Patentability dated Mar. 23, 2017 From the International Bureau of WIPO Re. Application No. PCT/IL2015/050916. (15 Pages).
Bean et al. "MET Amplification Occurs With or Without T790M Mutations in EGFR Mutant Lung Tumors With Acquired Resistance to Gefinitib or Erlotinib", Proc. Natl. Acad. Sci. USA, PNAS, 104(52): 20932-20937, Dec. 26, 2007.
Chen et al. "An Immunological Approach Reveals Biological Differences Between the Two NDF/Heregulin Receptors, ErbB-3 and ErbB-4", The Journal of Biological Chemistry, 271(13): 7620-2629, Mar. 29, 1996.
Citri et al. "EGF-ERBB Singalling: Towards the Systems Level", Nature Reviews Molecular Cell Biology, 7: 505-516, Jul. 2006.
Engelman et al. "MET Amplification Leads to Gefinitib Resistance in Lung Cancer by Activating ERBB3 Signaling", Science, 316: 1039-1043, May 18, 2007.
Hirsch et al. "Epidermal Growth Factor Receptor Inhibition in Lung Cancer. Status 2012", Journal of Thoracic Oncology, 8(3): 373-384, Mar. 2013.
Jiang et al. "Advances in Targeting HER3 as an Anticancer Therapy", Chemotherapy Research and Practice, 2012(Art. 817304): 1-9, 2012.
Ma et al. "Targeting of ErbB3 Receptor to Overcome Resistance in Cancer Treatment", Molecular Cancer, 13(105): 1-9, 2014.
Mok et al. "Gefitinib or Carboplatin-Paclitaxel in Pulmonary Adenocarcinoma", The New England Journal of Medicine, 361(10): 947-957, Sep. 3, 2009.
Ohashi et al. "Epidermal Growth Factor Receptor Tyrosine Kinase Inhibitor-Resistant Disease", Journal of Clinical Oncology, 31(8): 1070-1080, Mar. 10, 2013.
Pirker et al. "Cetuximab Plus Chemotherapy in Patients With Advanced Non-Small-Cell Lung Cancer (FLEX): An Open-Label Randomised Phase III Trial", The Lancet, 373: 1525-1531, May 2, 2009.
Rexer et al. "Human Breast Cancer Cells Harboring a Gatekeeper T798M Mutation in HER2 Overexpress EGFR Ligands and Are Sensitive to Dual Inhibition of EGFR and HER2", Clinical Cancer Research, 19(19): 5390-5401, Oct. 1, 2013. Abstract.
Rosell et al. "Screening for Epidermal Growth Factor Receptor Mutations in Lung Cancer", The New England Journal of Medicine, 361(10): 958-967, Sep. 3, 2009.
Sarup et al. "Human Epidermal Growth Factor Receptor (HER-1:HER-3) Fc-Mediated Heterodimer Has Broad Antiproliferative Activity In Vitro and in Human Tumor Xenografts", Molecular Cancer Therapeutics, 7(10): 3223-3236, Oct. 2008.
Sergina et al. "Escape From HER Family Tyrosine Kinase Inhibitor Therapy by the Kinase Inactive HER3", Nature, 445(7126): 437-441, Jan. 25, 2007.
Takezawa et al. "HER2 Amplification: A Potential Mechanism of Acquired Resistance to EGFR Inhibition in EGFR-Mutant Lung Cancers That Lack the Second-Site EGFR[T790M] Mutation", Cancer Discovery, 2(10): 922-933, Published OnlineFirst Sep. 5, 2012.
Wang et al. "Mechanisms of Resistance to ErbB-Targeted Cancer Therapeutics", The Journal of Clinical Investigation, 118(7): 2389-2392, Jul. 2008.
Wheeler et al. "Mechanisms of Acquired Resistance to Cetuximab: Role of HER (ErbB) Family Members", Oncogene, 27: 3944-3956, Published Online Feb. 25, 2008.
Communication Pursuant to Article 94(3) EPC dated Feb. 16, 2018 From the European Patent Office Re. Application No. 15781155.5. (8 Pages).

* cited by examiner

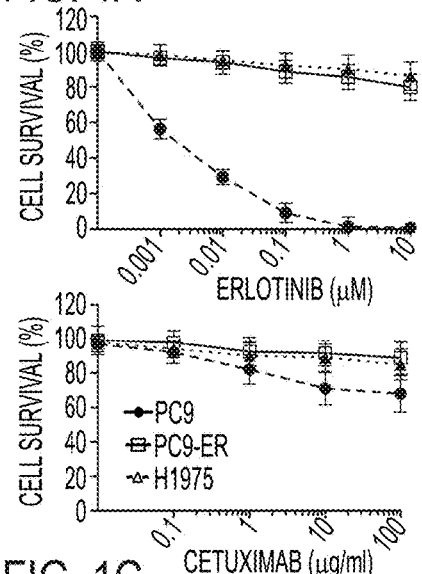
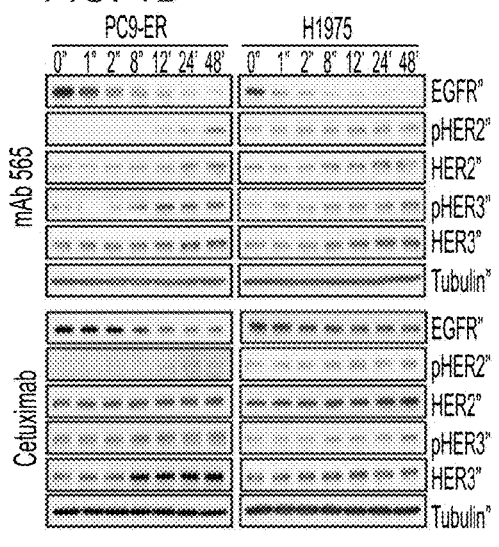
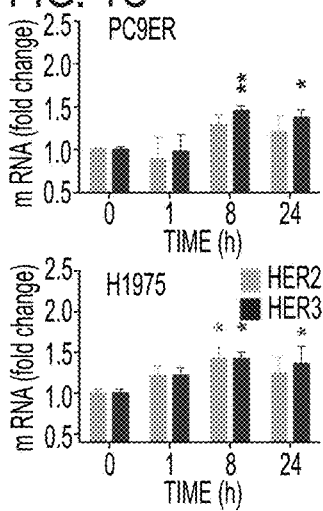
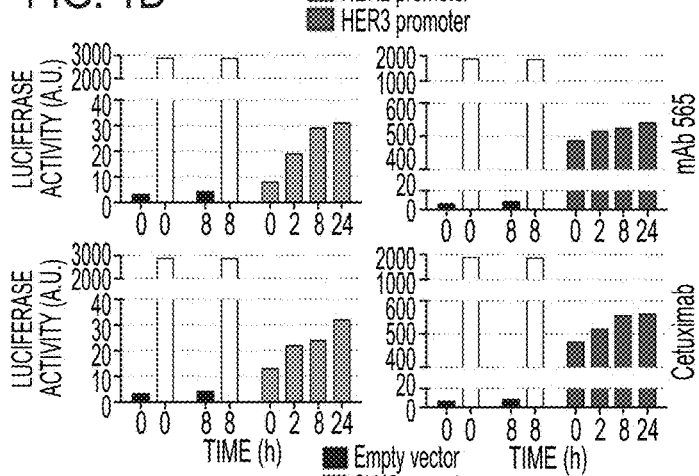
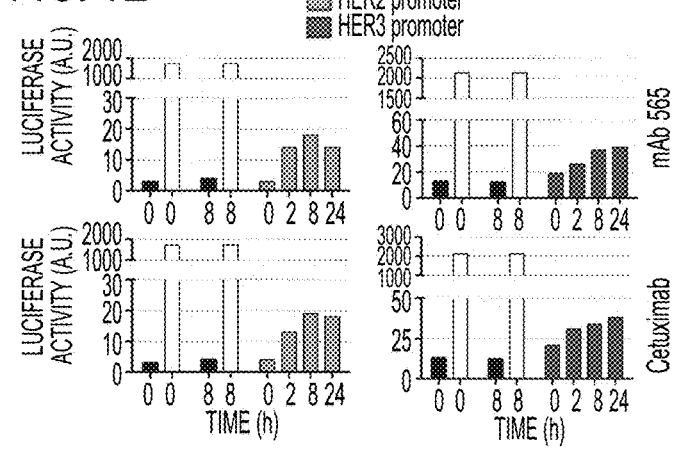

FIG. 22A
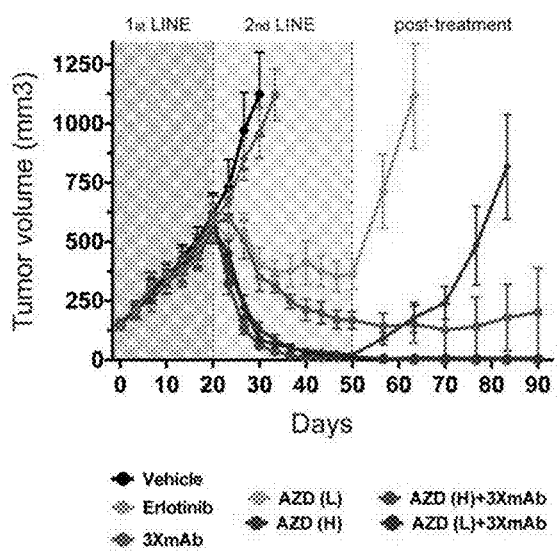
FIG. 22B
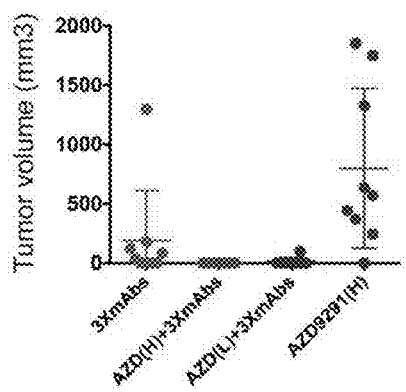
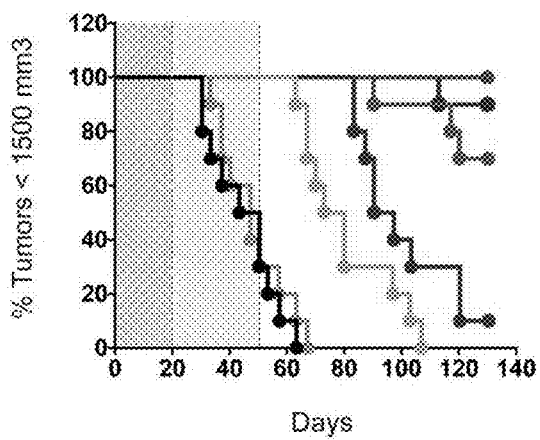
FIG. 22C

COMPOSITIONS AND METHODS FOR TREATING CANCER RESISTANT TO A TYROSINE KINASE INHIBITOR (TKI)

RELATED APPLICATIONS

This application is a Continuation In Part of PCT Patent Application No. PCT/IL2015/050916 having International filing date of Sep. 8, 2015, which claims the benefit of priority under 35 USC § 119(e) of U.S. Provisional Patent Application No. 62/047,150 filed on Sep. 8, 2014. The contents of the above applications are all incorporated by reference as if fully set forth herein in their entirety.

The work leading to this invention has received funding from the European Community's Seventh Framework Program (FP72007-2011) under grant agreement 259770 LUNGTARGET.

SEQUENCE LISTING STATEMENT

The ASCII file, entitled 64686SequenceListing.txt, created on Dec. 2, 2015, comprising 13,129 bytes, submitted concurrently with the filing of this application is incorporated herein by reference.

FIELD AND BACKGROUND OF THE INVENTION

The present invention, in some embodiments thereof, relates to compositions and methods for treating cancer resistant to a tyrosine kinase inhibitor.

The ErbB/HER family of receptor tyrosine kinases, which includes epidermal growth factor receptor (EGFR, also termed ErbB-1, HER1), HER2 (ErbB-2), HER3 (ErbB-3) and HER4 (ErbB-4) is widely known and researched. The ErbB/HER family members and their multiple ligand molecules form a layered signaling network, which is implicated in several human cancers. ErbB activation leads to downstream stimulation of several signaling cascades, including MAPK and PI(3)K/Akt that influence cell proliferation, angiogenesis, invasion and metastasis [Citri and Yarden Nat Rev Mol Cell Biol. (2006) 7(7):505-16]. Because of their oncogenic potential and accessibility, ErbB/HER proteins have emerged as attractive targets for pharmaceutical interventions. Consistently, strategies able to interfere with ErbB functions, such as monoclonal antibodies (mAbs) and tyrosine kinase inhibitors (TKIs), have yielded in the last decade several oncology drugs which have shown great success in treating many patients with lung, breast, colon and other types of cancer.

For example, the anti-EGFR mAbs cetuximab (ERBITUX®) and the anti-HER2 mAb trastuzumab (HERCEPTIN®) have been developed and approved for the treatment of human cancers.

TKIs are small-molecule therapeutics designed to bind to the ATP-binding site of the tyrosine kinase domain, preempting the binding of ATP and directly inhibiting the kinase activity of ErbB receptors such as EGFR or HER2. For example, a number of TKIs for EGFR have been developed; including gefitinib (IRESSA®) and erlotinib (TARCEVA®), both gained FDA approval in oncology treatment. In addition, TKIs that simultaneously target multiple ErbB species, such as AZD9291, CI-1033 (PD183805) and lapatinib (GW572016/TYKERB®), have also been developed.

However, while many cancer patients were found to be sensitive to ErbB-targeted therapy, many other patients are resistant to treatment, and even among the initially responsive patients a large percentage experience tumor recurrence and become refractory to therapy. Thus for example, despite initial dramatic response of non-small cell lung cancer (NSCLC) patients to TKIs, all patients acquire resistance within approximately one year (6, 7). The most common (>50%) mechanism of this acquired resistance involves a specific second site mutation in the EGFR kinase domain. A threonine-to-methionine substitution at position 790 creates a steric hindrance that limits the binding of the TKIs, while preserving the kinase activity. [Wang and Greene J Clin Invest. (2008) 118(7): 2389-2392]. Amplification of the gene encoding another receptor tyrosine kinase, MET, occurs in 5-10% of cases of acquired resistance (11, 12).

To overcome TKI resistance, several second and third generation TKIs are being developed (13,14). Alternatively, a clinical trial combining cetuximab and chemotherapy (cis-platin/vinorelbin) demonstrated a relatively small, but significant increase in patient survival (15).

The cooperative role of the ErbB family members has furthermore been supported by in-vitro and in-vivo studies demonstrating that resistance to both mAbs and TKIs targeting a specific ErbB is associated with dysregulation and increased activity of other ErbB family members (see e.g. Wheeler et al. Oncogene. Jun. 26, 2008; 27(28): 3944-3956; Takezawa et al. Cancer discovery (2012) 2, 922-933 and Sergina et al. Nature (2007) 445, 437-441]. Thus, methods for overcoming resistance to an ErbB pathway inhibitor using combinations of ErbB family inhibitors were also described in the art for e.g. breast, lung, head and neck cancers. For example, International Application Publication No. WO 2012/125864 discloses the use of an ErbB-3 inhibitor and a second ErbB pathway inhibitor, the ErbB-3 inhibitor may be a bi-specific antibody which also targets ErbB-2 in order to overcome acquired resistance to the small molecule EGFR inhibitor gefitinib.

Other art documents related to antibody combinations in the treatment of cancer resistance to an ErbB-targeted therapy include:

US Patent Application Publication Number: 20100016296;

International Application Publication Numbers: WO 2012/059857;

Sarup et al. [Mol. Canc. Ther. (2008) 7(10):3223-3236];
Ma et al. [Molecular Cancer 2014, 13:105];
Jiang et al. [Chemother Res Pract. 2012; 2012:817304];
Wheeler et al. [Oncogene. (2008) 27(28): 3944-3956];
Rexer et al. Clin Cancer Res. (2013) 19(19):5390-401]; and
Takezawa et al. [*Cancer discovery* (2012) 2, 922-933].

SUMMARY OF THE INVENTION

According to an aspect of some embodiments of the present invention there is provided a method of treating a subject having cancer exhibiting a resistance to a tyrosine kinase inhibitor (TKI), wherein the TKI is directed to an ErbB family member and wherein cells of the cancer express the ErbB family member, the method comprising administering to the subject a therapeutically effective amount of antibodies comprising an anti-EGFR antibody, an anti-HER2 antibody and an anti-HER3 antibody, wherein:

(i) the anti-EGFR antibody comprises an antigen recognition domain having complementarity determining region (CDR) amino acid sequences as set forth in: SEQ ID NOs: 15 (CDR1), 16 (CDR2) and 17 (CDR3) (sequentially arranged from N to C on a light chain of the polypeptide) and 18 (CDR1), 19 (CDR2) and 20 (CDR3) (sequentially arranged from N to C on a heavy chain of the polypeptide) (Clone 565, CNCM-4262);

(ii) the anti-HER2 antibody comprises an antigen recognition domain having complementarity determining region (CDR) amino acid sequences as set forth in: SEQ ID NOs: 21 (CDR1), 22 (CDR2) and 23 (CDR3) (sequentially arranged from N to C on a light chain of the polypeptide) and 24 (CDR1), 25 (CDR2) and 26 (CDR3) (sequentially arranged from N to C on a heavy chain of the polypeptide) (Clone N12, CNCM-I-4112);

(iii) the anti-HER3 antibody comprises an antigen recognition domain having complementarity determining region (CDR) amino acid sequences as set forth in: SEQ ID NOs: 27 (CDR1), 28 (CDR2) and 29 (CDR3) (sequentially arranged from N to C on a light chain of the polypeptide) and 30 (CDR1), 31 (CDR2) and 32 (CDR3) (sequentially arranged from N to C on a heavy chain of the polypeptide) (Clone NG33);

(iv) the anti-EGFR antibody comprises an antigen recognition domain having complementarity determining region (CDR) amino acid sequences as set forth in: SEQ ID NOs: 15 (CDR1), 16 (CDR2) and 17 (CDR3) (sequentially arranged from N to C on a light chain of the polypeptide) and 18 (CDR1), 19 (CDR2) and 20 (CDR3) (sequentially arranged from N to C on a heavy chain of the polypeptide) (Clone 565, CNCM-4262) and the anti-HER2 antibody comprises an antigen recognition domain having complementarity determining region (CDR) amino acid sequences as set forth in: SEQ ID NOs: 21 (CDR1), 22 (CDR2) and 23 (CDR3) (sequentially arranged from N to C on a light chain of the polypeptide) and 24 (CDR1), 25 (CDR2) and 26 (CDR3) (sequentially arranged from N to C on a heavy chain of the polypeptide) (Clone N12, CNCM-I-4112);

(v) the anti-EGFR antibody comprises an antigen recognition domain having complementarity determining region (CDR) amino acid sequences as set forth in: SEQ ID NOs: 15 (CDR1), 16 (CDR2) and 17 (CDR3) (sequentially arranged from N to C on a light chain of the polypeptide) and 18 (CDR1), 19 (CDR2) and 20 (CDR3) (sequentially arranged from N to C on a heavy chain of the polypeptide) (Clone 565, CNCM-4262) and the anti-HER3 antibody comprises an antigen recognition domain having complementarity determining region (CDR) amino acid sequences as set forth in: SEQ ID NOs: 27 (CDR1), 28 (CDR2) and 29 (CDR3) (sequentially arranged from N to C on a light chain of the polypeptide) and 30 (CDR1), 31 (CDR2) and 32 (CDR3) (sequentially arranged from N to C on a heavy chain of the polypeptide) (Clone NG33);

(vi) the anti-HER2 antibody comprises an antigen recognition domain having complementarity determining region (CDR) amino acid sequences as set forth in: SEQ ID NOs: 21 (CDR1), 22 (CDR2) and 23 (CDR3) (sequentially arranged from N to C on a light chain of the polypeptide) and 24 (CDR1), 25 (CDR2) and 26 (CDR3) (sequentially arranged from N to C on a heavy chain of the polypeptide) (Clone N12, CNCM-I-4112); and the anti-HER3 antibody comprises an antigen recognition domain having complementarity determining region (CDR) amino acid sequences as set forth in: SEQ ID NOs: 27 (CDR1), 28 (CDR2) and 29 (CDR3) (sequentially arranged from N to C on a light chain of the polypeptide) and 30 (CDR1), 31 (CDR2) and 32 (CDR3) (sequentially arranged from N to C on a heavy chain of the polypeptide) (Clone NG33);

(vii) the anti-EGFR antibody comprises an antigen recognition domain having complementarity determining region (CDR) amino acid sequences as set forth in: SEQ ID NOs: 15 (CDR1), 16 (CDR2) and 17 (CDR3) (sequentially arranged from N to C on a light chain of the polypeptide) and 18 (CDR1), 19 (CDR2) and 20 (CDR3) (sequentially arranged from N to C on a heavy chain of the polypeptide) (Clone 565, CNCM-4262), the anti-HER2 antibody comprises an antigen recognition domain having complementarity determining region (CDR) amino acid sequences as set forth in: SEQ ID NOs: 21 (CDR1), 22 (CDR2) and 23 (CDR3) (sequentially arranged from N to C on a light chain of the polypeptide) and 24 (CDR1), 25 (CDR2) and 26 (CDR3) (sequentially arranged from N to C on a heavy chain of the polypeptide) (Clone N12, CNCM-I-4112); and the anti-HER3 antibody comprises an antigen recognition domain having complementarity determining region (CDR) amino acid sequences as set forth in: SEQ ID NOs: 27 (CDR1), 28 (CDR2) and 29 (CDR3) (sequentially arranged from N to C on a light chain of the polypeptide) and 30 (CDR1), 31 (CDR2) and 32 (CDR3) (sequentially arranged from N to C on a heavy chain of the polypeptide) (Clone NG33);

(vii) the anti-EGFR antibody comprises an antigen recognition domain having complementarity determining region (CDR) amino acid sequences as set forth in: SEQ ID NOs: 15 (CDR1), 16 (CDR2) and 17 (CDR3) (sequentially arranged from N to C on a light chain of the polypeptide) and 18 (CDR1), 19 (CDR2) and 20 (CDR3) (sequentially arranged from N to C on a heavy chain of the polypeptide) (Clone 565, CNCM-4262), the anti-HER2 antibody comprises an antigen recognition domain having complementarity determining region (CDR) amino acid sequences as set forth in: SEQ ID NOs: 21 (CDR1), 22 (CDR2) and 23 (CDR3) (sequentially arranged from N to C on a light chain of the polypeptide) and 24 (CDR1), 25 (CDR2) and 26 (CDR3) (sequentially arranged from N to C on a heavy chain of the polypeptide) (Clone N12, CNCM-I-4112); and the anti-HER3 antibody comprises an antigen recognition domain having complementarity determining region (CDR) amino acid sequences as set forth in: SEQ ID NOs: 27 (CDR1), 28 (CDR2) and 29 (CDR3) (sequentially arranged from N to C on a light chain of the polypeptide) and 30 (CDR1), 31 (CDR2) and 32 (CDR3) (sequentially arranged from N to C on a heavy chain of the polypeptide) (Clone NG33);

(viii) the anti-EGFR antibody comprises cetuximab; and the anti-HER3 antibody comprises an antigen recognition domain having complementarity determining region (CDR) amino acid sequences as set forth in: SEQ ID NOs: 27 (CDR1), 28 (CDR2) and 29 (CDR3) (sequentially arranged from N to C on a light chain of the polypeptide) and 30 (CDR1), 31 (CDR2) and 32 (CDR3) (sequentially arranged from N to C on a heavy chain of the polypeptide) (Clone NG33);

(ix) the anti-HER2 antibody comprises trastuzumab; and the anti-HER3 antibody comprises an antigen recognition domain having complementarity determining region (CDR) amino acid sequences as set forth in: SEQ ID NOs: 27 (CDR1), 28 (CDR2) and 29 (CDR3) (sequentially arranged from N to C on a light chain of the polypeptide) and 30 (CDR1), 31 (CDR2) and 32 (CDR3) (sequentially arranged from N to C on a heavy chain of the polypeptide) (Clone NG33); and/or (x) the anti-EGFR antibody comprises cetuximab, the anti-HER2 antibody comprises trastuzumab; and the anti-HER3 antibody comprises an antigen recognition domain having complementarity determining region (CDR) amino acid sequences as set forth in: SEQ ID NOs: 27 (CDR1), 28 (CDR2) and 29 (CDR3) (sequentially arranged from N to C on a light chain of the polypeptide) and 30 (CDR1), 31 (CDR2) and 32 (CDR3) (sequentially arranged from N to C on a heavy chain of the polypeptide) (Clone NG33), thereby treating the resistance to a tyrosine kinase inhibitor (TKI) of an ErbB family member in a subject.

According to an aspect of some embodiments of the present invention there is provided a method of treating a subject having cancer, the method comprising administering to the subject a therapeutically effective amount of a tyrosine kinase inhibitor (TKI) and antibodies comprising an anti-EGFR antibody, an anti-HER2 antibody and an anti-HER3 antibody, wherein the TKI is directed to an ErbB family member and wherein cells of the cancer express the ErbB family member and wherein:

(i) the anti-EGFR antibody comprises an antigen recognition domain having complementarity determining region (CDR) amino acid sequences as set forth in: SEQ ID NOs: 15 (CDR1), 16 (CDR2) and 17 (CDR3) (sequentially arranged from N to C on a light chain of the polypeptide) and 18 (CDR1), 19 (CDR2) and 20 (CDR3) (sequentially arranged from N to C on a heavy chain of the polypeptide) (Clone 565, CNCM-4262);

(ii) the anti-HER2 antibody comprises an antigen recognition domain having complementarity determining region (CDR) amino acid sequences as set forth in: SEQ ID NOs: 21 (CDR1), 22 (CDR2) and 23 (CDR3) (sequentially arranged from N to C on a light chain of the polypeptide) and 24 (CDR1), 25 (CDR2) and 26 (CDR3) (sequentially arranged from N to C on a heavy chain of the polypeptide) (Clone N12, CNCM-I-4112);

(iii) the anti-HER3 antibody comprises an antigen recognition domain having complementarity determining region (CDR) amino acid sequences as set forth in: SEQ ID NOs: 27 (CDR1), 28 (CDR2) and 29 (CDR3) (sequentially arranged from N to C on a light chain of the polypeptide) and 30 (CDR1), 31 (CDR2) and 32 (CDR3) (sequentially arranged from N to C on a heavy chain of the polypeptide) (Clone NG33);

(iv) the anti-EGFR antibody comprises an antigen recognition domain having complementarity determining region (CDR) amino acid sequences as set forth in: SEQ ID NOs: 15 (CDR1), 16 (CDR2) and 17 (CDR3) (sequentially arranged from N to C on a light chain of the polypeptide) and 18 (CDR1), 19 (CDR2) and 20 (CDR3) (sequentially arranged from N to C on a heavy chain of the polypeptide) (Clone 565, CNCM-4262) and the anti-HER2 antibody comprises an antigen recognition domain having complementarity determining region (CDR) amino acid sequences as set forth in: SEQ ID NOs: 21 (CDR1), 22 (CDR2) and 23 (CDR3) (sequentially arranged from N to C on a light chain of the polypeptide) and 24 (CDR1), 25 (CDR2) and 26 (CDR3) (sequentially arranged from N to C on a heavy chain of the polypeptide) (Clone N12, CNCM-I-4112);

(v) the anti-EGFR antibody comprises an antigen recognition domain having complementarity determining region (CDR) amino acid sequences as set forth in: SEQ ID NOs: 15 (CDR1), 16 (CDR2) and 17 (CDR3) (sequentially arranged from N to C on a light chain of the polypeptide) and 18 (CDR1), 19 (CDR2) and 20 (CDR3) (sequentially arranged from N to C on a heavy chain of the polypeptide) (Clone 565, CNCM-4262) and the anti-HER3 antibody comprises an antigen recognition domain having complementarity determining region (CDR) amino acid sequences as set forth in: SEQ ID NOs: 27 (CDR1), 28 (CDR2) and 29 (CDR3) (sequentially arranged from N to C on a light chain of the polypeptide) and 30 (CDR1), 31 (CDR2) and 32 (CDR3) (sequentially arranged from N to C on a heavy chain of the polypeptide) (Clone NG33);

(vi) the anti-HER2 antibody comprises an antigen recognition domain having complementarity determining region (CDR) amino acid sequences as set forth in: SEQ ID NOs: 21 (CDR1), 22 (CDR2) and 23 (CDR3) (sequentially arranged from N to C on a light chain of the polypeptide) and 24 (CDR1), 25 (CDR2) and 26 (CDR3) (sequentially arranged from N to C on a heavy chain of the polypeptide) (Clone N12, CNCM-I-4112); and the anti-HER3 antibody comprises an antigen recognition domain having complementarity determining region (CDR) amino acid sequences as set forth in: SEQ ID NOs: 27 (CDR1), 28 (CDR2) and 29 (CDR3) (sequentially arranged from N to C on a light chain of the polypeptide) and 30 (CDR1), 31 (CDR2) and 32 (CDR3) (sequentially arranged from N to C on a heavy chain of the polypeptide) (Clone NG33);

(vii) the anti-EGFR antibody comprises an antigen recognition domain having complementarity determining region (CDR) amino acid sequences as set forth in: SEQ ID NOs: 15 (CDR1), 16 (CDR2) and 17 (CDR3) (sequentially arranged from N to C on a light chain of the polypeptide) and 18 (CDR1), 19 (CDR2) and 20 (CDR3) (sequentially arranged from N to C on a heavy chain of the polypeptide) (Clone 565, CNCM-4262), the anti-HER2 antibody comprises an antigen recognition domain having complementarity determining region (CDR) amino acid sequences as set forth in: SEQ ID NOs: 21 (CDR1), 22 (CDR2) and 23 (CDR3) (sequentially arranged from N to C on a light chain of the polypeptide) and 24 (CDR1), 25 (CDR2) and 26 (CDR3) (sequentially arranged from N to C on a heavy chain of the polypeptide) (Clone N12, CNCM-I-4112); and the anti-HER3 antibody comprises an antigen recognition domain having complementarity determining region (CDR) amino acid sequences as set forth in: SEQ ID NOs: 27 (CDR1), 28 (CDR2) and 29 (CDR3) (sequentially arranged from N to C on a light chain of the polypeptide) and 30 (CDR1), 31 (CDR2) and 32 (CDR3) (sequentially arranged from N to C on a heavy chain of the polypeptide) (Clone NG33);

(viii) the anti-EGFR antibody comprises cetuximab; and the anti-HER3 antibody comprises an antigen recognition domain having complementarity determining region (CDR) amino acid sequences as set forth in: SEQ ID NOs: 27 (CDR1), 28 (CDR2) and 29 (CDR3) (sequentially arranged from N to C on a light chain of the polypeptide) and 30 (CDR1), 31 (CDR2) and 32 (CDR3) (sequentially arranged from N to C on a heavy chain of the polypeptide) (Clone NG33);

(ix) the anti-HER2 antibody comprises trastuzumab; and the anti-HER3 antibody comprises an antigen recognition domain having complementarity determining region (CDR) amino acid sequences as set forth in: SEQ ID NOs: 27 (CDR1), 28 (CDR2) and 29 (CDR3) (sequentially arranged from N to C on a light chain of the polypeptide) and 30 (CDR1), 31 (CDR2) and 32 (CDR3) (sequentially arranged from N to C on a heavy chain of the polypeptide) (Clone NG33); and/or (x) the anti-EGFR antibody comprises cetuximab, the anti-HER2 antibody comprises trastuzumab; and the anti-HER3 antibody comprises an antigen recognition domain having complementarity determining region (CDR) amino acid sequences as set forth in: SEQ ID NOs: 27 (CDR1), 28 (CDR2) and 29 (CDR3) (sequentially arranged from N to C on a light chain of the polypeptide) and 30 (CDR1), 31 (CDR2) and 32 (CDR3) (sequentially arranged from N to C on a heavy chain of the polypeptide) (Clone NG33), thereby treating the cancer.

According to an aspect of some embodiments of the present invention there is provided a tyrosine kinase inhibitor (TKI) and antibodies comprising an anti-EGFR antibody, an anti-HER2 antibody and an anti-HER3 antibody, wherein the), wherein the TKI is directed to an ErbB family member and wherein cells of the cancer express the ErbB family member and wherein:

(i) the anti-EGFR antibody comprises an antigen recognition domain having complementarity determining region (CDR) amino acid sequences as set forth in: SEQ ID NOs: 15 (CDR1), 16 (CDR2) and 17 (CDR3) (sequentially arranged from N to C on a light chain of the polypeptide) and 18 (CDR1), 19 (CDR2) and 20 (CDR3) (sequentially arranged from N to C on a heavy chain of the polypeptide) (Clone 565, CNCM-4262);

(ii) the anti-HER2 antibody comprises an antigen recognition domain having complementarity determining region (CDR) amino acid sequences as set forth in: SEQ ID NOs: 21 (CDR1), 22 (CDR2) and 23 (CDR3) (sequentially arranged from N to C on a light chain of the polypeptide) and 24 (CDR1), 25 (CDR2) and 26 (CDR3) (sequentially arranged from N to C on a heavy chain of the polypeptide) (Clone N12, CNCM-I-4112);

(iii) the anti-HER3 antibody comprises an antigen recognition domain having complementarity determining region (CDR) amino acid sequences as set forth in: SEQ ID NOs: 27 (CDR1), 28 (CDR2) and 29 (CDR3) (sequentially arranged from N to C on a light chain of the polypeptide) and 30 (CDR1), 31 (CDR2) and 32 (CDR3) (sequentially arranged from N to C on a heavy chain of the polypeptide) (Clone NG33);

(iv) the anti-EGFR antibody comprises an antigen recognition domain having complementarity determining region (CDR) amino acid sequences as set forth in: SEQ ID NOs: 15 (CDR1), 16 (CDR2) and 17 (CDR3) (sequentially arranged from N to C on a light chain of the polypeptide) and 18 (CDR1), 19 (CDR2) and 20 (CDR3) (sequentially arranged from N to C on a heavy chain of the polypeptide) (Clone 565, CNCM-4262) and the anti-HER2 antibody comprises an antigen recognition domain having complementarity determining region (CDR) amino acid sequences as set forth in: SEQ ID NOs: 21 (CDR1), 22 (CDR2) and 23 (CDR3) (sequentially arranged from N to C on a light chain of the polypeptide) and 24 (CDR1), 25 (CDR2) and 26 (CDR3) (sequentially arranged from N to C on a heavy chain of the polypeptide) (Clone N12, CNCM-I-4112);

(v) the anti-EGFR antibody comprises an antigen recognition domain having complementarity determining region (CDR) amino acid sequences as set forth in: SEQ ID NOs: 15 (CDR1), 16 (CDR2) and 17 (CDR3) (sequentially arranged from N to C on a light chain of the polypeptide) and 18 (CDR1), 19 (CDR2) and 20 (CDR3) (sequentially arranged from N to C on a heavy chain of the polypeptide) (Clone 565, CNCM-4262) and the anti-HER3 antibody comprises an antigen recognition domain having complementarity determining region (CDR) amino acid sequences as set forth in: SEQ ID NOs: 27 (CDR1), 28 (CDR2) and 29 (CDR3) (sequentially arranged from N to C on a light chain of the polypeptide) and 30 (CDR1), 31 (CDR2) and 32 (CDR3) (sequentially arranged from N to C on a heavy chain of the polypeptide) (Clone NG33);

(vi) the anti-HER2 antibody comprises an antigen recognition domain having complementarity determining region (CDR) amino acid sequences as set forth in: SEQ ID NOs: 21 (CDR1), 22 (CDR2) and 23 (CDR3) (sequentially arranged from N to C on a light chain of the polypeptide) and 24 (CDR1), 25 (CDR2) and 26 (CDR3) (sequentially arranged from N to C on a heavy chain of the polypeptide) (Clone N12, CNCM-I-4112); and the anti-HER3 antibody comprises an antigen recognition domain having complementarity determining region (CDR) amino acid sequences as set forth in: SEQ ID NOs: 27 (CDR1), 28 (CDR2) and 29 (CDR3) (sequentially arranged from N to C on a light chain of the polypeptide) and 30 (CDR1), 31 (CDR2) and 32 (CDR3) (sequentially arranged from N to C on a heavy chain of the polypeptide) (Clone NG33);

(vii) the anti-EGFR antibody comprises an antigen recognition domain having complementarity determining region (CDR) amino acid sequences as set forth in: SEQ ID NOs: 15 (CDR1), 16 (CDR2) and 17 (CDR3) (sequentially arranged from N to C on a light chain of the polypeptide) and 18 (CDR1), 19 (CDR2) and 20 (CDR3) (sequentially arranged from N to C on a heavy chain of the polypeptide) (Clone 565, CNCM-4262), the anti-HER2 antibody comprises an antigen recognition domain having complementarity determining region (CDR) amino acid sequences as set forth in: SEQ ID NOs: 21 (CDR1), 22 (CDR2) and 23 (CDR3) (sequentially arranged from N to C on a light chain of the polypeptide) and 24 (CDR1), 25 (CDR2) and 26 (CDR3) (sequentially arranged from N to C on a heavy chain of the polypeptide) (Clone N12, CNCM-I-4112); and the anti-HER3 antibody comprises an antigen recognition domain having complementarity determining region (CDR) amino acid sequences as set forth in: SEQ ID NOs: 27 (CDR1), 28 (CDR2) and 29 (CDR3) (sequentially arranged from N to C on a light chain of the polypeptide) and 30 (CDR1), 31 (CDR2) and 32 (CDR3) (sequentially arranged from N to C on a heavy chain of the polypeptide) (Clone NG33);

(viii) the anti-EGFR antibody comprises cetuximab; and the anti-HER3 antibody comprises an antigen recognition domain having complementarity determining region (CDR) amino acid sequences as set forth in: SEQ ID NOs: 27 (CDR1), 28 (CDR2) and 29 (CDR3) (sequentially arranged from N to C on a light chain of the polypeptide) and 30 (CDR1), 31 (CDR2) and 32 (CDR3) (sequentially arranged from N to C on a heavy chain of the polypeptide) (Clone NG33);

(ix) the anti-HER2 antibody comprises trastuzumab; and the anti-HER3 antibody comprises an antigen recognition domain having complementarity determining region (CDR) amino acid sequences as set forth in: SEQ ID NOs: 27 (CDR1), 28 (CDR2) and 29 (CDR3) (sequentially arranged from N to C on a light chain of the polypeptide) and 30 (CDR1), 31 (CDR2) and 32 (CDR3) (sequentially arranged from N to C on a heavy chain of the polypeptide) (Clone NG33); and/or (x) the anti-EGFR antibody comprises cetuximab, the anti-HER2 antibody comprises trastuzumab; and the anti-HER3 antibody comprises an antigen recognition domain having complementarity determining region (CDR) amino acid sequences as set forth in: SEQ ID NOs: 27 (CDR1), 28 (CDR2) and 29 (CDR3) (sequentially arranged from N to C on a light chain of the polypeptide) and 30 (CDR1), 31 (CDR2) and 32 (CDR3) (sequentially arranged from N to C on a heavy chain of the polypeptide) (Clone NG33) for treating the cancer.

According to an aspect of some embodiments of the present invention there is provided an article of manufacture identified for treating cancer resistance to a tyrosine kinase inhibitor (TKI) comprising a packaging material packaging in separate containers an anti-EGFR antibody, an anti-HER2 antibody and an anti-HER3 antibody, wherein:

(i) the anti-HER3 antibody comprises an antigen recognition domain having complementarity determining region (CDR) amino acid sequences as set forth in: SEQ ID NOs: 27 (CDR1), 28 (CDR2) and 29 (CDR3) (sequentially arranged from N to C on a light chain of the polypeptide) and 30 (CDR1), 31 (CDR2) and 32 (CDR3) (sequentially arranged from N to C on a heavy chain of the polypeptide) (Clone NG33);

(ii) the anti-EGFR antibody comprises an antigen recognition domain having complementarity determining region (CDR) amino acid sequences as set forth in: SEQ ID NOs: 15 (CDR1), 16 (CDR2) and 17 (CDR3) (sequentially arranged from N to C on a light chain of the polypeptide) and 18 (CDR1), 19 (CDR2) and 20 (CDR3) (sequentially arranged from N to C on a heavy chain of the polypeptide) (Clone 565, CNCM-4262) and the anti-HER2 antibody comprises an antigen recognition domain having complementarity determining region (CDR) amino acid sequences as set forth in: SEQ ID NOs: 21 (CDR1), 22 (CDR2) and 23 (CDR3) (sequentially arranged from N to C on a light chain of the polypeptide) and 24 (CDR1), 25 (CDR2) and 26 (CDR3) (sequentially arranged from N to C on a heavy chain of the polypeptide) (Clone N12, CNCM-I-4112);

(iii) the anti-EGFR antibody comprises an antigen recognition domain having complementarity determining region (CDR) amino acid sequences as set forth in: SEQ ID NOs: 15 (CDR1), 16 (CDR2) and 17 (CDR3) (sequentially arranged from N to C on a light chain of the polypeptide) and 18 (CDR1), 19 (CDR2) and 20 (CDR3) (sequentially arranged from N to C on a heavy chain of the polypeptide) (Clone 565, CNCM-4262) and the anti-HER3 antibody comprises an antigen recognition domain having complementarity determining region (CDR) amino acid sequences as set forth in: SEQ ID NOs: 27 (CDR1), 28 (CDR2) and 29 (CDR3) (sequentially arranged from N to C on a light chain of the polypeptide) and 30 (CDR1), 31 (CDR2) and 32 (CDR3) (sequentially arranged from N to C on a heavy chain of the polypeptide) (Clone NG33);

(iv) the anti-HER2 antibody an antigen recognition domain having complementarity determining region (CDR) amino acid sequences as set forth in: SEQ ID NOs: 21 (CDR1), 22 (CDR2) and 23 (CDR3) (sequentially arranged from N to C on a light chain of the polypeptide) and 24 (CDR1), 25 (CDR2) and 26 (CDR3) (sequentially arranged from N to C on a heavy chain of the polypeptide) (Clone N12, CNCM-I-4112) and the anti-HER3 antibody comprises an antigen recognition domain having complementarity determining region (CDR) amino acid sequences as set forth in: SEQ ID NOs: 27 (CDR1), 28 (CDR2) and 29 (CDR3) (sequentially arranged from N to C on a light chain of the polypeptide) and 30 (CDR1), 31 (CDR2) and 32 (CDR3) (sequentially arranged from N to C on a heavy chain of the polypeptide) (Clone NG33);

(v) the anti-EGFR antibody comprises an antigen recognition domain having complementarity determining region (CDR) amino acid sequences as set forth in: SEQ ID NOs: 15 (CDR1), 16 (CDR2) and 17 (CDR3) (sequentially arranged from N to C on a light chain of the polypeptide) and 18 (CDR1), 19 (CDR2) and 20 (CDR3) (sequentially arranged from N to C on a heavy chain of the polypeptide) (Clone 565, CNCM-4262), the anti-HER2 antibody comprises an antigen recognition domain having complementarity determining region (CDR) amino acid sequences as set forth in: SEQ ID NOs: 21 (CDR1), 22 (CDR2) and 23 (CDR3) (sequentially arranged from N to C on a light chain of the polypeptide) and 24 (CDR1), 25 (CDR2) and 26 (CDR3) (sequentially arranged from N to C on a heavy chain of the polypeptide) (Clone N12, CNCM-I-4112) and the anti-HER3 antibody comprises an antigen recognition domain having complementarity determining region (CDR) amino acid sequences as set forth in: SEQ ID NOs: 27 (CDR1), 28 (CDR2) and 29 (CDR3) (sequentially arranged from N to C on a light chain of the polypeptide) and 30 (CDR1), 31 (CDR2) and 32 (CDR3) (sequentially arranged from N to C on a heavy chain of the polypeptide) (Clone NG33);

(vi) the anti-EGFR antibody comprises cetuximab; and the anti-HER3 antibody comprises an antigen recognition domain having complementarity determining region (CDR) amino acid sequences as set forth in: SEQ ID NOs: 27 (CDR1), 28 (CDR2) and 29 (CDR3) (sequentially arranged from N to C on a light chain of the polypeptide) and 30 (CDR1), 31 (CDR2) and 32 (CDR3) (sequentially arranged from N to C on a heavy chain of the polypeptide) (Clone NG33);

(vii) the anti-HER2 antibody comprises trastuzumab; and the anti-HER3 antibody comprises an antigen recognition domain having complementarity determining region (CDR) amino acid sequences as set forth in: SEQ ID NOs: 27 (CDR1), 28 (CDR2) and 29 (CDR3) (sequentially arranged from N to C on a light chain of the polypeptide) and 30 (CDR1), 31 (CDR2) and 32 (CDR3) (sequentially arranged from N to C on a heavy chain of the polypeptide) (Clone NG33); and/or (viii) the anti-EGFR antibody comprises cetuximab, the anti-HER2 antibody comprises trastuzumab; and the anti-HER3 antibody comprises an antigen recognition domain having complementarity determining region (CDR) amino acid sequences as set forth in: SEQ ID NOs: 27 (CDR1), 28 (CDR2) and 29 (CDR3) (sequentially arranged from N to C on a light chain of the polypeptide) and 30 (CDR1), 31 (CDR2) and 32 (CDR3) (sequentially arranged from N to C on a heavy chain of the polypeptide) (Clone NG33).

According to an aspect of some embodiments of the present invention there is provided a pharmaceutical composition comprising as active ingredients an anti-EGFR antibody, an anti-HER2 antibody and an anti-HER3 antibody and a pharmaceutically acceptable carrier or diluents, wherein:

(i) the anti-HER3 antibody comprises an antigen recognition domain having complementarity determining region (CDR) amino acid sequences as set forth in: SEQ ID NOs: 27 (CDR1), 28 (CDR2) and 29 (CDR3) (sequentially arranged from N to C on a light chain of the polypeptide) and 30 (CDR1), 31 (CDR2) and 32 (CDR3) (sequentially arranged from N to C on a heavy chain of the polypeptide) (Clone NG33);

(ii) the anti-EGFR antibody comprises an antigen recognition domain having complementarity determining region (CDR) amino acid sequences as set forth in: SEQ ID NOs: 15 (CDR1), 16 (CDR2) and 17 (CDR3) (sequentially arranged from N to C on a light chain of the polypeptide) and 18 (CDR1), 19 (CDR2) and 20 (CDR3) (sequentially arranged from N to C on a heavy chain of the polypeptide) (Clone 565, CNCM-4262) and the anti-HER2 antibody comprises an antigen recognition domain having complementarity determining region (CDR) amino acid sequences as set forth in: SEQ ID NOs: 21 (CDR1), 22 (CDR2) and 23 (CDR3) (sequentially arranged from N to C on a light chain of the polypeptide) and 24 (CDR1), 25 (CDR2) and 26 (CDR3) (sequentially arranged from N to C on a heavy chain of the polypeptide) (Clone N12, CNCM-I-4112);

(iii) the anti-EGFR antibody comprises an antigen recognition domain having complementarity determining region (CDR) amino acid sequences as set forth in: SEQ ID NOs: 15 (CDR1), 16 (CDR2) and 17 (CDR3) (sequentially arranged from N to C on a light chain of the polypeptide) and 18 (CDR1), 19 (CDR2) and 20 (CDR3) (sequentially arranged from N to C on a heavy chain of the polypeptide) (Clone 565, CNCM-4262) and the anti-HER3 antibody comprises an antigen recognition domain having complementarity determining region (CDR) amino acid sequences as set forth in: SEQ ID NOs: 27 (CDR1), 28 (CDR2) and 29 (CDR3) (sequentially arranged from N to C on a light chain of the polypeptide) and 30 (CDR1), 31 (CDR2) and 32 (CDR3) (sequentially arranged from N to C on a heavy chain of the polypeptide) (Clone NG33);

(iv) the anti-HER2 antibody an antigen recognition domain having complementarity determining region (CDR) amino acid sequences as set forth in: SEQ ID NOs: 21 (CDR1), 22 (CDR2) and 23 (CDR3) (sequentially arranged from N to C on a light chain of the polypeptide) and 24 (CDR1), 25 (CDR2) and 26 (CDR3) (sequentially arranged from N to C on a heavy chain of the polypeptide) (Clone N12, CNCM-I-4112) and the anti-HER3 antibody comprises an antigen recognition domain having complementarity determining region (CDR) amino acid sequences as set forth in: SEQ ID NOs: 27 (CDR1), 28 (CDR2) and 29 (CDR3) (sequentially arranged from N to C on a light chain of the polypeptide) and 30 (CDR1), 31 (CDR2) and 32 (CDR3) (sequentially arranged from N to C on a heavy chain of the polypeptide) (Clone NG33);

(v) the anti-EGFR antibody comprises an antigen recognition domain having complementarity determining region (CDR) amino acid sequences as set forth in: SEQ ID NOs: 15 (CDR1), 16 (CDR2) and 17 (CDR3) (sequentially arranged from N to C on a light chain of the polypeptide) and 18 (CDR1), 19 (CDR2) and 20 (CDR3) (sequentially arranged from N to C on a heavy chain of the polypeptide) (Clone 565, CNCM-4262), the anti-HER2 antibody comprises an antigen recognition domain having complementarity determining region (CDR) amino acid sequences as set forth in: SEQ ID NOs: 21 (CDR1), 22 (CDR2) and 23 (CDR3) (sequentially arranged from N to C on a light chain of the polypeptide) and 24 (CDR1), 25 (CDR2) and 26 (CDR3) (sequentially arranged from N to C on a heavy chain of the polypeptide) (Clone N12, CNCM-I-4112) and the anti-HER3 antibody comprises an antigen recognition domain having complementarity determining region (CDR) amino acid sequences as set forth in: SEQ ID NOs: 27 (CDR1), 28 (CDR2) and 29 (CDR3) (sequentially arranged from N to C on a light chain of the polypeptide) and 30 (CDR1), 31 (CDR2) and 32 (CDR3) (sequentially arranged from N to C on a heavy chain of the polypeptide) (Clone NG33);

(vi) the anti-EGFR antibody comprises cetuximab; and the anti-HER3 antibody comprises an antigen recognition domain having complementarity determining region (CDR) amino acid sequences as set forth in: SEQ ID NOs: 27 (CDR1), 28 (CDR2) and 29 (CDR3) (sequentially arranged from N to C on a light chain of the polypeptide) and 30 (CDR1), 31 (CDR2) and 32 (CDR3) (sequentially arranged from N to C on a heavy chain of the polypeptide) (Clone NG33);

(vii) the anti-HER2 antibody comprises trastuzumab; and the anti-HER3 antibody comprises an antigen recognition domain having complementarity determining region (CDR) amino acid sequences as set forth in: SEQ ID NOs: 27 (CDR1), 28 (CDR2) and 29 (CDR3) (sequentially arranged from N to C on a light chain of the polypeptide) and 30 (CDR1), 31 (CDR2) and 32 (CDR3) (sequentially arranged from N to C on a heavy chain of the polypeptide) (Clone NG33); and/or (viii) the anti-EGFR antibody comprises cetuximab, the anti-HER2 antibody comprises trastuzumab; and the anti-HER3 antibody comprises an antigen recognition domain having complementarity determining region (CDR) amino acid sequences as set forth in: SEQ ID NOs: 27 (CDR1), 28 (CDR2) and 29 (CDR3) (sequentially arranged from N to C on a light chain of the polypeptide) and 30 (CDR1), 31 (CDR2) and 32 (CDR3) (sequentially arranged from N to C on a heavy chain of the polypeptide) (Clone NG33).

According to an aspect of some embodiments of the present invention there is provided an anti-EGFR antibody, an anti-HER2 antibody and an anti-HER3 antibody for use in treating cancer resistance to a tyrosine kinase inhibitor (TKI), wherein the TKI is directed to an ErbB family member and wherein cells of the cancer express the ErbB family member, wherein:

(i) the anti-EGFR antibody comprises an antigen recognition domain having complementarity determining region (CDR) amino acid sequences as set forth in: SEQ ID NOs: 15 (CDR1), 16 (CDR2) and 17 (CDR3) (sequentially arranged from N to C on a light chain of the polypeptide) and 18 (CDR1), 19 (CDR2) and 20 (CDR3) (sequentially arranged from N to C on a heavy chain of the polypeptide) (Clone 565, CNCM-4262);

(ii) the anti-HER2 antibody comprises an antigen recognition domain having complementarity determining region (CDR) amino acid sequences as set forth in: SEQ ID NOs: 21 (CDR1), 22 (CDR2) and 23 (CDR3) (sequentially arranged from N to C on a light chain of the polypeptide) and 24 (CDR1), 25 (CDR2) and 26 (CDR3) (sequentially arranged from N to C on a heavy chain of the polypeptide) (Clone N12, CNCM-I-4112);

(iii) the anti-HER3 antibody comprises an antigen recognition domain having complementarity determining region (CDR) amino acid sequences as set forth in: SEQ ID NOs: 27 (CDR1), 28 (CDR2) and 29 (CDR3) (sequentially arranged from N to C on a light chain of the polypeptide) and 30 (CDR1), 31 (CDR2) and 32 (CDR3) (sequentially arranged from N to C on a heavy chain of the polypeptide) (Clone NG33);

(iv) the anti-EGFR antibody comprises an antigen recognition domain having complementarity determining region (CDR) amino acid sequences as set forth in: SEQ ID NOs: 15 (CDR1), 16 (CDR2) and 17 (CDR3) (sequentially arranged from N to C on a light chain of the polypeptide) and 18 (CDR1), 19 (CDR2) and 20 (CDR3) (sequentially arranged from N to C on a heavy chain of the polypeptide) (Clone 565, CNCM-4262) and the anti-HER2 antibody comprises an antigen recognition domain having complementarity determining region (CDR) amino acid sequences as set forth in: SEQ ID NOs: 21 (CDR1), 22 (CDR2) and 23 (CDR3) (sequentially arranged from N to C on a light chain of the polypeptide) and 24 (CDR1), 25 (CDR2) and 26 (CDR3) (sequentially arranged from N to C on a heavy chain of the polypeptide) (Clone N12, CNCM-I-4112);

(v) the anti-EGFR antibody comprises an antigen recognition domain having complementarity determining region (CDR) amino acid sequences as set forth in: SEQ ID NOs: 15 (CDR1), 16 (CDR2) and 17 (CDR3) (sequentially arranged from N to C on a light chain of the polypeptide) and 18 (CDR1), 19 (CDR2) and 20 (CDR3) (sequentially arranged from N to C on a heavy chain of the polypeptide) (Clone 565, CNCM-4262) and the anti-HER3 antibody comprises an antigen recognition domain having complementarity determining region (CDR) amino acid sequences as set forth in: SEQ ID NOs: 27 (CDR1), 28 (CDR2) and 29 (CDR3) (sequentially arranged from N to C on a light chain of the polypeptide) and 30 (CDR1), 31 (CDR2) and 32 (CDR3) (sequentially arranged from N to C on a heavy chain of the polypeptide) (Clone NG33);

(vi) the anti-HER2 antibody comprises an antigen recognition domain having complementarity determining region (CDR) amino acid sequences as set forth in: SEQ ID NOs: 21 (CDR1), 22 (CDR2) and 23 (CDR3) (sequentially arranged from N to C on a light chain of the polypeptide) and 24 (CDR1), 25 (CDR2) and 26 (CDR3) (sequentially arranged from N to C on a heavy chain of the polypeptide) (Clone N12, CNCM-I-4112); and the anti-HER3 antibody comprises an antigen recognition domain having complementarity determining region (CDR) amino acid sequences as set forth in: SEQ ID NOs: 27 (CDR1), 28 (CDR2) and 29 (CDR3) (sequentially arranged from N to C on a light chain of the polypeptide) and 30 (CDR1), 31 (CDR2) and 32 (CDR3) (sequentially arranged from N to C on a heavy chain of the polypeptide) (Clone NG33);

(vii) the anti-EGFR antibody comprises an antigen recognition domain having complementarity determining region (CDR) amino acid sequences as set forth in: SEQ ID NOs: 15 (CDR1), 16 (CDR2) and 17 (CDR3) (sequentially arranged from N to C on a light chain of the polypeptide) and 18 (CDR1), 19 (CDR2) and 20 (CDR3) (sequentially arranged from N to C on a heavy chain of the polypeptide) (Clone 565, CNCM-4262), the anti-HER2 antibody comprises an antigen recognition domain having complementarity determining region (CDR) amino acid sequences as set forth in: SEQ ID NOs: 21 (CDR1), 22 (CDR2) and 23 (CDR3) (sequentially arranged from N to C on a light chain of the polypeptide) and 24 (CDR1), 25 (CDR2) and 26 (CDR3) (sequentially arranged from N to C on a heavy chain of the polypeptide) (Clone N12, CNCM-I-4112); and the anti-HER3 antibody comprises an antigen recognition domain having complementarity determining region (CDR) amino acid sequences as set forth in: SEQ ID NOs: 27 (CDR1), 28 (CDR2) and 29 (CDR3) (sequentially arranged from N to C on a light chain of the polypeptide) and 30 (CDR1), 31 (CDR2) and 32 (CDR3) (sequentially arranged from N to C on a heavy chain of the polypeptide) (Clone NG33);

(viii) the anti-EGFR antibody comprises cetuximab; and the anti-HER3 antibody comprises an antigen recognition domain having complementarity determining region (CDR) amino acid sequences as set forth in: SEQ ID NOs: 27 (CDR1), 28 (CDR2) and 29 (CDR3) (sequentially arranged from N to C on a light chain of the polypeptide) and 30 (CDR1), 31 (CDR2) and 32 (CDR3) (sequentially arranged from N to C on a heavy chain of the polypeptide) (Clone NG33);

(ix) the anti-HER2 antibody comprises trastuzumab; and the anti-HER3 antibody comprises an antigen recognition domain having complementarity determining region (CDR) amino acid sequences as set forth in: SEQ ID NOs: 27 (CDR1), 28 (CDR2) and 29 (CDR3) (sequentially arranged from N to C on a light chain of the polypeptide) and 30 (CDR1), 31 (CDR2) and 32 (CDR3) (sequentially arranged from N to C on a heavy chain of the polypeptide) (Clone NG33); and/or (x) the anti-EGFR antibody comprises cetuximab, the anti-HER2 antibody comprises trastuzumab; and the anti-HER3 antibody comprises an antigen recognition domain having complementarity determining region (CDR) amino acid sequences as set forth in: SEQ ID NOs: 27 (CDR1), 28 (CDR2) and 29 (CDR3) (sequentially arranged from N to C on a light chain of the polypeptide) and 30 (CDR1), 31 (CDR2) and 32 (CDR3) (sequentially arranged from N to C on a heavy chain of the polypeptide) (Clone NG33).

According to some embodiments of the invention, the method further comprising administering the TKI to the subject.

According to some embodiments of the invention, the method further comprising administering an additional TKI to the subject which is different from the TKI.

According to an aspect of some embodiments of the present invention there is provided a method of treating a subject having cancer exhibiting a resistance to a tyrosine kinase inhibitor (TKI), wherein the TKI is directed to an ErbB family member and wherein cells of the cancer express the ErbB family member, the method comprising administering to the subject a therapeutically effective amount of an additional TKI and a therapeutically effective amount of at least one antibody specifically binding EGFR, HER2 and HER3, wherein the additional TKI is different from the TKI and wherein the cancer does not exhibit resistance to the additional TKI.

According to an aspect of some embodiments of the present invention there is provided a use of a tyrosine kinase inhibitor (TKI) and at least one antibody specifically binding EGFR, HER2 and HER3 for the manufacture of a medicament for treating cancer resistance to a TKI, wherein the TKI is directed to an ErbB family member and wherein cells of the cancer express the ErbB family member and wherein the TKI is an additional TKI different from the TKI to which the cancer is resistant.

According to some embodiments of the invention, the at least one antibody comprises an anti-EGFR antibody, an anti-HER2 antibody and an anti-HER3 antibody, wherein:

(i) the anti-EGFR antibody comprises an antigen recognition domain having complementarity determining region (CDR) amino acid sequences as set forth in: SEQ ID NOs: 15 (CDR1), 16 (CDR2) and 17 (CDR3) (sequentially arranged from N to C on a light chain of the polypeptide) and 18 (CDR1), 19 (CDR2) and 20 (CDR3) (sequentially arranged from N to C on a heavy chain of the polypeptide) (Clone 565, CNCM-4262);

(ii) the anti-HER2 antibody comprises an antigen recognition domain having complementarity determining region (CDR) amino acid sequences as set forth in: SEQ ID NOs: 21 (CDR1), 22 (CDR2) and 23 (CDR3) (sequentially arranged from N to C on a light chain of the polypeptide) and 24 (CDR1), 25 (CDR2) and 26 (CDR3) (sequentially arranged from N to C on a heavy chain of the polypeptide) (Clone N12, CNCM-I-4112);

(iii) the anti-HER3 antibody comprises an antigen recognition domain having complementarity determining region (CDR) amino acid sequences as set forth in: SEQ ID NOs: 27 (CDR1), 28 (CDR2) and 29 (CDR3) (sequentially arranged from N to C on a light chain of the polypeptide) and 30 (CDR1), 31 (CDR2) and 32 (CDR3) (sequentially arranged from N to C on a heavy chain of the polypeptide) (Clone NG33);

(iv) the anti-EGFR antibody comprises an antigen recognition domain having complementarity determining region (CDR) amino acid sequences as set forth in: SEQ ID NOs: 15 (CDR1), 16 (CDR2) and 17 (CDR3) (sequentially arranged from N to C on a light chain of the polypeptide) and 18 (CDR1), 19 (CDR2) and 20 (CDR3) (sequentially arranged from N to C on a heavy chain of the polypeptide) (Clone 565, CNCM-4262) and the anti-HER2 antibody comprises an antigen recognition domain having complementarity determining region (CDR) amino acid sequences as set forth in: SEQ ID NOs: 21 (CDR1), 22 (CDR2) and 23 (CDR3) (sequentially arranged from N to C on a light chain of the polypeptide) and 24 (CDR1), 25 (CDR2) and 26 (CDR3) (sequentially arranged from N to C on a heavy chain of the polypeptide) (Clone N12, CNCM-I-4112);

(v) the anti-EGFR antibody comprises an antigen recognition domain having complementarity determining region (CDR) amino acid sequences as set forth in: SEQ ID NOs: 15 (CDR1), 16 (CDR2) and 17 (CDR3) (sequentially arranged from N to C on a light chain of the polypeptide) and 18 (CDR1), 19 (CDR2) and 20 (CDR3) (sequentially arranged from N to C on a heavy chain of the polypeptide) (Clone 565, CNCM-4262) and the anti-HER3 antibody comprises an antigen recognition domain having complementarity determining region (CDR) amino acid sequences as set forth in: SEQ ID NOs: 27 (CDR1), 28 (CDR2) and 29 (CDR3) (sequentially arranged from N to C on a light chain of the polypeptide) and 30 (CDR1), 31 (CDR2) and 32 (CDR3) (sequentially arranged from N to C on a heavy chain of the polypeptide) (Clone NG33);

(vi) the anti-HER2 antibody comprises an antigen recognition domain having complementarity determining region (CDR) amino acid sequences as set forth in: SEQ ID NOs: 21 (CDR1), 22 (CDR2) and 23 (CDR3) (sequentially arranged from N to C on a light chain of the polypeptide) and 24 (CDR1), 25 (CDR2) and 26 (CDR3) (sequentially arranged from N to C on a heavy chain of the polypeptide) (Clone N12, CNCM-I-4112); and the anti-HER3 antibody comprises an antigen recognition domain having complementarity determining region (CDR) amino acid sequences as set forth in: SEQ ID NOs: 27 (CDR1), 28 (CDR2) and 29 (CDR3) (sequentially arranged from N to C on a light chain of the polypeptide) and 30 (CDR1), 31 (CDR2) and 32 (CDR3) (sequentially arranged from N to C on a heavy chain of the polypeptide) (Clone NG33);

(vii) the anti-EGFR antibody comprises an antigen recognition domain having complementarity determining region (CDR) amino acid sequences as set forth in: SEQ ID NOs: 15 (CDR1), 16 (CDR2) and 17 (CDR3) (sequentially arranged from N to C on a light chain of the polypeptide) and 18 (CDR1), 19 (CDR2) and 20 (CDR3) (sequentially arranged from N to C on a heavy chain of the polypeptide) (Clone 565, CNCM-4262), the anti-HER2 antibody comprises an antigen recognition domain having complementarity determining region (CDR) amino acid sequences as set forth in: SEQ ID NOs: 21 (CDR1), 22 (CDR2) and 23 (CDR3) (sequentially arranged from N to C on a light chain of the polypeptide) and 24 (CDR1), 25 (CDR2) and 26 (CDR3) (sequentially arranged from N to C on a heavy chain of the polypeptide) (Clone N12, CNCM-I-4112); and the anti-HER3 antibody comprises an antigen recognition domain having complementarity determining region (CDR) amino acid sequences as set forth in: SEQ ID NOs: 27 (CDR1), 28 (CDR2) and 29 (CDR3) (sequentially arranged from N to C on a light chain of the polypeptide) and 30 (CDR1), 31 (CDR2) and 32 (CDR3) (sequentially arranged from N to C on a heavy chain of the polypeptide) (Clone NG33);

(viii) the anti-EGFR antibody comprises cetuximab; and the anti-HER3 antibody comprises an antigen recognition domain having complementarity determining region (CDR) amino acid sequences as set forth in: SEQ ID NOs: 27 (CDR1), 28 (CDR2) and 29 (CDR3) (sequentially arranged from N to C on a light chain of the polypeptide) and 30 (CDR1), 31 (CDR2) and 32 (CDR3) (sequentially arranged from N to C on a heavy chain of the polypeptide) (Clone NG33);

(ix) the anti-HER2 antibody comprises trastuzumab; and the anti-HER3 antibody comprises an antigen recognition domain having complementarity determining region (CDR) amino acid sequences as set forth in: SEQ ID NOs: 27 (CDR1), 28 (CDR2) and 29 (CDR3) (sequentially arranged from N to C on a light chain of the polypeptide) and 30 (CDR1), 31 (CDR2) and 32 (CDR3) (sequentially arranged from N to C on a heavy chain of the polypeptide) (Clone NG33); and/or (x) the anti-EGFR antibody comprises cetuximab, the anti-HER2 antibody comprises trastuzumab; and the anti-HER3 antibody comprises an antigen recognition domain having complementarity determining region (CDR) amino acid sequences as set forth in: SEQ ID NOs: 27 (CDR1), 28 (CDR2) and 29 (CDR3) (sequentially arranged from N to C on a light chain of the polypeptide) and 30 (CDR1), 31 (CDR2) and 32 (CDR3) (sequentially arranged from N to C on a heavy chain of the polypeptide) (Clone NG33).

According to some embodiments of the invention, the ErbB family member is EGFR.

According to some embodiments of the invention, the TKI is selected from the group consisting of erlotinib, gefitinib and lapatinib.

According to some embodiments of the invention, the additional TKI is an irreversible TKI.

According to some embodiments of the invention, the additional TKI binds an ErbB receptor having a mutation in a kinase domain of the receptor.

According to some embodiments of the invention, the additional TKI does not bind a wild-type ErbB receptor.

According to some embodiments of the invention, the additional TKI is selected from the group consisting of perlitinib (EKB-569), neratinib (HKI-272), canertinib (CI-1033), vandetanib (ZD6474), afatinib, dacomitinib, AZD9291, rociletinib (CO-1686), HM61713 and WZ4002.

According to some embodiments of the invention, the additional TKI is AZD9291.

According to some embodiments of the invention, the TKI is erlotinib and the additional TKI is AZD9291.

According to some embodiments of the invention, the TKI is AZD9291.

According to some embodiments of the invention, the additional TKI is administered below gold standard dosing as a single agent.

According to some embodiments of the invention, the additional TKI is administered at a dose that does not exert at least one side effect selected from the group consisting of skin rash, diarrhea, mouth sores, paronychia, fatigue, hyperglycemia, hepatotoxicity, kidney failure, cardiovascular effects, electrolytes anomalies and GI perforations.

According to some embodiments of the invention, the cancer is lung cancer.

According to some embodiments of the invention, the lung cancer is a non-small cell lung cancer (NSCLC).

According to some embodiments of the invention, the cells of the cancer express an ErbB receptor having a mutation in a kinase domain of the receptor.

According to some embodiments of the invention, the mutation does not substantially affect a kinase activity of the ErbB.

According to some embodiments of the invention, the ErbB is EGFR.

According to some embodiments of the invention, the mutation comprises a substitution of Threonine to Methionine at position 790 (T790M) or a Cysteine to Serine at position 797 (C797S).

According to some embodiments of the invention, the method further comprising subjecting the subject to a therapy selected from the group consisting of a radiotherapy and a chemotherapy.

According to some embodiments of the invention, the administering comprises multiple administrations.

According to some embodiments of the invention, the multiple administrations comprise bi-weekly administrations.

According to some embodiments of the invention, the packaging material comprises at least two containers for packaging the antibodies.

According to some embodiments of the invention, the active ingredients are in a co-formulation.

According to some embodiments of the invention, the active ingredients are in separate formulations.

According to some embodiments of the invention, the antibody is a recombinant antibody.

According to some embodiments of the invention, the antibody is a monoclonal antibody.

According to some embodiments of the invention, the antibody is a humanized or partially humanized antibody.

According to some embodiments of the invention, the antibodies are selected causing at least 50% reduction in tumor volume as compared to a control in a xenograft mouse model.

According to some embodiments of the invention, the antibodies are selected synergistic with chemotherapy.

According to some embodiments of the invention, the method further comprises administering the TKI to the subject.

According to some embodiments of the invention, the resistance is acquired resistance.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 1A-E demonstrate that treatment with anti-EGFR monoclonal antibodies (mAb) induces up-regulation of HER2 and HER3 in EGFR TKI-resistant PC9ER and H1975 non-small cell lung cancer (NSCLC) cell lines. FIG. 1A shows percentages of cell survival following 72 hours treatment with increasing doses of erlotinib (top) or cetuximab (bottom), as evaluated by MTT assay. Data is presented as average±SD (n=3 experiments). FIG. 1B shows representative western-blot photographs demonstrating reduced expression of EGFR and increased expression of HER2, HER2 and their activated phosphorylated forms following treatment with mAb 565 (top) or cetuximab (bottom). FIG. 1C shows bar graphs of HER2 and HER3 mRNA levels following treatment with 10 µg/ml anti-EGFR mAb 565, as evaluated by quantitative real-time PCR. Data is presented as average±SD (n=3 experiments), *p≤0.05; ** p≤0.01. FIGS. 1D-E shows bars graphs of relative luciferase activity in PC9ER (FIG. 1D) and H1975 (FIG. 1E) cells co-transfected with pmCherry-Renilla and pGM3-Firefly luciferase reporter plasmids corresponding to the HER2 promoter (left) or HER3 promoter (right) following treatment with anti-EGFR mAb 565 (top) or cetuximab (bottom). Cells transfected with an empty pGM3 plasmid (empty vector) and a pGM3-Firefly vector with a SV40 promoter (SV40 promoter) served as negative and positive controls, respectively. Data is presented as average (n=3) of a representative experiment.

Figure 2:
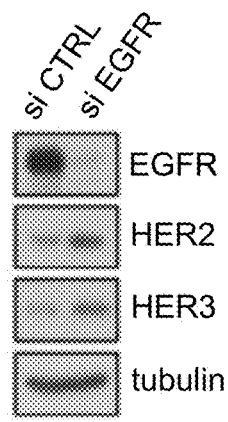

FIG. 2 is a representative western-blot photograph demonstrating depletion of EGFR and increased HER2 and HER3 protein levels in NSCLC PC9ER cells 2 days following transfection with 50 pM EGFR-specific siRNA as compared to control siRNAs.

Figure 3:
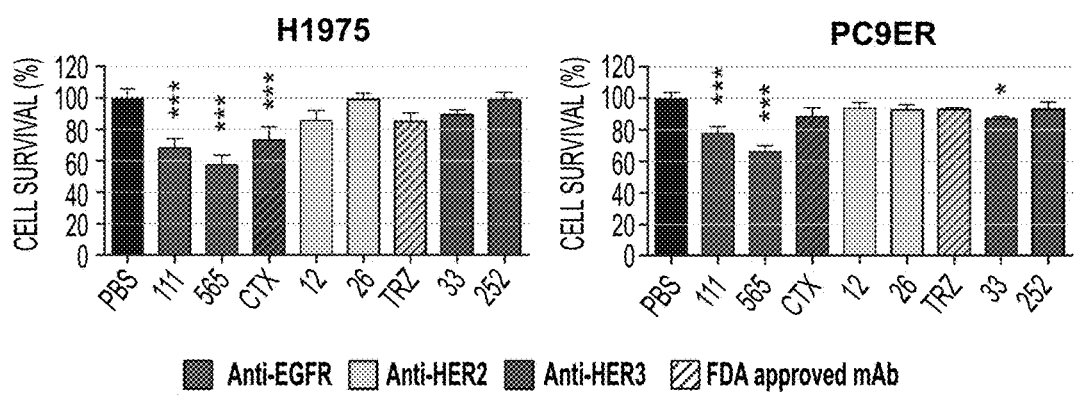

FIG. 3 shows bars graphs representing the survival percentages of NSCLC H1975 (left) and PC9ER (right) cells 4 days following treatment initiation with 10 µg/ml of the indicated anti-EGFR, anti-HER2 or anti-HER3 mAbs, as evaluated by MTT assay. Data is presented as average±SD (n=3), *p≤0.05;  p≤0.01; * p≤0.001.

Figure 4:
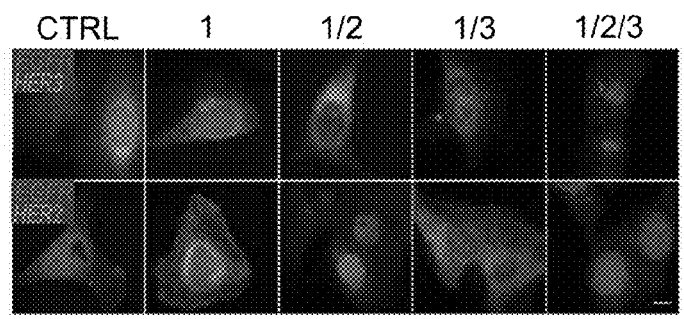

FIG. 4 shows fluorescent microscope photographs demonstrating expression of EGFR (red), HER3 (green, upper panel) and HER2 (green, lower panel) in NSCLC H1975 cells 24 hours following treatment with 10 µg/ml anti-EGFR (mAb 565, denoted 1), anti-EGFR+anti-HER2 (mAb 565+ mAb 12, denoted 1/2), anti-EGFR+anti-HER3 (mAb 565+ mAb 33, denoted 1/3) or anti-EGFR+anti-HER2+anti-HER3 (mAb 565+mAb 12+mAb 33, denoted 1/2/3). Scale bar: 4 µm.

Figure 5A:
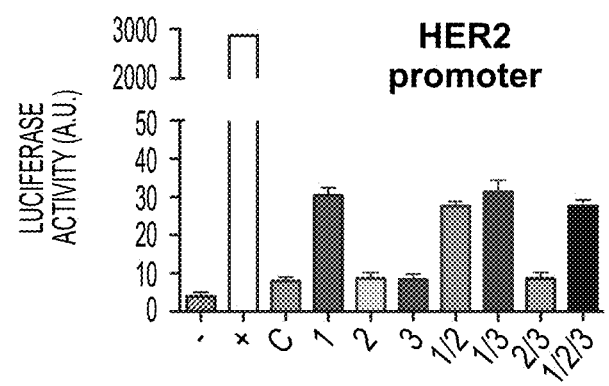
Figure 5B:
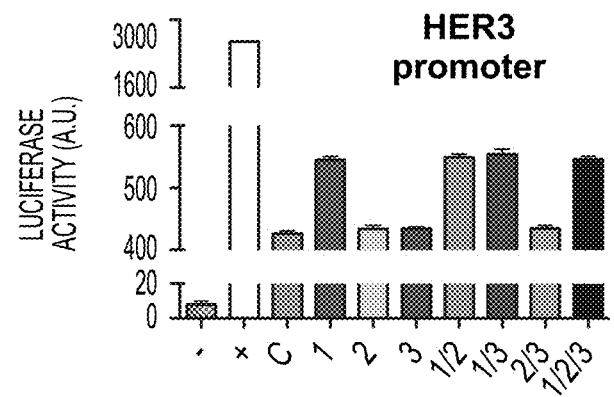

FIGS. 5A-B demonstrate that an anti-EGFR mAb activates the promoters of HER2 and HER3. NSCLC PC9ER cells stably expressing pmCherry-Renilla or pGM3-Firefly luciferase promoter reporter plasmids corresponding to HER2 (FIG. 5A) or HER3 (FIG. 5B) were treated with 10 µg/ml anti-EGFR (mAb 565, denoted 1), anti-HER2 (mAb 12, denoted 2) and anti-HER3 (mAb 33, denoted 3) and all possible combinations of the three. Controls included buffer (C), an empty pGM3 vector as negative control (−) and pGM3-Firefly with a SV40 promoter as positive control (+). Data is presented as average±SD (n=3) of a representative experiment.

Figure 6:
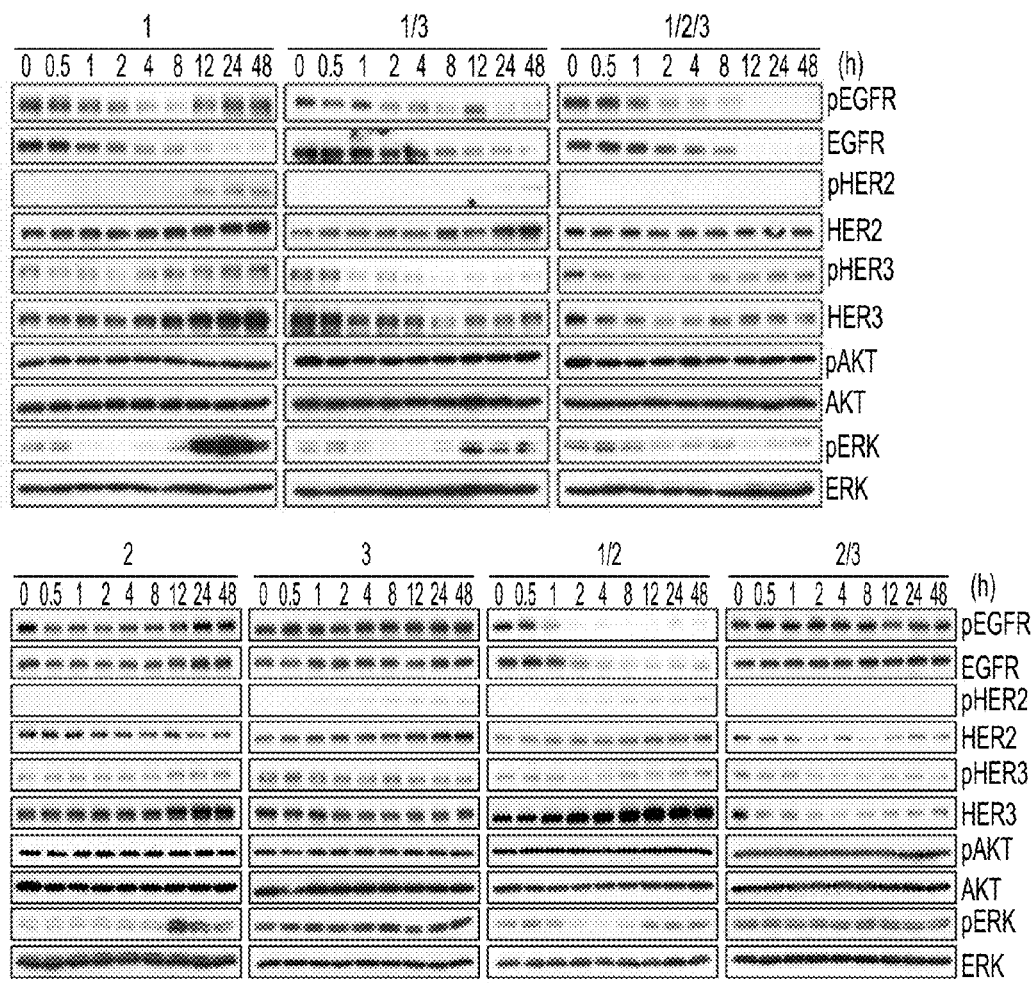

FIG. 6 shows western-blot photographs demonstrating expression of EGFR, HER2, HER3, AKT, ERK and their phosphorylated forms in NSCLC PC9ER cells following treatment with 10 µg/ml anti-EGFR (mAb 565, denoted 1), anti-HER2 (mAb 12, denoted 2) and anti-HER3 (mAb 33, denoted 3) and combinations of the three.

Figure 7A:
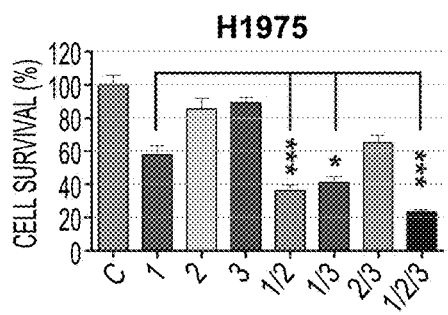
Figure 7B:
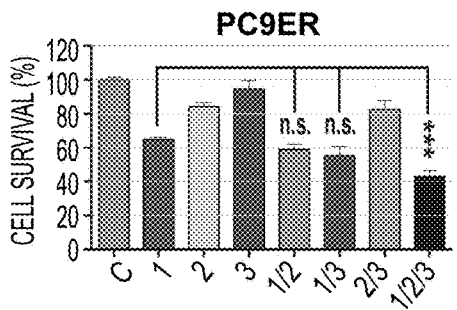
Figure 7C:
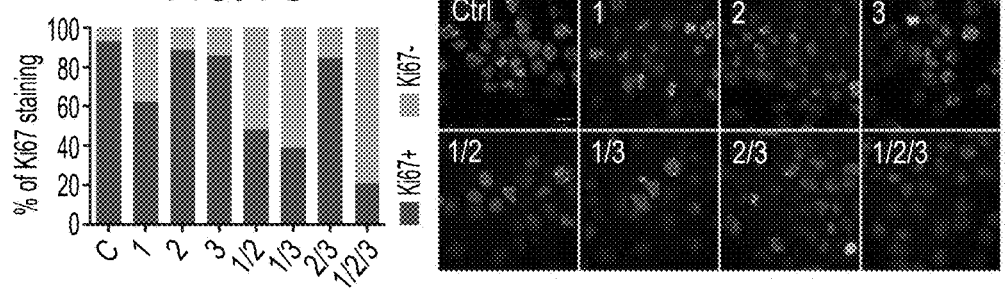

FIGS. 7A-C demonstrate that triple mAb combination better inhibits NSCLC cells growth. FIGS. 7A-B are bar graphs representing survival percentages of H1975 (FIG. 7A) and PC9ER (FIG. 7B) cells 4 days following treatment with 10 μg/ml anti-EGFR (mAb 565, denoted 1), anti-HER2 (mAb 12, denoted 2) and anti-HER3 (mAb 33, denoted 3) and combinations of the three, as evaluated by MTT assay. Data is presented as average±SD (n=3 experiments); *p≤0.05;  p≤0.01; * p≤0.001. FIG. 7C shows fluorescent microscopy photographs (left) and the respective quantified bar graphs (right) of Ki67 staining (green) in H1975 cells 4 days following treatment with 10 μg/ml anti-EGFR (mAb 565, denoted 1), anti-HER2 (mAb 12, denoted 2) and anti-HER3 (mAb 33, denoted 3) and combinations of the three. Cells were counterstained with DAPI (blue). Scale bar: 10 μm.

Figure 8A:
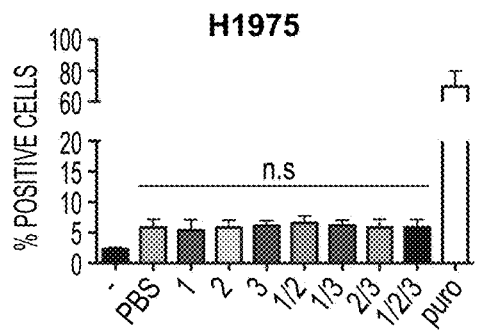
Figure 8B:
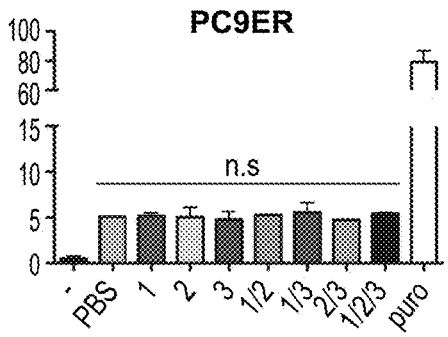
Figure 8C:
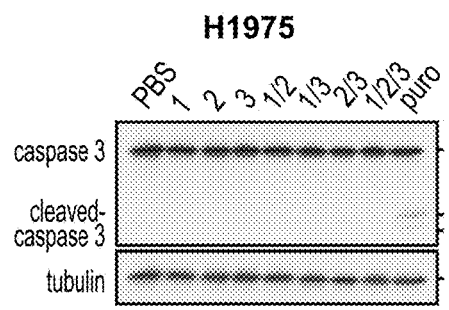
Figure 8D:
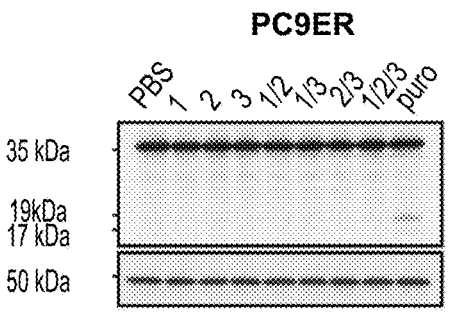

FIGS. 8A-D demonstrate that mAbs treatment does not induce apoptosis in NSCLC cells. FIGS. 8A-B are bar graphs representing percentages of propidium iodide (PI) positive H1975 (FIG. 8A) and PC9ER (FIG. 8B) cells 48 hours following treatment with PBS or 10 μg/ml anti-EGFR (mAb 565, denoted 1), anti-HER2 (mAb 12, denoted 2) and anti-HER3 (mAb 33, denoted 3) and combinations of the three, as evaluated by flow cytometry. Unstained cells served as negative control (−) and treatment with 0.5 μg/ml puromycin served as positive control (+). FIGS. 8C-D are western blot photographs demonstrating expression of Caspase-3 in H1975 (FIG. 8C) and PC9ER (FIG. 8D) cells 72 hours following treatment with PBS or 10 μg/ml anti-EGFR (mAb 565, denoted 1), anti-HER2 (mAb 12, denoted 2) and anti-HER3 (mAb 33, denoted 3) and combinations of the three. Treatment with 0.5 μg/ml puromycin served as positive control (+).

Figure 9A:
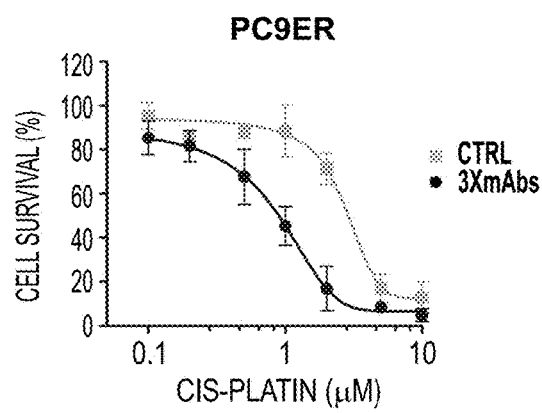
Figure 9B:
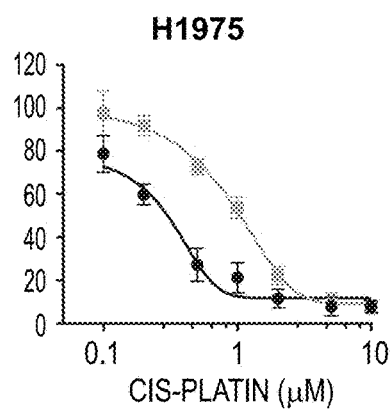

FIGS. 9A-B show bar graphs representing the survival percentages of NSCLC H1975 (FIG. 9A) and PC9ER (FIG. 9B) cells 3 days following treatment with increasing concentrations of cis-platin (control) or with a mixture of cis-platin and 10 μg/ml anti-EGFR+anti-HER2+anti-HER3 (mAb 565+mAb 12+mAb 33, respectively, denoted 3×mAbs), as evaluated by MTT assay. Data is presented as average±SD (n=2 experiments).

Figure 10:
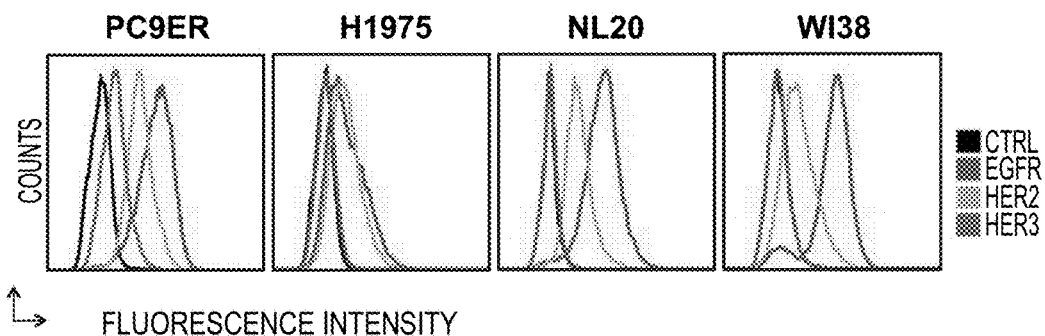

FIG. 10 shows flow cytometry histograms of EGFR, HER2 and HER3 cell surface expression in the lung-derived cell lines PC9ER, H1975, NL20 and WI38.

Figure 11:
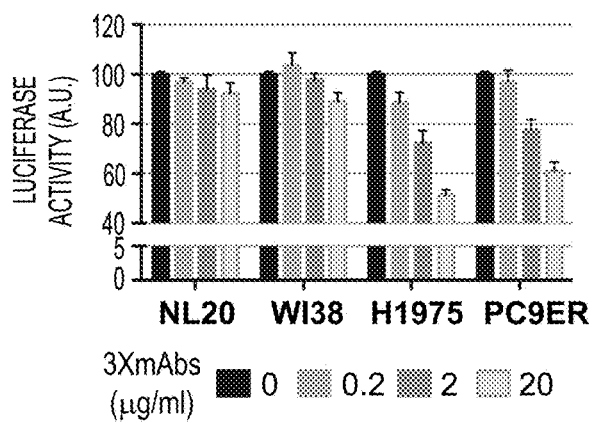

FIG. 11 is a bar graph representing survival of NL20 and WI38 cells stably transfected with a Cherry-Renilla construct and NSCLC PC9ER and H1975 cells infected with a GFP-Firefly construct, 3 days following treatment with increasing concentrations of anti-EGFR+anti-HER2+anti-HER3 (mAb 565+mAb 12+mAb 33, respectively, denoted 3×mAbs), as evaluated by luciferase activity.

Figure 12A:
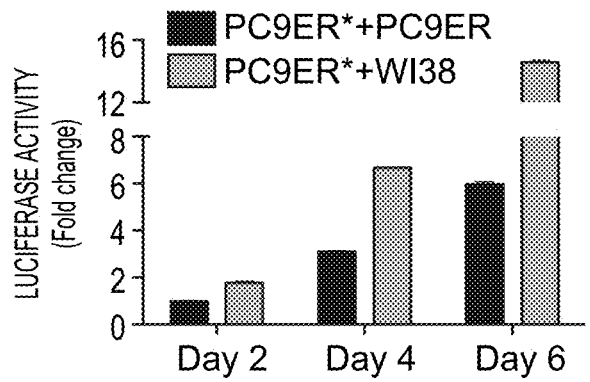
Figure 12B:
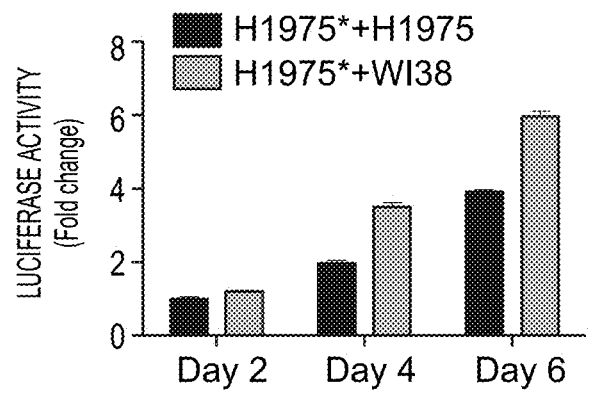
Figure 12C:
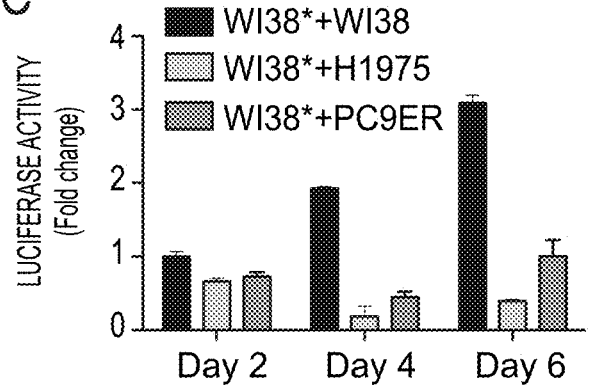

FIGS. 12A-C are bar graphs representing growth as evaluated by luciferase activity and demonstrating that co-culturing NSCLC cells with non-cancerous lung fibroblasts increases growth of the cancerous cells while decreases growth of the non-cancerous fibroblasts. FIGS. 12A-B show GFP-Firefly infected PC9ER (FIG. 12A) or H1975 (FIG. 12B) NSCLC cells (marked by asterisks) co-cultured with unlabelled non-cancerous WI38 lung fibroblasts. GFP-Firefly infected cancer cells co-cultured with the same non-infected cancer cells served as control. FIG. 12C shows mCherry-Renilla transfected WI38 (marked by asterisks) co-cultured with non-infected H1975 or PC9ER. mCherry-Renilla transfected WI38 cells co-cultured with non-transfected WI38 cells served as control.

Figure 13A:
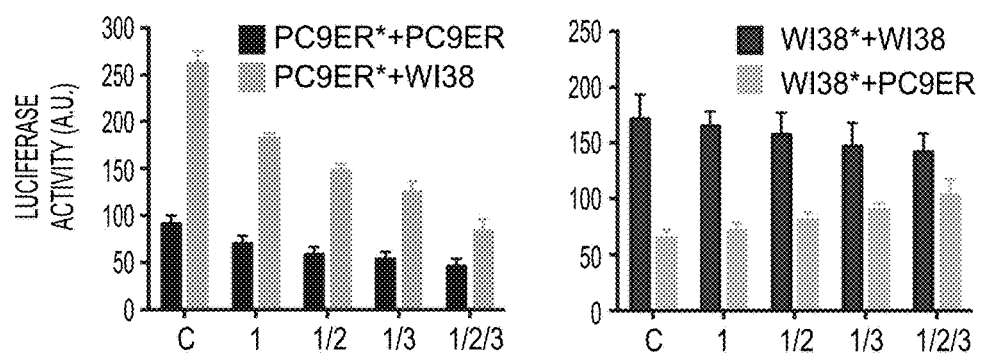
Figure 13B:
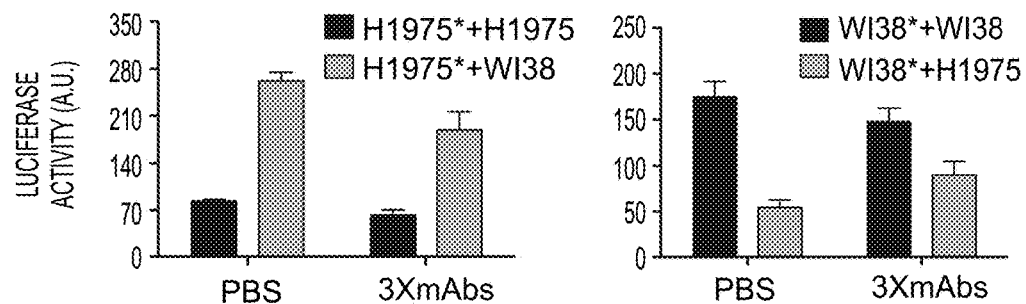

FIGS. 13A-B are bar graphs representing growth as evaluated by luciferase activity of co-cultured NSCLC cells (H1975 or PC9ER) 5 days following treatment with PBS (denoted C) or 10 μg/ml anti-EGFR (mAb 565, denoted 1), anti-HER2 (mAb 12, denoted 2) and anti-HER3 (mAb 33, denoted 3) and combinations of the three. The GFP-Firefly infected PC9ER cells and mCherry-Renilla transfected WI38 cells are marked with asterisks. Data is presented as average±SD (n=3).

Figure 14A:
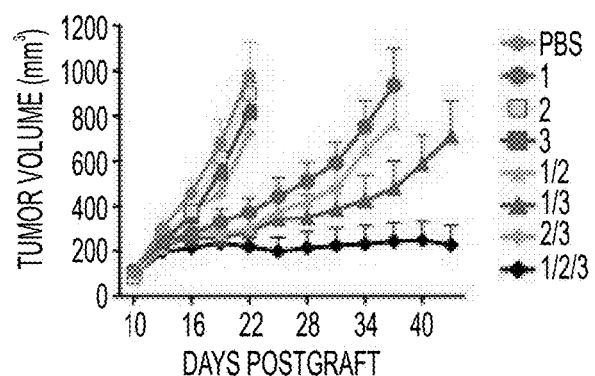
Figure 14B:
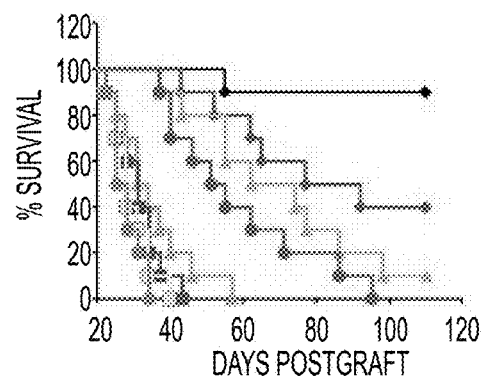
Figure 14C:
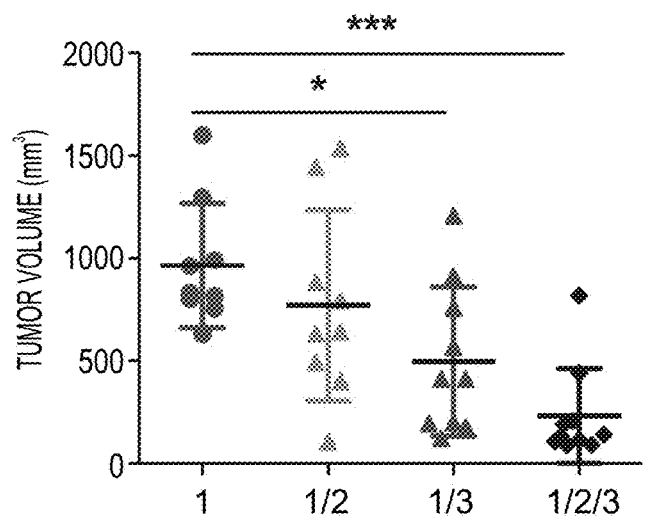

FIGS. 14A-C show the in-vivo effect of treatment with PBS or anti-EGFR (mAb 565, denoted 1), anti-HER2 (mAb 12, denoted 2) and anti-HER3 (mAb 33, denoted 3) and combinations of the three on survival and tumor growth in mice inoculated with H1975 NSCLC cells. FIG. 14B is a graph representing tumor volumes following treatment. Data is presented as average±SE. FIG. 14B is Kaplan-Meier survival curve of tumor-bearing mice. FIG. 14C is a boxplot presenting the values of tumor volumes 37 days following inoculation of H1975 cells. Data is presented as mean (horizontal black line)±SD, while each symbol represents a single animal. *p≤0.05; ***p≤0.001.

Figure 15:
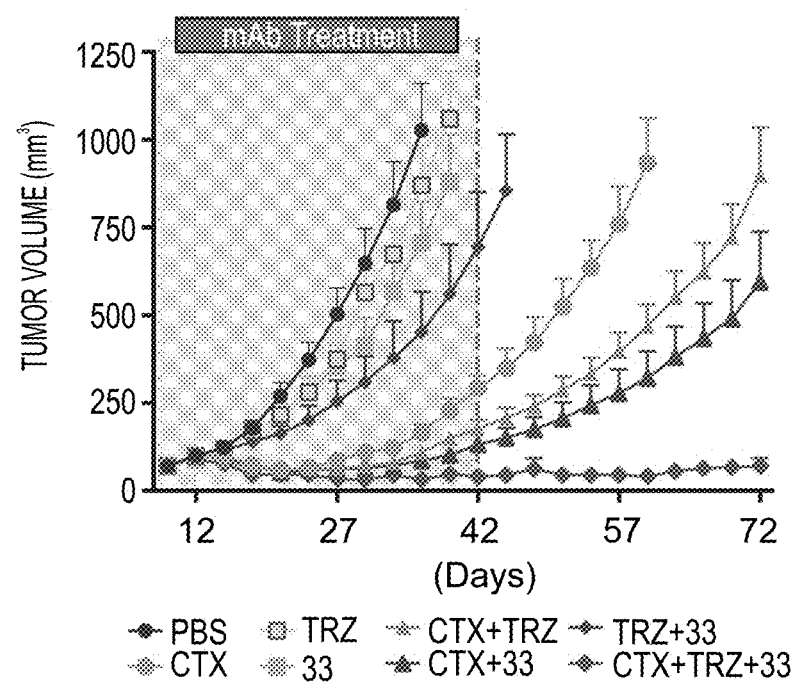

FIG. 15 shows the in-vivo effect of treatment with PBS or cetuximab (denoted CTX), trastuzumab (denoted TRZ) and anti-HER3 (mAb 33, denoted 33) and combinations of the three on tumor growth in mice inoculated with PC9ER NSCLC cells. The graph represents tumor volumes following treatment. Data is presented as mean±SE (n=9).

Figure 16A:
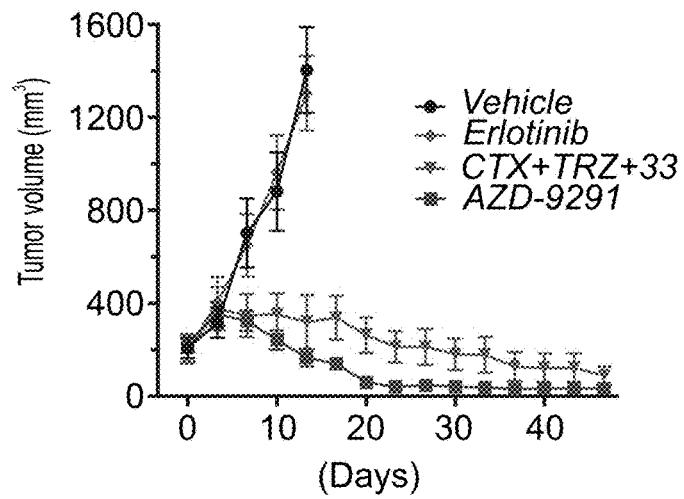
Figure 16B:
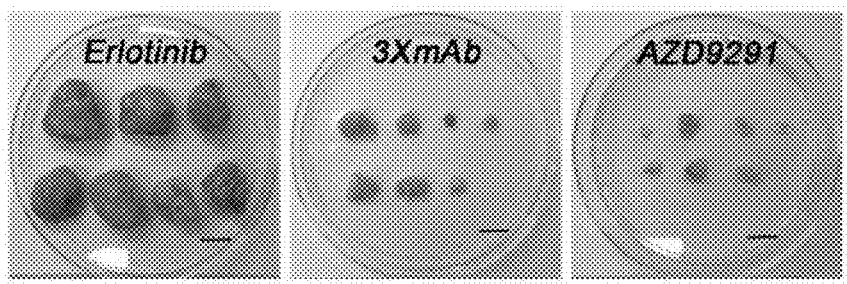
Figure 16C:
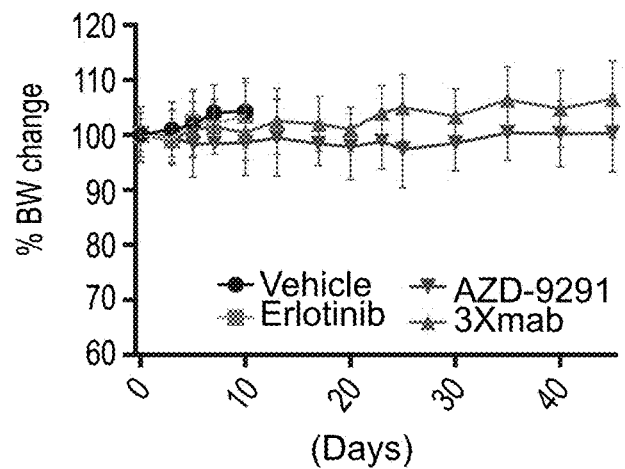

FIGS. 16A-C show that treatment with AZD-9291 (a third generation TKI) and combined treatment with cetuximab (denoted CTX), Trastuzumab (denoted TRZ) and anti-HER3 (mAb 33, denoted 33) comparably inhibit erlotinib resistant NSCLC tumor growth in-vivo. CD1-nu/nu mice were inoculated with H1975 NSCLC cells and treated with Vehicle, Erlotinib or AZD9291 (5 mg/kg/day) or with the triple combination of antibodies (CTX+TRZ+33). FIG. 16A is a graph representing tumor volumes following treatment. Data is presented as mean±SE (n=8). FIG. 16B shows photographs demonstrating tumors harvested from the tumor bearing mice. The images show tumors harvested from Erlotinib treated mice on day 14 and from AZD9291 or the triple combination of antibodies (denoted as 3×mAb) treated mice on day 43. Scale bar represents 1 cm. FIG. 16C is a graph representing body weight changes following treatment.

Figure 17:
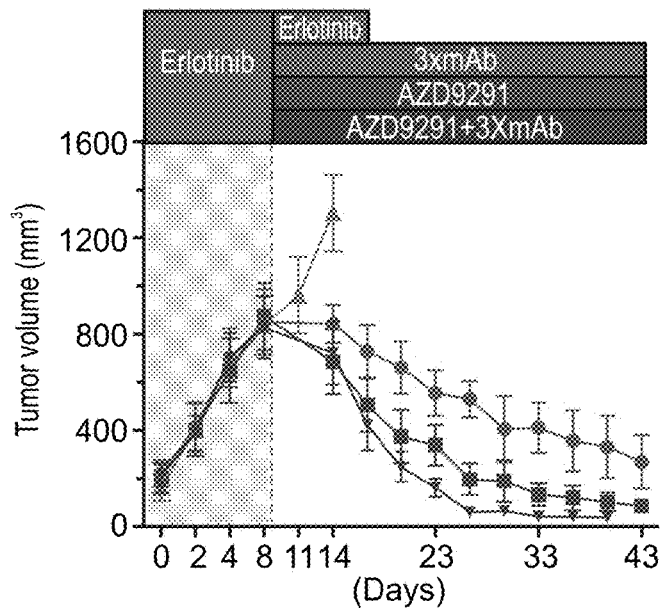

FIG. 17 shows the in-vivo effect of a combined treatment with AZD-9291 and the triple antibody combination (cetuximab+trastuzumab+mAb 33, denoted 3×mAb) on erlotinib resistant NSCLC tumor growth in mice inoculated with H1975 cells. CD1-nu/nu mice were first treated with Erlotinib until tumors reached a size of 800 mm$^3$ followed by treatment with Erlotinib or AZD9291 (5 mg/kg/day), 3×mAb or 3×mAb in combination with AZD9291 (1 mg/kg/day). The graph represents tumor volumes following treatment. Data is presented as mean±SE (n=7).

Figure 18:
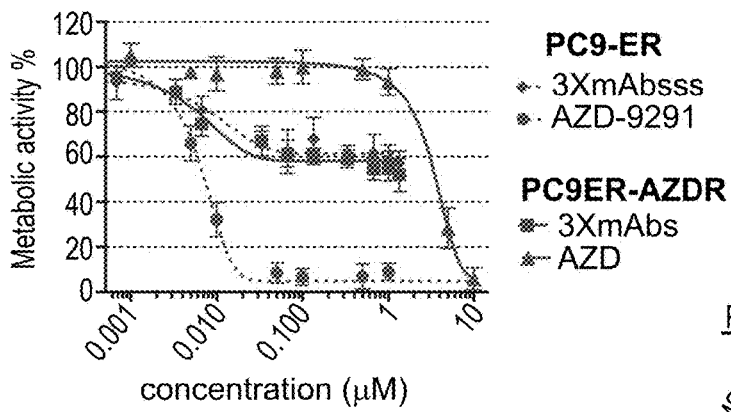

FIG. 18 demonstrates that NSCLC cells develop resistance to AZD-9291 (denoted AZD) but remain sensitive to treatment with the triple mAb combination (cetuximab+trastuzumab+mAb33, denoted 3×mAb). The graph represents metabolic activity percentages of PC9ER and PC9ER-AZDR cells following 72 hours treatment with increasing doses of AZD-9291 or 3×mAb, as evaluated by MTT assay. Data is presented as average±SD (n=3 independent experiments).

Figure 19:
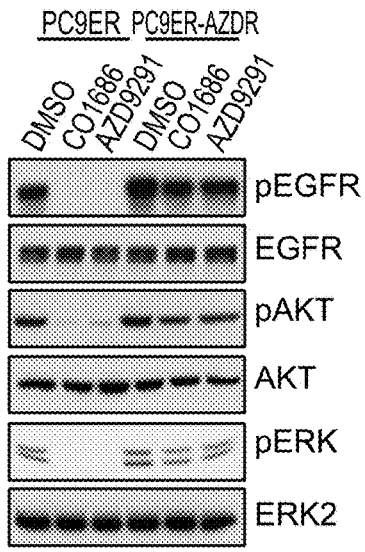

FIG. 19 shows western-blot photographs demonstrating expression of EGFR, AKT, ERK2 and their phosphorylated forms in NSCLC PC9ER and PC9ER-AZDR cells following 6 hours treatment with DMSO control, 1 μM CO-1686 or 1 μM AZD-9291.

Figure 20:
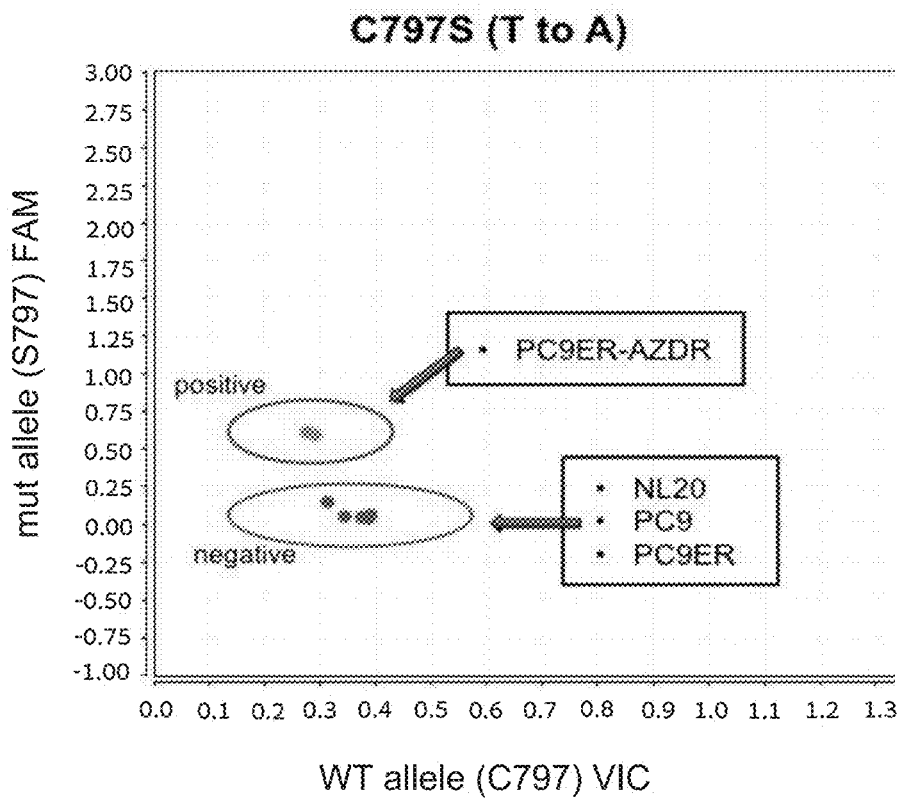

FIG. 20 shows that NSCLC cells that acquired resistance to a third generation inhibitor express a newly described mutation, C797S. The shown plot chart presents results of targeted EGFR sequencing analysis performed on the indicated cell lines. The analysis specifically detects a C797S (T→A) mutation in genomic DNA extracts. Note that NL20 (normal lung epithelial cells), and both PC9 and the erlotinib-resistant variant, PC9-ER cells, do not express the C797S mutant form of EGFR.

Figure 21:
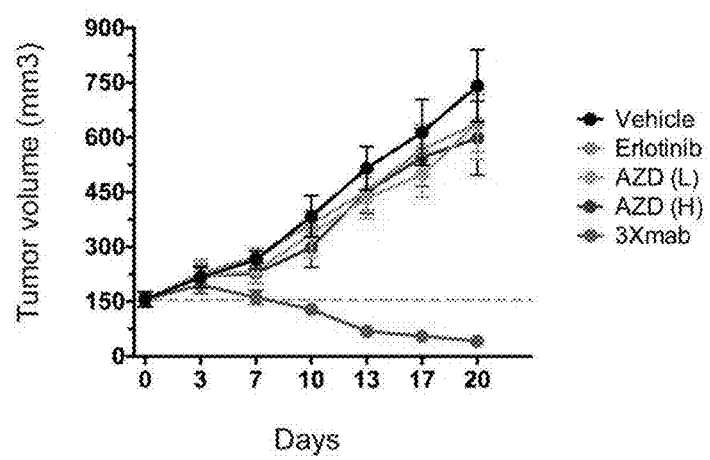

FIG. 21 shows NSCLC cells that acquired the new mutation, C797S, gave rise to tumors that are resistant to treatment with AZD9291, while such tumors remained highly sensitive to treatment with the mixture of three antibodies. A derivative of PC9ER cells (erlotinib-resistant) was implanted in the flank of immune compromised mice. Vehicle, erlotinib (50 mg/kg/d), low-dose AZD9291 (L; 1 mg/kg/d) and high-dose AZD9291 (H; 5 mg/kg/d) were daily administrated by oral gavage, while the 3×mAbs (triple antibody combination; CTX, TRZ, 33; 0.2 mg/mouse/injection) were administrated once every three days by intraperitoneal injection. Data are means±SEM from 9 mice in each group.

FIGS. 22A-C show that the triple antibody combination sensitizes NSCLC tumors to a third generation TKI and prevents post-treatment tumor relapse. (FIG. 22A) Seven groups of mice harboring PC9ER tumor xenografts were subjected to erlotinib treatment (50 mg/kg/d) until tumors reached approximately 550 mm$^3$ size ($1^{st}$ line phase). Thereafter ($2^{nd}$ line phase), each group received one of the following treatments: erlotinib (50 mg/kg/d), 3×mAb (triple antibody combination; CTX, TRZ, 33; 0.2 mg/mouse/injection), low AZD9291 (L; 1 mg/kg/d), high AZD9291 (H; 5 mg/kg/d) or a combination of low AZD9291 (L; 1 mg/kg/d) and 3×mAb (CTX, TRZ, 33; 0.2 mg/mouse/injection) or high AZD9291 (H; 5 mg/kg/d) and 3×mAb administrated as previously described. From day 50 onward all treatments were suspended (post-treatment phase) and tumor volume was monitored. Data are means±SEM from 9-10 mice per group. (FIG. 22B) Shown are tumor volumes of the indicated groups at day 83. Data are means±SEM from 9 mice in each group. (FIG. 22C) Kaplan-Meier survival analysis of the tumor-bearing mice in presented in A. Mice were euthanized when tumor volumes reached 1500 mm$^3$.

DESCRIPTION OF SPECIFIC EMBODIMENTS OF THE INVENTION

The present invention, in some embodiments thereof, relates to compositions and methods for treating cancer resistant to a tyrosine kinase inhibitor.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

ErbB targeted therapy include a number of FDA approved drugs including cetuximab (ERBITUX®), trastuzumab (HERCEPTIN®) gefitinib (IRESSA®) and erlotinib (TARCEVA®) for the treatment of lung cancer, breast cancer, colon cancer and other types of cancer. However, while many cancer patients were found sensitive to ErbB-targeted therapy, many other patients are resistant to treatment, and even among the initially responsive patients a large percentage experience tumor recurrence and become refractory to therapy. Thus for example, despite initial dramatic response of non-small cell lung cancer (NSCLC) patients to TKIs, all patients eventually acquire resistance within approximately one year. The most common mechanism of this acquired resistance involves a specific second site mutation in the EGFR kinase domain denoted T790M or a Cysteine to Serine at position 797 (C797S).

While reducing the present invention to practice, the present inventors have uncovered that treatment of NSCLC cell lines expressing T790M mutated EGFR with erlotinib induces upregulation of other members of the ErbB family suggesting that combinations of antibodies directed at different receptors can be used to efficiently target TKI-resistant EGFRs to degradation and simultaneously block the positive feedback loop that re-activates EGFR, HER2, HER3 and the RAS-ERK pathway which leads to cell proliferation. While further reducing the present invention to practice, the present inventors have uncovered novel outstanding combinations of anti-EGRF, anti-HER2 and anti-HER3 antibodies that exerts these effects. It is therefore suggested that combinatorial treatments which employs these antibodies may be used as an important tool for combating cancer resistance to TKI. In addition, the present inventors have uncovered that a combination of anti-EGFR, anti-HER2 and anti-HER3 antibodies and a low dose of a third generation TKI which inhibits mutated EGFR while sparring wild-type EGFR e.g., AZD-9291 TKI had an improved anti-tumor effect on erlotinib resistant NSCLC tumors as compared to the triple mAb therapy or to a high dose AZD-9291 therapy. Thus, it is suggested that combinatorial treatment which employs these antibodies and TKI may be used to limit treatment adverse effects associated with such chemotherapies.

As is illustrated hereinunder and in the Examples section, which follows, the present inventors have used NSCLC cell lines expressing the EGFR T790M mutation (i.e. PC9ER and H1975) which exhibit resistance to treatment with erlotinib or cetuximab (Example 1, FIG. 1A); and showed that in-vitro long-term exposure to cetuximab or to another anti-EGFR antibody, mAb 565, results in gradual decrease in the expression levels of EGFR and up-regulation of HER2, HER3 and their active tyrosine phosphorylated forms in the treated cells (Example 1, FIG. 1B). This up-regulation was found to be at the transcriptional level (Example 1, FIGS. 1C-E and FIG. 2).

Following, superior antibodies against EGFR (565), HER2 (N12) and anti-HER3 (NG33) mAb were selected on the basis of their ability to inhibit survival of cultured NSCLC cells (Example 2, FIG. 3). In-vitro treatment with the triple mAb combination synergistically reduced protein levels of all three receptors and their downstream pathways, while retaining the ability to enhance HER2 and HER3 transcription and most importantly synergistically inhibited cell growth and survival without eliciting signs of apoptosis (Example 2, FIGS. 4, 5A-B and 6 and Example 3, FIGS. 7A-C and 8A-D). Furthermore, while the triple mAbs combination induced dose-dependent inhibition of growth in the NSCLC cell lines and possibly deprived the tumor cells from the supportive effect of the stroma, this treatment had minimal effect on two non-cancerous cell lines, suggesting that the triple mAbs treatment might spare non-cancerous tissues (Example 3, FIGS. 10, 11, 12A-C and 13A-B). In addition, treatment with the aforementioned anti-EGFR, anti-HER2 and anti-HER3 mAbs augmented the growth inhibitory effect of the chemotherapeutic drug cis-plain on both NSCLC cell lines (Example 3, FIGS. 9A-B). In addition, the present inventors have used an NSCLC cell line expressing the EGFR T790M mutation which exhibits resistance to treatment with erlotinib (i.e. PC9ER) and an NSCLC cell line expressing the EGFR T790M mutation which exhibits resistance to treatment with a third generation TKI, AZD-9291 (i.e. PC9ER-AZDR); and showed that in-vitro treatment with cetuximab (anti-EGFR), trastuzumab (anti-HER2) and mAb NG33 most potently inhibited survival of both cells lines (Example 6, FIGS. 18-19).

In accordance with the in-vitro data, the present inventors have shown that the triple mAbs combinations exerted synergistically strong and lasting inhibitory effects on tumor growth, as well as on animal survival in an in-vivo xenograft NSCLC mouse model (Example 4, FIGS. 14A-C and Example 5 FIG. 15). The effect of cetuximab, trastuzumab and mAb NG33 on tumor growth was comparable to the effect achieved by treatment with the third generation TKI, AZD-9291 (Example 5, FIGS. 16A-C). Most importantly, treatment with cetuximab, trastuzumab and mAb NG33 and a low dose AZD-9291 had an improved anti-tumor effect on erlotinib resistant NSCLC tumors as compared to the triple mAb therapy or to a high dose AZD-9291 therapy (Example 5, FIG. 17).

The present inventors further showed in animal models that the triple antibody combination can overcome resistance to AZD9291, using a proprietarily established PC9 cells resistant to the drug, the PC9ER-AZDR cells, which express the C797S mutated EGFR (FIG. 20). Despite their resistance to the drug, these cells remain sensitive to the antibody combination. The antibody combination was also shown efficacious in preventing relapse of tumors in the animal model, especially when combined with a kinase inhibitor.

The established efficacy of the antibody combinations of the present invention in the elimination, or at least reduction of tumors comprising NSCLC harboring the T790M and/or C797S mutation which renders the tumor resistant to EGFR-specific TKI therapy points to their efficacy in the treatment of tumors of similar nature.

Consequently, the present teachings suggest the use of the antibody combinations disclosed herein as an effective treatment for the treatment of cancer and especially TKI-resistant cancer.

Thus, according to an aspect of the invention, there is provided a method of treating a subject having cancer exhibiting a resistance to a tyrosine kinase inhibitor (TKI), wherein said TKI is directed to an ErbB family member and wherein cells of the cancer express said ErbB family member, the method comprising administering to the subject a therapeutically effective amount of antibodies comprising an anti-EGFR antibody, an anti-HER2 antibody and an anti-HER3 antibody, wherein:

(i) said anti-EGFR antibody comprises an antigen recognition domain having complementarity determining region (CDR) amino acid sequences as set forth in: SEQ ID NOs: 15 (CDR1), 16 (CDR2) and 17 (CDR3) (sequentially arranged from N to C on a light chain of said polypeptide) and 18 (CDR1), 19 (CDR2) and 20 (CDR3) (sequentially arranged from N to C on a heavy chain of said polypeptide) (Clone 565, CNCM-4262);

(ii) said anti-HER2 antibody comprises an antigen recognition domain having complementarity determining region (CDR) amino acid sequences as set forth in: SEQ ID NOs: 21 (CDR1), 22 (CDR2) and 23 (CDR3) (sequentially arranged from N to C on a light chain of said polypeptide) and 24 (CDR1), 25 (CDR2) and 26 (CDR3) (sequentially arranged from N to C on a heavy chain of said polypeptide) (Clone N12, CNCM-I-4112);

(iii) said anti-HER3 antibody comprises an antigen recognition domain having complementarity determining region (CDR) amino acid sequences as set forth in: SEQ ID NOs: 27 (CDR1), 28 (CDR2) and 29 (CDR3) (sequentially arranged from N to C on a light chain of said polypeptide) and 30 (CDR1), 31 (CDR2) and 32 (CDR3) (sequentially arranged from N to C on a heavy chain of said polypeptide) (Clone NG33);

(iv) said anti-EGFR antibody comprises an antigen recognition domain having complementarity determining region (CDR) amino acid sequences as set forth in: SEQ ID NOs: 15 (CDR1), 16 (CDR2) and 17 (CDR3) (sequentially arranged from N to C on a light chain of said polypeptide) and 18 (CDR1), 19 (CDR2) and 20 (CDR3) (sequentially arranged from N to C on a heavy chain of said polypeptide) (Clone 565, CNCM-4262) and said anti-HER2 antibody comprises an antigen recognition domain having complementarity determining region (CDR) amino acid sequences as set forth in: SEQ ID NOs: 21 (CDR1), 22 (CDR2) and 23 (CDR3) (sequentially arranged from N to C on a light chain of said polypeptide) and 24 (CDR1), 25 (CDR2) and 26 (CDR3) (sequentially arranged from N to C on a heavy chain of said polypeptide) (Clone N12, CNCM-I-4112);

(v) said anti-EGFR antibody comprises an antigen recognition domain having complementarity determining region (CDR) amino acid sequences as set forth in: SEQ ID NOs: 15 (CDR1), 16 (CDR2) and 17 (CDR3) (sequentially arranged from N to C on a light chain of said polypeptide) and 18 (CDR1), 19 (CDR2) and 20 (CDR3) (sequentially arranged from N to C on a heavy chain of said polypeptide) (Clone 565, CNCM-4262) and said anti-HER3 antibody comprises an antigen recognition domain having complementarity determining region (CDR) amino acid sequences as set forth in: SEQ ID NOs: 27 (CDR1), 28 (CDR2) and 29 (CDR3) (sequentially arranged from N to C on a light chain of said polypeptide) and 30 (CDR1), 31 (CDR2) and 32 (CDR3) (sequentially arranged from N to C on a heavy chain of said polypeptide) (Clone NG33);

(vi) said anti-HER2 antibody comprises an antigen recognition domain having complementarity determining region (CDR) amino acid sequences as set forth in: SEQ ID NOs: 21 (CDR1), 22 (CDR2) and 23 (CDR3) (sequentially arranged from N to C on a light chain of said polypeptide) and 24 (CDR1), 25 (CDR2) and 26 (CDR3) (sequentially arranged from N to C on a heavy chain of said polypeptide) (Clone N12, CNCM-I-4112); and said anti-HER3 antibody comprises an antigen recognition domain having complementarity determining region (CDR) amino acid sequences as set forth in: SEQ ID NOs: 27 (CDR1), 28 (CDR2) and 29 (CDR3) (sequentially arranged from N to C on a light chain of said polypeptide) and 30 (CDR1), 31 (CDR2) and 32 (CDR3) (sequentially arranged from N to C on a heavy chain of said polypeptide) (Clone NG33);

(vii) said anti-EGFR antibody comprises an antigen recognition domain having complementarity determining region (CDR) amino acid sequences as set forth in: SEQ ID NOs: 15 (CDR1), 16 (CDR2) and 17 (CDR3) (sequentially arranged from N to C on a light chain of said polypeptide) and 18 (CDR1), 19 (CDR2) and 20 (CDR3) (sequentially arranged from N to C on a heavy chain of said polypeptide) (Clone 565, CNCM-4262), said anti-HER2 antibody comprises an antigen recognition domain having complementarity determining region (CDR) amino acid sequences as set forth in: SEQ ID NOs: 21 (CDR1), 22 (CDR2) and 23 (CDR3) (sequentially arranged from N to C on a light chain of said polypeptide) and 24 (CDR1), 25 (CDR2) and 26 (CDR3) (sequentially arranged from N to C on a heavy chain of said polypeptide) (Clone N12, CNCM-I-4112); and said anti-HER3 antibody comprises an antigen recognition domain having complementarity determining region (CDR) amino acid sequences as set forth in: SEQ ID NOs: 27 (CDR1), 28 (CDR2) and 29 (CDR3) (sequentially arranged from N to C on a light chain of said polypeptide) and 30 (CDR1), 31 (CDR2) and 32 (CDR3) (sequentially arranged from N to C on a heavy chain of said polypeptide) (Clone NG33);

(viii) said anti-EGFR antibody comprises cetuximab; and said anti-HER3 antibody comprises an antigen recognition domain having complementarity determining region (CDR) amino acid sequences as set forth in: SEQ ID NOs: 27 (CDR1), 28 (CDR2) and 29 (CDR3) (sequentially arranged from N to C on a light chain of said polypeptide) and 30 (CDR1), 31 (CDR2) and 32 (CDR3) (sequentially arranged from N to C on a heavy chain of said polypeptide) (Clone NG33);

(ix) said anti-HER2 antibody comprises trastuzumab; and said anti-HER3 antibody comprises an antigen recognition domain having complementarity determining region (CDR) amino acid sequences as set forth in: SEQ ID NOs: 27 (CDR1), 28 (CDR2) and 29 (CDR3) (sequentially arranged from N to C on a light chain of said polypeptide) and 30 (CDR1), 31 (CDR2) and 32 (CDR3) (sequentially arranged from N to C on a heavy chain of said polypeptide) (Clone NG33); and/or (x) said anti-EGFR antibody comprises cetuximab, said anti-HER2 antibody comprises trastuzumab; and said anti-HER3 antibody comprises an antigen recognition domain having complementarity determining region (CDR) amino acid sequences as set forth in: SEQ ID NOs: 27 (CDR1), 28 (CDR2) and 29 (CDR3) (sequentially arranged from N to C on a light chain of said polypeptide) and 30 (CDR1), 31 (CDR2) and 32 (CDR3) (sequentially arranged from N to C on a heavy chain of said polypeptide) (Clone NG33), thereby treating the resistance to a tyrosine kinase inhibitor (TKI) of an ErbB family member in a subject.

According to another aspect of the present invention there is provided an anti-EGFR antibody, an anti-HER2 antibody and an anti-HER3 antibody for use in treating cancer resistance to a tyrosine kinase inhibitor (TKI), wherein said TKI is directed to an ErbB family member and wherein cells of the cancer express said ErbB family member, wherein:

(i) said anti-EGFR antibody comprises an antigen recognition domain having complementarity determining region (CDR) amino acid sequences as set forth in: SEQ ID NOs: 15 (CDR1), 16 (CDR2) and 17 (CDR3) (sequentially arranged from N to C on a light chain of said polypeptide) and 18 (CDR1), 19 (CDR2) and 20 (CDR3) (sequentially arranged from N to C on a heavy chain of said polypeptide) (Clone 565, CNCM-4262);

(ii) said anti-HER2 antibody comprises an antigen recognition domain having complementarity determining region (CDR) amino acid sequences as set forth in: SEQ ID NOs: 21 (CDR1), 22 (CDR2) and 23 (CDR3) (sequentially arranged from N to C on a light chain of said polypeptide) and 24 (CDR1), 25 (CDR2) and 26 (CDR3) (sequentially arranged from N to C on a heavy chain of said polypeptide) (Clone N12, CNCM-I-4112);

(iii) said anti-HER3 antibody comprises an antigen recognition domain having complementarity determining region (CDR) amino acid sequences as set forth in: SEQ ID NOs: 27 (CDR1), 28 (CDR2) and 29 (CDR3) (sequentially arranged from N to C on a light chain of said polypeptide) and 30 (CDR1), 31 (CDR2) and 32 (CDR3) (sequentially arranged from N to C on a heavy chain of said polypeptide) (Clone NG33);

(iv) said anti-EGFR antibody comprises an antigen recognition domain having complementarity determining region (CDR) amino acid sequences as set forth in: SEQ ID NOs: 15 (CDR1), 16 (CDR2) and 17 (CDR3) (sequentially arranged from N to C on a light chain of said polypeptide) and 18 (CDR1), 19 (CDR2) and 20 (CDR3) (sequentially arranged from N to C on a heavy chain of said polypeptide) (Clone 565, CNCM-4262) and said anti-HER2 antibody comprises an antigen recognition domain having complementarity determining region (CDR) amino acid sequences as set forth in: SEQ ID NOs: 21 (CDR1), 22 (CDR2) and 23 (CDR3) (sequentially arranged from N to C on a light chain of said polypeptide) and 24 (CDR1), 25 (CDR2) and 26 (CDR3) (sequentially arranged from N to C on a heavy chain of said polypeptide) (Clone N12, CNCM-I-4112);

(v) said anti-EGFR antibody comprises an antigen recognition domain having complementarity determining region (CDR) amino acid sequences as set forth in: SEQ ID NOs: 15 (CDR1), 16 (CDR2) and 17 (CDR3) (sequentially arranged from N to C on a light chain of said polypeptide) and 18 (CDR1), 19 (CDR2) and 20 (CDR3) (sequentially arranged from N to C on a heavy chain of said polypeptide) (Clone 565, CNCM-4262) and said anti-HER3 antibody comprises an antigen recognition domain having complementarity determining region (CDR) amino acid sequences as set forth in: SEQ ID NOs: 27 (CDR1), 28 (CDR2) and 29 (CDR3) (sequentially arranged from N to C on a light chain of said polypeptide) and 30 (CDR1), 31 (CDR2) and 32 (CDR3) (sequentially arranged from N to C on a heavy chain of said polypeptide) (Clone NG33);

(vi) said anti-HER2 antibody comprises an antigen recognition domain having complementarity determining region (CDR) amino acid sequences as set forth in: SEQ ID NOs: 21 (CDR1), 22 (CDR2) and 23 (CDR3) (sequentially arranged from N to C on a light chain of said polypeptide) and 24 (CDR1), 25 (CDR2) and 26 (CDR3) (sequentially arranged from N to C on a heavy chain of said polypeptide) (Clone N12, CNCM-I-4112); and said anti-HER3 antibody comprises an antigen recognition domain having complementarity determining region (CDR) amino acid sequences as set forth in: SEQ ID NOs: 27 (CDR1), 28 (CDR2) and 29 (CDR3) (sequentially arranged from N to C on a light chain of said polypeptide) and 30 (CDR1), 31 (CDR2) and 32 (CDR3) (sequentially arranged from N to C on a heavy chain of said polypeptide) (Clone NG33);

(vii) said anti-EGFR antibody comprises an antigen recognition domain having complementarity determining region (CDR) amino acid sequences as set forth in: SEQ ID NOs: 15 (CDR1), 16 (CDR2) and 17 (CDR3) (sequentially arranged from N to C on a light chain of said polypeptide) and 18 (CDR1), 19 (CDR2) and 20 (CDR3) (sequentially arranged from N to C on a heavy chain of said polypeptide) (Clone 565, CNCM-4262), said anti-HER2 antibody comprises an antigen recognition domain having complementarity determining region (CDR) amino acid sequences as set forth in: SEQ ID NOs: 21 (CDR1), 22 (CDR2) and 23 (CDR3) (sequentially arranged from N to C on a light chain of said polypeptide) and 24 (CDR1), 25 (CDR2) and 26 (CDR3) (sequentially arranged from N to C on a heavy chain of said polypeptide) (Clone N12, CNCM-I-4112); and said anti-HER3 antibody comprises an antigen recognition domain having complementarity determining region (CDR) amino acid sequences as set forth in: SEQ ID NOs: 27 (CDR1), 28 (CDR2) and 29 (CDR3) (sequentially arranged from N to C on a light chain of said polypeptide) and 30 (CDR1), 31 (CDR2) and 32 (CDR3) (sequentially arranged from N to C on a heavy chain of said polypeptide) (Clone NG33);

(viii) said anti-EGFR antibody comprises cetuximab; and said anti-HER3 antibody comprises an antigen recognition domain having complementarity determining region (CDR)

amino acid sequences as set forth in: SEQ ID NOs: 27 (CDR1), 28 (CDR2) and 29 (CDR3) (sequentially arranged from N to C on a light chain of said polypeptide) and 30 (CDR1), 31 (CDR2) and 32 (CDR3) (sequentially arranged from N to C on a heavy chain of said polypeptide) (Clone NG33);

(ix) said anti-HER2 antibody comprises trastuzumab; and said anti-HER3 antibody comprises an antigen recognition domain having complementarity determining region (CDR) amino acid sequences as set forth in: SEQ ID NOs: 27 (CDR1), 28 (CDR2) and 29 (CDR3) (sequentially arranged from N to C on a light chain of said polypeptide) and 30 (CDR1), 31 (CDR2) and 32 (CDR3) (sequentially arranged from N to C on a heavy chain of said polypeptide) (Clone NG33); and/or (x) said anti-EGFR antibody comprises cetuximab, said anti-HER2 antibody comprises trastuzumab; and said anti-HER3 antibody comprises an antigen recognition domain having complementarity determining region (CDR) amino acid sequences as set forth in: SEQ ID NOs: 27 (CDR1), 28 (CDR2) and 29 (CDR3) (sequentially arranged from N to C on a light chain of said polypeptide) and 30 (CDR1), 31 (CDR2) and 32 (CDR3) (sequentially arranged from N to C on a heavy chain of said polypeptide) (Clone NG33).

Also provided is a method of treating a subject having cancer (which is not necessarily resistant to a TKI). The method comprising administering to the subject a therapeutically effective amount of a tyrosine kinase inhibitor (TKI) and antibodies comprising an anti-EGFR antibody, an anti-HER2 antibody and an anti-HER3 antibody, wherein said), wherein said TKI is directed to an ErbB family member and wherein cells of the cancer express said ErbB family member and wherein:

(i) said anti-EGFR antibody comprises an antigen recognition domain having complementarity determining region (CDR) amino acid sequences as set forth in: SEQ ID NOs: 15 (CDR1), 16 (CDR2) and 17 (CDR3) (sequentially arranged from N to C on a light chain of said polypeptide) and 18 (CDR1), 19 (CDR2) and 20 (CDR3) (sequentially arranged from N to C on a heavy chain of said polypeptide) (Clone 565, CNCM-4262);

(ii) said anti-HER2 antibody comprises an antigen recognition domain having complementarity determining region (CDR) amino acid sequences as set forth in: SEQ ID NOs: 21 (CDR1), 22 (CDR2) and 23 (CDR3) (sequentially arranged from N to C on a light chain of said polypeptide) and 24 (CDR1), 25 (CDR2) and 26 (CDR3) (sequentially arranged from N to C on a heavy chain of said polypeptide) (Clone N12, CNCM-I-4112);

(iii) said anti-HER3 antibody comprises an antigen recognition domain having complementarity determining region (CDR) amino acid sequences as set forth in: SEQ ID NOs: 27 (CDR1), 28 (CDR2) and 29 (CDR3) (sequentially arranged from N to C on a light chain of said polypeptide) and 30 (CDR1), 31 (CDR2) and 32 (CDR3) (sequentially arranged from N to C on a heavy chain of said polypeptide) (Clone NG33);

(iv) said anti-EGFR antibody comprises an antigen recognition domain having complementarity determining region (CDR) amino acid sequences as set forth in: SEQ ID NOs: 15 (CDR1), 16 (CDR2) and 17 (CDR3) (sequentially arranged from N to C on a light chain of said polypeptide) and 18 (CDR1), 19 (CDR2) and 20 (CDR3) (sequentially arranged from N to C on a heavy chain of said polypeptide) (Clone 565, CNCM-4262) and said anti-HER2 antibody comprises an antigen recognition domain having complementarity determining region (CDR) amino acid sequences as set forth in: SEQ ID NOs: 21 (CDR1), 22 (CDR2) and 23 (CDR3) (sequentially arranged from N to C on a light chain of said polypeptide) and 24 (CDR1), 25 (CDR2) and 26 (CDR3) (sequentially arranged from N to C on a heavy chain of said polypeptide) (Clone N12, CNCM-I-4112);

(v) said anti-EGFR antibody comprises an antigen recognition domain having complementarity determining region (CDR) amino acid sequences as set forth in: SEQ ID NOs: 15 (CDR1), 16 (CDR2) and 17 (CDR3) (sequentially arranged from N to C on a light chain of said polypeptide) and 18 (CDR1), 19 (CDR2) and 20 (CDR3) (sequentially arranged from N to C on a heavy chain of said polypeptide) (Clone 565, CNCM-4262) and said anti-HER3 antibody comprises an antigen recognition domain having complementarity determining region (CDR) amino acid sequences as set forth in: SEQ ID NOs: 27 (CDR1), 28 (CDR2) and 29 (CDR3) (sequentially arranged from N to C on a light chain of said polypeptide) and 30 (CDR1), 31 (CDR2) and 32 (CDR3) (sequentially arranged from N to C on a heavy chain of said polypeptide) (Clone NG33);

(vi) said anti-HER2 antibody comprises an antigen recognition domain having complementarity determining region (CDR) amino acid sequences as set forth in: SEQ ID NOs: 21 (CDR1), 22 (CDR2) and 23 (CDR3) (sequentially arranged from N to C on a light chain of said polypeptide) and 24 (CDR1), 25 (CDR2) and 26 (CDR3) (sequentially arranged from N to C on a heavy chain of said polypeptide) (Clone N12, CNCM-I-4112); and said anti-HER3 antibody comprises an antigen recognition domain having complementarity determining region (CDR) amino acid sequences as set forth in: SEQ ID NOs: 27 (CDR1), 28 (CDR2) and 29 (CDR3) (sequentially arranged from N to C on a light chain of said polypeptide) and 30 (CDR1), 31 (CDR2) and 32 (CDR3) (sequentially arranged from N to C on a heavy chain of said polypeptide) (Clone NG33);

(vii) said anti-EGFR antibody comprises an antigen recognition domain having complementarity determining region (CDR) amino acid sequences as set forth in: SEQ ID NOs: 15 (CDR1), 16 (CDR2) and 17 (CDR3) (sequentially arranged from N to C on a light chain of said polypeptide) and 18 (CDR1), 19 (CDR2) and 20 (CDR3) (sequentially arranged from N to C on a heavy chain of said polypeptide) (Clone 565, CNCM-4262), said anti-HER2 antibody comprises an antigen recognition domain having complementarity determining region (CDR) amino acid sequences as set forth in: SEQ ID NOs: 21 (CDR1), 22 (CDR2) and 23 (CDR3) (sequentially arranged from N to C on a light chain of said polypeptide) and 24 (CDR1), 25 (CDR2) and 26 (CDR3) (sequentially arranged from N to C on a heavy chain of said polypeptide) (Clone N12, CNCM-I-4112); and said anti-HER3 antibody comprises an antigen recognition domain having complementarity determining region (CDR) amino acid sequences as set forth in: SEQ ID NOs: 27 (CDR1), 28 (CDR2) and 29 (CDR3) (sequentially arranged from N to C on a light chain of said polypeptide) and 30 (CDR1), 31 (CDR2) and 32 (CDR3) (sequentially arranged from N to C on a heavy chain of said polypeptide) (Clone NG33);

(viii) said anti-EGFR antibody comprises cetuximab; and said anti-HER3 antibody comprises an antigen recognition domain having complementarity determining region (CDR) amino acid sequences as set forth in: SEQ ID NOs: 27 (CDR1), 28 (CDR2) and 29 (CDR3) (sequentially arranged from N to C on a light chain of said polypeptide) and 30 (CDR1), 31 (CDR2) and 32 (CDR3) (sequentially arranged from N to C on a heavy chain of said polypeptide) (Clone NG33);

(ix) said anti-HER2 antibody comprises trastuzumab; and said anti-HER3 antibody comprises an antigen recognition domain having complementarity determining region (CDR) amino acid sequences as set forth in: SEQ ID NOs: 27 (CDR1), 28 (CDR2) and 29 (CDR3) (sequentially arranged from N to C on a light chain of said polypeptide) and 30 (CDR1), 31 (CDR2) and 32 (CDR3) (sequentially arranged from N to C on a heavy chain of said polypeptide) (Clone NG33); and/or (x) said anti-EGFR antibody comprises cetuximab, said anti-HER2 antibody comprises trastuzumab; and said anti-HER3 antibody comprises an antigen recognition domain having complementarity determining region (CDR) amino acid sequences as set forth in: SEQ ID NOs: 27 (CDR1), 28 (CDR2) and 29 (CDR3) (sequentially arranged from N to C on a light chain of said polypeptide) and 30 (CDR1), 31 (CDR2) and 32 (CDR3) (sequentially arranged from N to C on a heavy chain of said polypeptide) (Clone NG33), thereby treating the cancer.

As used herein the term "subject" refers to a mammal, preferably a human being at any age which suffers from the pathology.

The term "treating" refers to inhibiting or arresting the development of a pathology (disease, disorder or condition, e.g. cancer) and/or causing the reduction, remission, or regression of a pathology. Those of skill in the art will understand that various methodologies and assays can be used to assess the development of a pathology, and similarly, various methodologies and assays may be used to assess the reduction, remission or regression of a pathology.

As used herein, the terms "ErbB family member" and "ErbB receptor", which are interchangeably used herein, refer to receptors of the ErbB family of receptor tyrosine kinases E.C. 2.7.10.1 including EGFR, HER2, HER3 and HER4.

As used herein "EGF-R" refers to a receptor tyrosine kinase (RTK) of the epidermal growth factor receptor family, also referred to as HER1, mENA and ErbB-1. According to a specific embodiment the EGFR is human EGFR i.e., EGFR_HUMAN, P00533.

As used herein "HER2" refers to a receptor tyrosine kinase (RTK) of the epidermal growth factor receptor family, also referred to as ErbB-2, NEU and p185erbB-2. According to a specific embodiment the HER2 is human HER2 i.e., ERBB2_HUMAN, PO4626.

As used herein "HER3" refers to a receptor tyrosine kinase (RTK) of the epidermal growth factor receptor family, also referred to as ErbB-3. According to specific embodiments the HER3 is human HER3 i.e., ERBB3_HUMAN, P21860.

According to specific embodiments the ErbB family member is EGFR.

As used herein the term "tyrosine kinase inhibitors (TKIs)" refers to a small molecule capable of inhibiting an ErbB signaling pathway. Typically, TKIs as contemplated herein may be categorized to four groups: (1) ATP-competitive inhibitors, which bind predominantly to the ATP-binding site of the kinase when this site is in the active conformation; (2) inhibitors that recognize and bind to the non-active conformation of the ATP-binding site of the kinase, thus making activation energetically unfavorable; (3) allosteric inhibitors, that bind outside of the ATP-binding site, modifying the tridimensional structure of the receptor and disrupting the interaction between the ATP and the kinase pocket; and (4) covalent inhibitors, that bind irreversibly by covalently bonding to the ATP-binding site of the target kinase. The TKI can be specific to a specific ErbB family member or can inhibit multiple ErbB family members. The TKI can recognize wild type ErbB family member and/or a mutated ErbB family member.

Non limiting examples of TKI include erlotinib HCL (OSI-774; TARCEVA®; OSI Pharma), gefitinib (IRESSA®, AstraZeneca and Teva), lapatinib (TYKERB®, GlaxoSmithKline), canertinib (CI-1033, PD183805; Pfizer), PKI-166 (Novartis); PD158780; pelitinib; AG 1478 (4-(3-Chloroanillino)-6,7-dimethoxyquinazoline), canertinib (CI-1033, PD 183805; Pfizer) and Zactima (ZD6474), perlitinib (EKB-569), neratinib (HKI-272), vandetanib (ZD6474), afatinib, dacomitinib, AZD9291, rociletinib (CO-1686), HM61713 and WZ4002.

According to a specific embodiment, the TKI is a pan-ErbB inhibitor, i.e., capable of binding and inhibiting the kinase activity of more than one ErbB family member, such as lapatinib.

According to specific embodiments the TKI is specific to a single ErbB family member. i.e., does not affect other members in the ErbB family such as an EGFR-specific TKI.

According to specific embodiments the TKI is selected from the group consisting of erlotinib, gefitinib and lapatinib.

According to a specific embodiment the TKI is erlotinib.

According to specific embodiments, the TKI is an irreversible TKI. Non-limiting examples of irreversible TKIs include perlitinib (EKB-569), neratinib (HKI-272), canertinib (CI-1033), vandetanib (ZD6474), afatinib and dacomitinib.

According to specific embodiments, the irreversible TKI is typically used when the cancer exhibits resistance to a reversible first generation TKI such as erlotinib, gefitinib and lapatinib.

According to specific embodiments, the TKI binds an ErbB receptor having a mutation in a kinase domain of said receptor. Examples of ErbB receptor mutations such as the T790M are further disclosed hereinbelow. Non-limiting examples of TKIs that bind and inhibit mutated ErbB receptor include WZ4002, AZD9291, rociletinib (CO-1686) and HM61713 that binds and inhibits mutated EGF-R. According to specific embodiments the TKI does not bind a wild-type ErbB receptor (e.g. EGF-R).

According to specific embodiments, the TKI is selected from the group consisting of perlitinib (EKB-569), neratinib (HKI-272), canertinib (CI-1033), vandetanib (ZD6474), afatinib, dacomitinib, AZD9291, rociletinib (CO-1686), HM61713 and WZ4002.

According to specific embodiments, the TKI is AZD9291.

According to specific embodiments the method further comprising administering the TKI to the subject. According to specific embodiments, the TKI is the same TKI which the cancer exhibits resistance to.

According to other specific embodiments, the TKI is a TKI which the cancer exhibits sensitivity to (i.e. an additional TKI which is different from the TKI which the cancer exhibits resistance to). The additional TKI can inhibit the same ErbB family member(s) or another ErbB family member(s) targeted by the TKI the cancer exhibits resistance to.

Administration can be effected concomitantly with administration of the antibodies or following administration of the antibodies.

The TKI may be administered at a gold standard dosing as a single agent, below a gold standard dosing as a single agent or above a gold standard dosing as a single agent.

According to specific embodiments, the TKI is administered below gold standard dosing as a single agent.

As used herein the term "gold standard dosing" refers to the dosing which is recommended by a regulatory agency (e.g., FDA), for a given tumor at a given stage.

According to other specific embodiments the TKI is administered at a dose that does not exert at least one side effect which is associated with the gold standard dosing. Non-limiting examples of side effects of a TKI treatment include skin rash, diarrhea, mouth sores, paronychia, fatigue, hyperglycemia, hepatotoxicity, kidney failure, cardiovascular effects, electrolytes anomalies and GI perforations. As shown in the Examples section which follows the present inventors have shown that treatment with anti-EGF-R, anti-HER2 and anti-HER3 antibodies in combination with low dose AZD-9291 TKI had an improved anti-tumor effect on erlotinib resistant NSCLC tumors as compared to the triple mAb therapy or to a high dose AZD-9291 therapy. Thus, the present invention further contemplates a combined treatment comprising anti-EGF-R, anti-HER2 and anti-HER3 antibodies and TKI.

According to an aspect of the present invention there is provided a method of treating a subject having cancer exhibiting a resistance to a tyrosine kinase inhibitor (TKI), wherein said TKI is directed to an ErbB family member and wherein cells of the cancer express said ErbB family member, the method comprising administering to the subject a therapeutically effective amount of an additional TKI and a therapeutically effective amount of at least one antibody specifically binding EGFR, HER2 and HER3, wherein said additional TKI is different from said TKI and wherein said cancer does not exhibit resistance to said additional TKI.

According to another aspect of the present invention there is provided a tyrosine kinase inhibitor (TKI) and at least one antibody specifically binding EGFR, HER2 and HER3 for use in treating cancer resistance to a TKI, wherein said TKI is directed to an ErbB family member and wherein cells of the cancer express said ErbB family member and wherein said TKI is different from said TKI to which said cancer is resistant.

As used herein the term "at least one antibody" refers to at least one, at least two or at least three antibodies. The antibody may comprise a mono-specific antibody and/or a multi-specific antibody as further disclosed hereinbelow. The at least one antibody may be to a single target or to a plurality of targets.

Thus, according to these aspects of the present invention, "a composition of antibodies" refers to three distinct antibodies, wherein essentially one antibody binds specifically to EGFR, the second antibody binds specifically to HER2 and the third antibody binds specifically to HER3; as well as to multi-specific antibodies, wherein one antibody binds a plurality of targets (e.g. EGFR+HER2, EGFR+HER3, HER2+HER3, EGFR+HER2+HER3).

According to specific embodiments, the at least one antibody comprises an anti-EGFR antibody, an anti-HER2 antibody and an anti-HER3 antibody, wherein:

(i) said anti-EGFR antibody comprises an antigen recognition domain having complementarity determining region (CDR) amino acid sequences as set forth in: SEQ ID NOs: 15 (CDR1), 16 (CDR2) and 17 (CDR3) (sequentially arranged from N to C on a light chain of said polypeptide) and 18 (CDR1), 19 (CDR2) and 20 (CDR3) (sequentially arranged from N to C on a heavy chain of said polypeptide) (Clone 565, CNCM-4262);

(ii) said anti-HER2 antibody comprises an antigen recognition domain having complementarity determining region (CDR) amino acid sequences as set forth in: SEQ ID NOs: 21 (CDR1), 22 (CDR2) and 23 (CDR3) (sequentially arranged from N to C on a light chain of said polypeptide) and 24 (CDR1), 25 (CDR2) and 26 (CDR3) (sequentially arranged from N to C on a heavy chain of said polypeptide) (Clone N12, CNCM-I-4112);

(iii) said anti-HER3 antibody comprises an antigen recognition domain having complementarity determining region (CDR) amino acid sequences as set forth in: SEQ ID NOs: 27 (CDR1), 28 (CDR2) and 29 (CDR3) (sequentially arranged from N to C on a light chain of said polypeptide) and 30 (CDR1), 31 (CDR2) and 32 (CDR3) (sequentially arranged from N to C on a heavy chain of said polypeptide) (Clone NG33);

(iv) said anti-EGFR antibody comprises an antigen recognition domain having complementarity determining region (CDR) amino acid sequences as set forth in: SEQ ID NOs: 15 (CDR1), 16 (CDR2) and 17 (CDR3) (sequentially arranged from N to C on a light chain of said polypeptide) and 18 (CDR1), 19 (CDR2) and 20 (CDR3) (sequentially arranged from N to C on a heavy chain of said polypeptide) (Clone 565, CNCM-4262) and said anti-HER2 antibody comprises an antigen recognition domain having complementarity determining region (CDR) amino acid sequences as set forth in: SEQ ID NOs: 21 (CDR1), 22 (CDR2) and 23 (CDR3) (sequentially arranged from N to C on a light chain of said polypeptide) and 24 (CDR1), 25 (CDR2) and 26 (CDR3) (sequentially arranged from N to C on a heavy chain of said polypeptide) (Clone N12, CNCM-I-4112);

(v) said anti-EGFR antibody comprises an antigen recognition domain having complementarity determining region (CDR) amino acid sequences as set forth in: SEQ ID NOs: 15 (CDR1), 16 (CDR2) and 17 (CDR3) (sequentially arranged from N to C on a light chain of said polypeptide) and 18 (CDR1), 19 (CDR2) and 20 (CDR3) (sequentially arranged from N to C on a heavy chain of said polypeptide) (Clone 565, CNCM-4262) and said anti-HER3 antibody comprises an antigen recognition domain having complementarity determining region (CDR) amino acid sequences as set forth in: SEQ ID NOs: 27 (CDR1), 28 (CDR2) and 29 (CDR3) (sequentially arranged from N to C on a light chain of said polypeptide) and 30 (CDR1), 31 (CDR2) and 32 (CDR3) (sequentially arranged from N to C on a heavy chain of said polypeptide) (Clone NG33);

(vi) said anti-HER2 antibody comprises an antigen recognition domain having complementarity determining region (CDR) amino acid sequences as set forth in: SEQ ID NOs: 21 (CDR1), 22 (CDR2) and 23 (CDR3) (sequentially arranged from N to C on a light chain of said polypeptide) and 24 (CDR1), 25 (CDR2) and 26 (CDR3) (sequentially arranged from N to C on a heavy chain of said polypeptide) (Clone N12, CNCM-I-4112); and said anti-HER3 antibody comprises an antigen recognition domain having complementarity determining region (CDR) amino acid sequences as set forth in: SEQ ID NOs: 27 (CDR1), 28 (CDR2) and 29 (CDR3) (sequentially arranged from N to C on a light chain of said polypeptide) and 30 (CDR1), 31 (CDR2) and 32 (CDR3) (sequentially arranged from N to C on a heavy chain of said polypeptide) (Clone NG33);

(vii) said anti-EGFR antibody comprises an antigen recognition domain having complementarity determining region (CDR) amino acid sequences as set forth in: SEQ ID NOs: 15 (CDR1), 16 (CDR2) and 17 (CDR3) (sequentially arranged from N to C on a light chain of said polypeptide) and 18 (CDR1), 19 (CDR2) and 20 (CDR3) (sequentially arranged from N to C on a heavy chain of said polypeptide) (Clone 565, CNCM-4262), said anti-HER2 antibody comprises an antigen recognition domain having complementarity determining region (CDR) amino acid sequences as set forth in: SEQ ID NOs: 21 (CDR1), 22 (CDR2) and 23 (CDR3) (sequentially arranged from N to C on a light chain of said polypeptide) and 24 (CDR1), 25 (CDR2) and 26 (CDR3) (sequentially arranged from N to C on a heavy chain of said polypeptide) (Clone N12, CNCM-I-4112); and said anti-HER3 antibody comprises an antigen recognition domain having complementarity determining region (CDR) amino acid sequences as set forth in: SEQ ID NOs: 27 (CDR1), 28 (CDR2) and 29 (CDR3) (sequentially arranged from N to C on a light chain of said polypeptide) and 30 (CDR1), 31 (CDR2) and 32 (CDR3) (sequentially arranged from N to C on a heavy chain of said polypeptide) (Clone NG33);

(viii) said anti-EGFR antibody comprises cetuximab; and said anti-HER3 antibody comprises an antigen recognition domain having complementarity determining region (CDR) amino acid sequences as set forth in: SEQ ID NOs: 27 (CDR1), 28 (CDR2) and 29 (CDR3) (sequentially arranged from N to C on a light chain of said polypeptide) and 30 (CDR1), 31 (CDR2) and 32 (CDR3) (sequentially arranged from N to C on a heavy chain of said polypeptide) (Clone NG33);

(ix) said anti-HER2 antibody comprises trastuzumab; and said anti-HER3 antibody comprises an antigen recognition domain having complementarity determining region (CDR) amino acid sequences as set forth in: SEQ ID NOs: 27 (CDR1), 28 (CDR2) and 29 (CDR3) (sequentially arranged from N to C on a light chain of said polypeptide) and 30 (CDR1), 31 (CDR2) and 32 (CDR3) (sequentially arranged from N to C on a heavy chain of said polypeptide) (Clone NG33); and/or (x) said anti-EGFR antibody comprises cetuximab, said anti-HER2 antibody comprises trastuzumab; and said anti-HER3 antibody comprises an antigen recognition domain having complementarity determining region (CDR) amino acid sequences as set forth in: SEQ ID NOs: 27 (CDR1), 28 (CDR2) and 29 (CDR3) (sequentially arranged from N to C on a light chain of said polypeptide) and 30 (CDR1), 31 (CDR2) and 32 (CDR3) (sequentially arranged from N to C on a heavy chain of said polypeptide) (Clone NG33).

As used herein the term "cancer" refers to a tumoral disease which depends on ErbB (activity and/or expression) for onset and/or progression. Thus, the cancer cells express an ErbB polypeptide which facilitates disease progression.

Examples of cancer which can be treated in accordance with the present teachings include, but are not limited to invasive breast carcinoma, adenocarcinoma, lung cancer (non-small cell, squamous cell carcinoma, adenocarcinoma, and large cell lung cancer), liver cancer, colorectal cancer, brain, head and neck cancer (e.g., neuro/glioblastoma), breast cancer, ovarian cancer, transitional cell carcinoma of the bladder, prostate cancer, oral squamous cell carcinoma, bone sarcoma, adrenocortical cancer, gastrointestinal tumors including colorectal cancer, biliary tract cancer such as gallbladder carcinoma (GBC), bladder cancer, esophageal cancer, gastric cancer, cervical cancer, salivary gland cancer, diarrhea benign neoplasm, ductal carcinoma in situ, paronychia, cholangiocarcinoma, kidney cancer, pancreatic cancer, medulloblastoma, glioblastoma, luminal, HER2-positive and triple negative mammary tumors and viral leukemia.

According to a specific embodiment the cancer is lung cancer.

According to specific embodiments the lung cancer is non-small cell lung cancer (NSCLC).

As used herein, the phrase "resistance to a tyrosine kinase inhibitor (TKI)" refers to non-responsiveness to TKI treatment as may be manifested by tumor size, in-vitro activity assays and/or patient survival.

According to a specific embodiment, resistance refers to no amelioration in disease symptoms or progression according to a regulatory agency guidelines (e.g., FDA) for the specific TKI used. Resistance to treatment can be primary resistance or acquired resistance.

According to specific embodiments the resistance is an acquired resistance.

As used herein the term "acquired resistance" refers to progression of resistance following initial positive response to therapy.

According to specific embodiments the patient further exhibits resistance to an anti-ErbB monoclonal such as but not limited to anti-EGFR (e.g. cetuximab).

The main known molecular mechanism of acquired resistance to TKIs include mutations in the e.g. EGFR kinase domain, including T790M; gene amplification, such as MET, leading to overproduction of the TK; over-expression of RTK ligands that mediates uncontrolled tumor cells activation; modification of signaling pathways, such as PTEN instability that mediates constitutive Akt activation; and increased efflux or decreased influx of TKIs from the cancer cell, mediated by membrane transporters such as MDR1 or hOCT1 [see e.g. Chen and Fu, Acta Pharmaceutica Sinica B, (2011) 1(4): 197-207].

Thus, according to a specific embodiment, the cancer cells express an ErbB receptor having a mutation in a kinase domain of said receptor.

Methods of analyzing sequence alterations such as in the kinase domain of an ErbB are well known in the art, basically including analysis (e.g., by PCR and sequencing) of genomic DNA, or cDNA encoding the ErbB using a biological sample obtained from the subject exhibiting the resistance (e.g., biopsy). Analysis at the polypeptide level can also be done such as using antibodies which specifically recognize the mutated form of the protein and not the wild-type form. Analysis at the protein level can also be done by an activity assay as further described hereinbelow.

Such biological samples include, but are not limited to, body fluids such as whole blood, serum, plasma, cerebrospinal fluid, urine, lymph fluids, and various external secretions of the respiratory, intestinal and genitourinary tracts, tears, saliva, milk as well as white blood cells, malignant tissues, amniotic fluid and chorionic villi.

According to one embodiment the sample comprises a fluid, such as for example, blood, plasma, saliva etc.

The sample may comprise cells including, but not limited to blood cells, bone marrow cells, pancreatic cells, lung cells, hepatic cells, spleen cells, kidney cells, cardiac cells, ovarian cells, breast tissue cells, skin cells (e.g., epithelial cells, fibroblasts, keratinocytes), lymph node cells.

According to a particular embodiment the cells comprise cancer cells. Such cells can be obtained using methods known in the art, including, but not limited to, fine needle biopsy, needle biopsy, core needle biopsy and surgical biopsy (e.g., lung biopsy), buccal smear and lavage.

Mutations in the kinase domain of the receptor may alter the kinase activity.

According to specific embodiments, the mutation does not substantially affect a kinase activity of said ErbB.

As used herein, the term "substantially affect" refers to an un-altered kinase activity (+/−10%, or 20%) in the presence of absence of the mutation.

Determining the kinase activity can be achieved using methods well known in the art, such as Western-blot and in-vitro kinase assay.

Non limiting examples of mutations in a kinase domain of an ErbB include the following EGFR mutations: G719C, G719S, L858R, L861Q, T790M, C797S and an exon 20 insertion; and the T798M mutation in HER2.

According to specific embodiments the mutation comprises the T790M mutation or a Cysteine to Serine at position 797 (C797S).

As used herein, the term "T790M" refers to a substitution of Threonine to Methionine at position 790 (T790M) in the EGFR kinase domain. This substitution was shown to preserve (i.e., not substantially affect) the kinase activity of the receptor.

As used herein "a composition of antibodies" refers to three distinct antibodies, having different CDR sequences comprising antibodies directed to distinct receptors, i.e. EGFR, HER2 and HER3, essentially one antibody binds specifically to EGFR, the second antibody binds specifically to HER2 and the third antibody binds specifically to HER3.

According to specific embodiments, the anti-EGFR antibody does not bind HER2 and HER3 in a clinically relevant affinity i.e., $K_D$ below 50 nM.

According to specific embodiments, the anti-HER2 antibody does not bind EGFR and HER3 in a clinically relevant affinity i.e., $K_D$ below 50 nM.

According to specific embodiments, the anti-HER3 antibody does not bind EGFR and HER2 in a clinically relevant affinity i.e., $K_D$ below 50 nM.

Methods of assaying antibody specificity are well known in the art, such as for example, ELISA, Western blot, BIAcore and cross-competition.

Antibodies of the present invention may bind the EGFR, HER2 and/or HER3 with similar or different affinities. According to specific embodiments the antibodies bind the target EGFR, HER2 and/or HER3 with a minimal affinity of at least 100 nM, 50 nM, 10 nM, 1 nM or higher.

The antibodies can be selected from pre-existing antibodies (e.g., publicly available hybridomas or recombinant antibody libraries, further described hereinbelow) or from newly generated antibodies produced according to methods which are well-known in the art and further described hereinbelow.

Antibodies and methods of generating same are described at length in the following sections.

Anti-EGFR 565, anti-HER2 N12 have been deposited in the Collection Nationale de Cultures de Microorganismes Institut Pasteur 25. Rue du Docteur Roux F-75724 Paris CEDEX 15. Antibodies have been deposited under the Budapest Treaty on the International Recognition of the Deposit of Microorganisms for the Purposes of Patent Procedure, and comply with the criteria set forth in 37 CFR § 1.801-1.809 regarding availability and permanency of deposits.

The registration numbers are as follows:

565 CNCM 1-4262, received for deposit on Nov. 26, 2009; and

N12 CNCM 1-4112, received for deposit on Jan. 13, 2009.

The CDRs of anti-EGFR 565 extracted from the VH amino acid sequence QVQLQQSGAELVKPGAS-VKLSCKASGYTFTNYWIHWVKQRPGQGLEWIGEIGP INGRSNYIEKFKTKATLTVDKSSSTTYLHLSSLTSED-SAVYYCAREDDYDGKAM DYWGQGTSVTVSS (SEQ ID NO: 1); and the Vkappa amino acid sequence DIVMTQSHKFXSTSVGDRVSITCKASQNVGTAVAWY-QQKPGQSPKLLIYWTST RHTGVPDRFTGTGS-GTEFTLTINNVQSEDLADYFCQQYSGYSFGGGT-KLELKR (SEQ ID NO: 2) comprise CDR1 (SEQ ID NO: 15), CDR2 (SEQ ID NO: 16) and CDR3 (SEQ ID NO: 17) (sequentially arranged from N to C on the light chain of the polypeptide) and CDR1 (SEQ ID NO: 18), CDR2 (SEQ ID NO: 19) and CDR3 (SEQ ID NO: 20) (sequentially arranged from N to C on the heavy chain of the polypeptide).

The CDRs of anti-HER2 N12 (also referred to herein as 12) extracted from the VH amino acid Sequence QVQLQQSGAELVRPGDSVNLSCKASGYTFTSYWMY-WIKQRPDQGLESIGNIHP NNGGTNYSGKFKNKASLT-VDKSSTTAYMQLSSLTSEDSAVYFCARLTGIGMDY WGQGTSVIVSS (SEQ ID NO: 3); and the Vkappa amino acid sequence DIVMTQSHKFMSTSVGDRVSITCK-ASQNVGTAVAWYQQKPGQSPKLLIYWTST RHTGVP-DRFTGTGSGTEFTLTINNVQSEDLADYFCQQYSGYS-FGGGTRLEIKL (SEQ ID NO: 4) comprise CDR1 (SEQ ID NO: 21), CDR2 (SEQ ID NO: 22) and CDR3 (SEQ ID NO: 23) (sequentially arranged from N to C on the light chain of the polypeptide) and CDR1 (SEQ ID NO: 24), CDR2 (SEQ ID NO: 25) and CDR3 (SEQ ID NO: 26) (sequentially arranged from N to C on the heavy chain of the polypeptide).

The CDRs of anti-HER3 NG33 (also referred to herein as 33) extracted from the VH amino acid sequence DVQLQESGPGLVKPSQSLSLTCSVTGYSITSGFY-WSWIRQFPGNKLEWMGYIAY DGTSNYNPSLKNRISI-TRDTSKNQFFLKLKSVTNEDTPTYY-CARGGGYYGQLLD YWGQGTSVTVSS (SEQ ID NO: 5); and the Vkappa amino acid sequence DARMTQSPSSLSASLGDRVTISCRASQDISNYLNWY-QQKPDGTVKVLIYNTAKL HSGVPSRFSGSGSGTDYS-LTISNLEQEDFATYFCQQGKTLPWTFGGGTKLELK (SEQ ID NO: 6) comprise CDR1 (SEQ ID NO: 27), CDR2 (SEQ ID NO: 28) and CDR3 (SEQ ID NO: 29) (sequentially arranged from N to C on the light chain of the polypeptide) and CDR1 (SEQ ID NO: 30), CDR2 (SEQ ID NO: 31) and CDR3 (SEQ ID NO: 32) (sequentially arranged from N to C on the heavy chain of the polypeptide).

As used herein the term "cetuximab", trademarked as ERBITUX®, refers to an immunotherapy drug that contains the active ingredient cetuximab, an anti-EGF-R monoclonal antibody.

As used herein the term "Trastuzumab", trademarked as HERCELON or HERCEPTIN®, refers to an immunotherapy drug that contains the active ingredient Trastuzumab, an anti-HER2 monoclonal antibody."

The term "antibody" as used herein includes intact molecules as well as functional fragments thereof, such as Fab, F(ab')2, and Fv that are capable of binding to macrophages. These functional antibody fragments are defined as follows: (1) Fab, the fragment which contains a monovalent antigen-binding fragment of an antibody molecule, can be produced by digestion of whole antibody with the enzyme papain to yield an intact light chain and a portion of one heavy chain; (2) Fab', the fragment of an antibody molecule that can be obtained by treating whole antibody with pepsin, followed by reduction, to yield an intact light chain and a portion of the heavy chain; two Fab' fragments are obtained per antibody molecule; (3) (Fab')2, the fragment of the antibody that can be obtained by treating whole antibody with the enzyme pepsin without subsequent reduction; F(ab')2 is a dimer of two Fab' fragments held together by two disulfide bonds; (4) Fv, defined as a genetically engineered fragment containing the variable region of the light chain and the variable region of the heavy chain expressed as two chains; and (5) Single chain antibody ("SCA"), a genetically engineered molecule containing the variable region of the light chain and the variable region of the heavy chain, linked by a suitable polypeptide linker as a genetically fused single chain molecule.

As used herein, the terms "complementarity-determining region" or "CDR" are used interchangeably to refer to the antigen binding regions found within the variable region of the heavy and light chain polypeptides. Generally, antibodies comprise three CDRs in each of the VH (CDR HI or HI; CDR H2 or H2; and CDR H3 or H3) and three in each of the VL (CDR LI or LI; CDR L2 or L2; and CDR L3 or L3).

The identity of the amino acid residues in a particular antibody that make up a variable region or a CDR can be determined using methods well known in the art and include methods such as sequence variability as defined by Kabat et al. (See, e.g., Kabat et al., 1992, Sequences of Proteins of Immunological Interest, 5th ed., Public Health Service, NIH, Washington D.C.), location of the structural loop regions as defined by Chothia et al. (see, e.g., Chothia et al., Nature 342:877-883, 1989.), a compromise between Kabat and Chothia using Oxford Molecular's AbM antibody modeling software (now Accelrys®, see, Martin et al., 1989, Proc. Natl Acad Sci USA. 86:9268; and world wide web site www(dot)bioinf-org(dot)uk/abs), available complex crystal structures as defined by the contact definition (see MacCallum et al., J. Mol. Biol. 262:732-745, 1996) and the "conformational definition" (see, e.g., Makabe et al., Journal of Biological Chemistry, 283:1156-1166, 2008).

As used herein, the "variable regions" and "CDRs" may refer to variable regions and CDRs defined by any approach known in the art, including combinations of approaches.

According to a specific embodiment, the "variable regions" and "CDRs" refer to variable regions and CDRs defined by the IMGT approach.

Methods of producing polyclonal and monoclonal antibodies as well as fragments thereof are well known in the art (See for example, Harlow and Lane, Antibodies: A Laboratory Manual, Cold Spring Harbor Laboratory, New York, 1988, incorporated herein by reference).

According to specific embodiments the antibody is a recombinant antibody.

As used herein, the term "recombinant antibody" refers an antibody produced by recombinant DNA techniques, i.e., produced from cells transformed by an exogenous DNA construct encoding the antibody.

According to specific embodiments the antibody is a monoclonal antibody.

In cases where target antigens are too small to elicit an adequate immunogenic response when generating antibodies in vivo, such antigens (referred to as "haptens") can be coupled to antigenically neutral carriers such as keyhole limpet hemocyanin (KLH) or serum albumin (e.g., bovine serum albumin (BSA)) carriers (see, for example, U.S. Pat. Nos. 5,189,178 and 5,239,078). Coupling a hapten to a carrier can be effected using methods well known in the art. For example, direct coupling to amino groups can be effected and optionally followed by reduction of the imino linkage formed. Alternatively, the carrier can be coupled using condensing agents such as dicyclohexyl carbodiimide or other carbodiimide dehydrating agents. Linker compounds can also be used to effect the coupling; both homobifunctional and heterobifunctional linkers are available from Pierce Chemical Company, Rockford, Ill., USA. The resulting immunogenic complex can then be injected into suitable mammalian subjects such as mice, rabbits, and others. Suitable protocols involve repeated injection of the immunogen in the presence of adjuvants according to a schedule designed to boost production of antibodies in the serum. The titers of the immune serum can readily be measured using immunoassay procedures which are well known in the art.

The antisera obtained can be used directly or monoclonal antibodies may be obtained, as described hereinabove. Antibody fragments according to some embodiments of the invention can be prepared by proteolytic hydrolysis of the antibody or by expression in E. coli or mammalian cells (e.g. Chinese hamster ovary cell culture or other protein expression systems) of DNA encoding the fragment.

Antibody fragments can be obtained by pepsin or papain digestion of whole antibodies by conventional methods. For example, antibody fragments can be produced by enzymatic cleavage of antibodies with pepsin to provide a 5S fragment denoted F(ab')2. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, by Goldenberg, U.S. Pat. Nos. 4,036,945 and 4,331,647, and references contained therein, which patents are hereby incorporated by reference in their entirety. See also Porter, R. R. [Biochem. J. 73: 119-126 (1959)]. Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

Fv fragments comprise an association of VH and VL chains. This association may be noncovalent, as described in Inbar et al. [Proc. Nat'l Acad. Sci. USA 69:2659-62 (19720]. Alternatively, the variable chains can be linked by an intermolecular disulfide bond or cross-linked by chemicals such as glutaraldehyde. Preferably, the Fv fragments comprise VH and VL chains connected by a peptide linker. These single-chain antigen binding proteins (sFv) are prepared by constructing a structural gene comprising DNA sequences encoding the VH and VL domains connected by an oligonucleotide. The structural gene is inserted into an expression vector, which is subsequently introduced into a host cell such as E. coli. The recombinant host cells synthesize a single polypeptide chain with a linker peptide bridging the two V domains. Methods for producing sFvs are described, for example, by [Whitlow and Filpula, Methods 2: 97-105 (1991); Bird et al., Science 242:423-426 (1988); Pack et al., Bio/Technology 11:1271-77 (1993); and U.S. Pat. No. 4,946,778, which is hereby incorporated by reference in its entirety.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick and Fry [Methods, 2: 106-10 (1991)].

Thus, antibodies of the present invention are preferably at least bivalent (e.g., of the IgG subtype) or more (e.g., of the IgM subtype). It will be appreciated that monovalent antibodies may be used however measures should be taken to assemble these to larger complexes such as by using secondary antibodies (or using other cross-linkers which are well known in the art). According to specific embodiments the antibodies are from IgG1 subtype.

According to specific embodiments antibody is a humanized or partially humanized antibody.

Humanized forms of non-human (e.g., murine) antibodies are chimeric molecules of immunoglobulins, immunoglobulin chains or fragments thereof (such as Fv, Fab, Fab', F(ab').sub.2 or other antigen-binding subsequences of antibodies) which contain minimal sequence derived from non-human immunoglobulin. Humanized antibodies include human immunoglobulins (recipient antibody) in which residues form a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., Nature, 321:522-525 (1986); Riechmann et al., Nature, 332:323-329 (1988); and Presta, Curr. Op. Struct. Biol., 2:593-596 (1992)].

Methods for humanizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers [Jones et al., Nature, 321:522-525 (1986); Riechmann et al., Nature 332:323-327 (1988); Verhoeyen et al., Science, 239:1534-1536 (1988)], by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, J. Mol. Biol., 227:381 (1991); Marks et al., J. Mol. Biol., 222:581 (1991)]. The techniques of Cole et al. and Boerner et al. are also available for the preparation of human monoclonal antibodies (Cole et al., Monoclonal Antibodies and Cancer Therapy, Alan R. Liss, p. 77 (1985) and Boerner et al., J. Immunol., 147(1):86-95 (1991)]. Similarly, human antibodies can be made by introduction of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., Bio/Technology 10: 779-783 (1992); Lonberg et al., Nature 368: 856-859 (1994); Morrison, Nature 368 812-13 (1994); Fishwild et al., Nature Biotechnology 14, 845-51 (1996); Neuberger, Nature Biotechnology 14: 826 (1996); and Lonberg and Huszar, Intern. Rev. Immunol. 13: 65-93 (1995).

The antibodies can be mono-specific (i.e., binding a distinct antigen) or multi-specific (i.e. binding at least two different epitopes, e.g., bi-specific or tri-specific).

According to specific embodiments, the antibody is a mono-specific antibody.

According to specific embodiments, the antibody is bi-specific antibody.

According to specific embodiments, the antibody is a tri-specific antibody.

According to other specific embodiments, the antibody is a multi-specific antibody.

Thus, the at least one antibody may include a single tri-specific molecule specifically binding EGFR, HER2 and HER3; a bi-specific molecule specifically binding two of the three ErbB family members e.g., EGFR+HER2, EGFR+HER3, HER2+HER3; and/or a mono-specific antibody i.e. anti-EGFR, anti-HER2, anti-HER3.

Thus, the combination of antibodies may include a single tri-specific molecule which comprises the CDRs of N12, 565 and NG33 or cetuximab, trastuzumab and NG33; a bi-specific configuration with a mono-specific antibody e.g., N12+565 and NG33; N12+NG33 and 565, NG33+565 and N12; or the administration of 3 mono-specific antibodies i.e., NG33, N12 and 565 or cetuximab, trastuzumab and NG33.

Multi-specific antibodies can be produced by many methods known in the art such as those disclosed in U.S. Pat. Nos. 4,474,893, 5,959,084, and 7,235,641, 7,183,076, U.S. Publication Number 20080219980 and International Publication Numbers WO 2010/115589, WO2013150043 and WO2012118903 all incorporated herein by their entirety; and include, for example, chemical cross-linking (Brennan, et al., Science 229,81 (1985); Raso, et al., J. Biol. Chem. 272, 27623 (1997)), disulfide exchange, production of hybrid-hybridomas (quadromas), by transcription and translation to produce a single polypeptide chain embodying a bi-specific antibody, or by transcription and translation to produce more than one polypeptide chain that can associate covalently to produce a bi-specific antibody.

After antibodies have been obtained, they may be tested for activity, for example via enzyme-linked immunosorbent assay (ELISA).

According to specific embodiments the combination of antibodies of the present invention is identified as capable of down-regulating the protein expression levels of EGFR, HER2, HER3, their active tyrosine phosphorylated forms and their downstream pathway (e.g. ERK) in a cell (e.g., mammalian cell) expressing same.

Downregulation of protein expression levels may be for example by at least 10%, 20%, 50%, 80%, 90% or 100% in comparison to protein expression in the same cell before treatment; a cell of the same origin but not treated or treated with an irrelevant control e.g. vehicle, PBS as detected by e.g. Western blot, immunocytochemistry and flow cytometry.

As used herein the phrase "anti-tumor activity" refers to prevention of tumor formation and/or reduction of tumor size (e.g., volume) and/or metastasis potential.

The combination of antibodies and the combination of TKI and antibody(ies) described herein have combined improved anti tumor activity. As used herein the phrase "combined improved anti tumor activity" refers to at least additive but preferably synergistically improved anti tumor activity as explained hereinabove.

Without being bound by theory it is suggested that synergistic effect of the combination of antibodies of the present invention is dependent on the size of antibody-receptor lattices formed at the cell-surface, which dictates the rate of endocytic clearance and extent of signaling blockade.

According to specific embodiments the antibodies are selected causing at least 40% or 50% (e.g., 60% or 70% or higher) reduction in in-vitro tumor cells growth and/or survival in comparison to tumor cells of the same origin that were not treated or treated with irrelevant control e.g. PBS, vehicle.

According to specific embodiments the antibodies are selected causing at least 50% reduction in tumor volume as compared to a control in a xenograft mouse model.

As used herein the control may be a xenograft mouse model of the same type that was not treated or treated with irrelevant control e.g. PBS, vehicle.

Determining tumor volume in a xenograft mouse model may be effected following 1 month, 2 months, 3 months, 4 months, 6 months, 1 year or 2 years following treatment initiation.

According to specific embodiments the antibodies are selected synergistic with a chemotherapy.

Antibodies and/or TKIs of the present invention can be administered to an organism per se, or in a pharmaceutical composition where they are mixed with suitable carriers or excipients (either individually or in a co-formulation).

Thus, according to another aspect of the present invention there is provided a pharmaceutical composition comprising as active ingredients an anti-EGFR antibody, an anti-HER2 antibody and an anti-HER3 antibody and a pharmaceutically acceptable carrier or diluents, wherein:

(i) said anti-HER3 antibody comprises an antigen recognition domain having complementarity determining region (CDR) amino acid sequences as set forth in: SEQ ID NOs: 27 (CDR1), 28 (CDR2) and 29 (CDR3) (sequentially arranged from N to C on a light chain of said polypeptide) and 30 (CDR1), 31 (CDR2) and 32 (CDR3) (sequentially arranged from N to C on a heavy chain of said polypeptide) (Clone NG33);

(ii) said anti-EGFR antibody comprises an antigen recognition domain having complementarity determining region (CDR) amino acid sequences as set forth in: SEQ ID NOs: 15 (CDR1), 16 (CDR2) and 17 (CDR3) (sequentially arranged from N to C on a light chain of said polypeptide) and 18 (CDR1), 19 (CDR2) and 20 (CDR3) (sequentially arranged from N to C on a heavy chain of said polypeptide) (Clone 565, CNCM-4262) and said anti-HER2 antibody comprises an antigen recognition domain having complementarity determining region (CDR) amino acid sequences as set forth in: SEQ ID NOs: 21 (CDR1), 22 (CDR2) and 23 (CDR3) (sequentially arranged from N to C on a light chain of said polypeptide) and 24 (CDR1), 25 (CDR2) and 26 (CDR3) (sequentially arranged from N to C on a heavy chain of said polypeptide) (Clone N12, CNCM-I-4112);

(iii) said anti-EGFR antibody comprises an antigen recognition domain having complementarity determining region (CDR) amino acid sequences as set forth in: SEQ ID NOs: 15 (CDR1), 16 (CDR2) and 17 (CDR3) (sequentially arranged from N to C on a light chain of said polypeptide) and 18 (CDR1), 19 (CDR2) and 20 (CDR3) (sequentially arranged from N to C on a heavy chain of said polypeptide) (Clone 565, CNCM-4262) and said anti-HER3 antibody comprises an antigen recognition domain having complementarity determining region (CDR) amino acid sequences as set forth in: SEQ ID NOs: 27 (CDR1), 28 (CDR2) and 29 (CDR3) (sequentially arranged from N to C on a light chain of said polypeptide) and 30 (CDR1), 31 (CDR2) and 32 (CDR3) (sequentially arranged from N to C on a heavy chain of said polypeptide) (Clone NG33);

(iv) said anti-HER2 antibody an antigen recognition domain having complementarity determining region (CDR) amino acid sequences as set forth in: SEQ ID NOs: 21 (CDR1), 22 (CDR2) and 23 (CDR3) (sequentially arranged from N to C on a light chain of said polypeptide) and 24 (CDR1), 25 (CDR2) and 26 (CDR3) (sequentially arranged from N to C on a heavy chain of said polypeptide) (Clone N12, CNCM-I-4112) and said anti-HER3 antibody comprises an antigen recognition domain having complementarity determining region (CDR) amino acid sequences as set forth in: SEQ ID NOs: 27 (CDR1), 28 (CDR2) and 29 (CDR3) (sequentially arranged from N to C on a light chain of said polypeptide) and 30 (CDR1), 31 (CDR2) and 32 (CDR3) (sequentially arranged from N to C on a heavy chain of said polypeptide) (Clone NG33);

(v) said anti-EGFR antibody comprises an antigen recognition domain having complementarity determining region (CDR) amino acid sequences as set forth in: SEQ ID NOs: 15 (CDR1), 16 (CDR2) and 17 (CDR3) (sequentially arranged from N to C on a light chain of said polypeptide) and 18 (CDR1), 19 (CDR2) and 20 (CDR3) (sequentially arranged from N to C on a heavy chain of said polypeptide) (Clone 565, CNCM-4262), said anti-HER2 antibody comprises an antigen recognition domain having complementarity determining region (CDR) amino acid sequences as set forth in: SEQ ID NOs: 21 (CDR1), 22 (CDR2) and 23 (CDR3) (sequentially arranged from N to C on a light chain of said polypeptide) and 24 (CDR1), 25 (CDR2) and 26 (CDR3) (sequentially arranged from N to C on a heavy chain of said polypeptide) (Clone N12, CNCM-I-4112) and said anti-HER3 antibody comprises an antigen recognition domain having complementarity determining region (CDR) amino acid sequences as set forth in: SEQ ID NOs: 27 (CDR1), 28 (CDR2) and 29 (CDR3) (sequentially arranged from N to C on a light chain of said polypeptide) and 30 (CDR1), 31 (CDR2) and 32 (CDR3) (sequentially arranged from N to C on a heavy chain of said polypeptide) (Clone NG33);

(vi) said anti-EGFR antibody comprises cetuximab; and said anti-HER3 antibody comprises an antigen recognition domain having complementarity determining region (CDR) amino acid sequences as set forth in: SEQ ID NOs: 27 (CDR1), 28 (CDR2) and 29 (CDR3) (sequentially arranged from N to C on a light chain of said polypeptide) and 30 (CDR1), 31 (CDR2) and 32 (CDR3) (sequentially arranged from N to C on a heavy chain of said polypeptide) (Clone NG33);

(vii) said anti-HER2 antibody comprises trastuzumab; and said anti-HER3 antibody comprises an antigen recognition domain having complementarity determining region (CDR) amino acid sequences as set forth in: SEQ ID NOs: 27 (CDR1), 28 (CDR2) and 29 (CDR3) (sequentially arranged from N to C on a light chain of said polypeptide) and 30 (CDR1), 31 (CDR2) and 32 (CDR3) (sequentially arranged from N to C on a heavy chain of said polypeptide) (Clone NG33); and/or (viii) said anti-EGFR antibody comprises cetuximab, said anti-HER2 antibody comprises trastuzumab; and said anti-HER3 antibody comprises an antigen recognition domain having complementarity determining region (CDR) amino acid sequences as set forth in: SEQ ID NOs: 27 (CDR1), 28 (CDR2) and 29 (CDR3) (sequentially arranged from N to C on a light chain of said polypeptide) and 30 (CDR1), 31 (CDR2) and 32 (CDR3) (sequentially arranged from N to C on a heavy chain of said polypeptide) (Clone NG33).

The antibodies may be formulated each in a different formulation, two in one formulation and the other one in a separate formulation, or all in the same formulation i.e.: anti-EGFR, anti-HER2 and antiHER3; anti-EGFR+anti-HER2 and anti-HER3; anti-EGFR+anti-HER3 and anti-HER2; anti-HER2+anti-HER3 and anti-EGFR or anti-EGFR+anti-HER2+anti-HER3.

According to specific embodiments, the pharmaceutical composition further comprises as an active ingredient a TKI.

According to specific embodiments, the active ingredients are in a co-formulation.

According to other specific embodiments, the active ingredients are in separate formulations.

The antibodies and/or TKIs of the present invention can also be attached to a cytotoxic agent or provided together with a cytotoxic agent.

Thus, for example, the antibodies and/or TKIs of the present invention can be administered along with analgesics, chemotherapeutic agents (e.g., anthracyclins), radiotherapeutic agents, hormonal therapy and other treatment regimens (e.g., surgery) which are well known in the art.

As used herein, a "pharmaceutical composition" refers to a preparation of one or more of the active ingredients described herein with other chemical components such as physiologically suitable carriers and excipients. The purpose of a pharmaceutical composition is to facilitate administration of a compound to an organism.

As used herein, the term "active ingredient" refers to the antibodies accountable for the intended biological effect.

Hereinafter, the phrases "physiologically acceptable carrier" and "pharmaceutically acceptable carrier", which may be used interchangeably, refer to a carrier or a diluent that does not cause significant irritation to an organism and does not abrogate the biological activity and properties of the administered compound. An adjuvant is included under these phrases.

Herein, the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils, and polyethylene glycols.

Techniques for formulation and administration of drugs may be found in the latest edition of "Remington's Pharmaceutical Sciences," Mack Publishing Co., Easton, Pa., which is herein fully incorporated by reference.

Suitable routes of administration may, for example, include oral, rectal, transmucosal, especially transnasal, intestinal, or parenteral delivery, including intramuscular, subcutaneous, and intramedullary injections, as well as intrathecal, direct intraventricular, intravenous, intraperitoneal, intranasal, or intraocular injections.

Alternately, one may administer the pharmaceutical composition in a local rather than systemic manner, for example, via injection of the pharmaceutical composition directly into a tissue region of a patient.

Pharmaceutical compositions of the present invention may be manufactured by processes well known in the art, e.g., by means of conventional mixing, dissolving, granulating, dragee-making, levigating, emulsifying, encapsulating, entrapping, or lyophilizing processes.

Pharmaceutical compositions for use in accordance with the present invention thus may be formulated in conventional manner using one or more physiologically acceptable carriers comprising excipients and auxiliaries, which facilitate processing of the active ingredients into preparations that can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries as desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, and sodium carbomethyl-cellulose; and/or physiologically acceptable polymers such as polyvinylpyrrolidone (PVP). If desired, disintegrating agents, such as cross-linked polyvinyl pyrrolidone, agar, or alginic acid or a salt thereof, such as sodium alginate, may be added.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions, and suitable organic solvents or solvent mixtures. Dyestuffs or pigments may be added to the tablets or dragee coatings for identification or to characterize different combinations of active compound doses.

Pharmaceutical compositions that can be used orally include push-fit capsules made of gelatin, as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate, and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane, or carbon dioxide. In the case of a pressurized aerosol, the dosage may be determined by providing a valve to deliver a metered amount. Capsules and cartridges of, for example, gelatin for use in a dispenser may be formulated containing a powder mix of the compound and a suitable powder base, such as lactose or starch.

The pharmaceutical composition described herein may be formulated for parenteral administration, e.g., by bolus injection or continuous infusion. Formulations for injection may be presented in unit dosage form, e.g., in ampoules or in multidose containers with, optionally, an added preservative. The compositions may be suspensions, solutions, or emulsions in oily or aqueous vehicles, and may contain formulatory agents such as suspending, stabilizing, and/or dispersing agents.

Pharmaceutical compositions for parenteral administration include aqueous solutions of the active preparation in water-soluble form. Additionally, suspensions of the active ingredients may be prepared as appropriate oily or water-based injection suspensions. Suitable lipophilic solvents or vehicles include fatty oils such as sesame oil, or synthetic fatty acid esters such as ethyl oleate, triglycerides, or liposomes.

Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the active ingredients, to allow for the preparation of highly concentrated solutions.

Alternatively, the active ingredient may be in powder form for constitution with a suitable vehicle, e.g., a sterile, pyrogen-free, water-based solution, before use.

The pharmaceutical composition of the present invention may also be formulated in rectal compositions such as suppositories or retention enemas, using, for example, conventional suppository bases such as cocoa butter or other glycerides.

Pharmaceutical compositions suitable for use in the context of the present invention include compositions wherein the active ingredients are contained in an amount effective to achieve the intended purpose. More specifically, a "therapeutically effective amount" means an amount of active ingredients (e.g., a nucleic acid construct) effective to prevent, alleviate, or ameliorate symptoms of a disorder (e.g., ischemia) or prolong the survival of the subject being treated.

Determination of a therapeutically effective amount is well within the capability of those skilled in the art, especially in light of the detailed disclosure provided herein.

For any preparation used in the methods of the invention, the dosage or the therapeutically effective amount can be estimated initially from in vitro and cell culture assays. For example, a dose can be formulated in animal models to achieve a desired concentration or titer. Such information can be used to more accurately determine useful doses in humans.

Since administration of the antibody combination is expected to produce improved results over the administration of single antibodies, the therapeutically effective dose of each of the antibodies in the combined treatment may be for example less than 50%, 40%, 30%, 20% or even less than 10% the of the FDA approved dose.

Since administration of the antibody and TKI combination is expected to produce improved results over the administration of TKI as a monotherapy, the therapeutically effective dose of the TKI in the combined treatment may be for example less than 50%, 40%, 30%, 20% or even less than 10% the of the FDA approved dose.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration, and dosage can be chosen by the individual physician in view of the patient's condition. (See, e.g., Fingl E. et al. (1975), "The Pharmacological Basis of Therapeutics," Ch. 1, p. 1.)

Dosage amount and administration intervals may be adjusted individually to provide sufficient plasma or brain levels of the active ingredient to induce or suppress the biological effect (i.e., minimally effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations (e.g., weekly or bi-weekly administrations), with course of treatment lasting from several days to several weeks, or until cure is effected or diminution of the disease state is achieved.

According to specific embodiments the administering comprises multiple administrations.

According to specific embodiments the multiple administrations comprise bi-weekly administrations.

The amount of a composition to be administered will, of course, be dependent on the subject being treated, the severity of the affliction, the manner of administration, the judgment of the prescribing physician, etc.

Typically used models for analyzing the effect of the agents described herein on tumors are provided infra.

An animal lung tumor model expressing a T790M mutated EGFR is described e.g. in Regales et al. PLoS ONE (2007) 2:e810 and Politi et al. Genes Dev. (2006) 20:1496-1510.

Suitable cells for use in animal models and in vitro analyses include but are not limited to H1975, PC9ER, H820, HCC827 and H1650.

Compositions of the present invention may, if desired, be presented in a pack or dispenser device, such as an FDA-approved kit, which may contain one or more unit dosage forms containing the active ingredient. The pack may, for example, comprise metal or plastic foil, such as a blister pack. The pack or dispenser device may be accompanied by instructions for administration. The pack or dispenser device may also be accompanied by a notice in a form prescribed by a governmental agency regulating the manufacture, use, or sale of pharmaceuticals, which notice is reflective of approval by the agency of the form of the compositions for human or veterinary administration. Such notice, for example, may include labeling approved by the U.S. Food and Drug Administration for prescription drugs or of an approved product insert. Compositions comprising a preparation of the invention formulated in a pharmaceutically acceptable carrier may also be prepared, placed in an appropriate container, and labeled for treatment of an indicated condition, as further detailed above.

According to another aspect there is provided an article of manufacture or a kit identified for treating cancer resistance to a tyrosine kinase inhibitor (TKI) comprising a packaging material packaging in separate containers an anti-EGFR antibody, an anti-HER2 antibody and an anti-HER3 antibody, wherein:

(i) said anti-HER3 antibody comprises an antigen recognition domain having complementarity determining region (CDR) amino acid sequences as set forth in: SEQ ID NOs: 27 (CDR1), 28 (CDR2) and 29 (CDR3) (sequentially arranged from N to C on a light chain of said polypeptide) and 30 (CDR1), 31 (CDR2) and 32 (CDR3) (sequentially arranged from N to C on a heavy chain of said polypeptide) (Clone NG33);

(ii) said anti-EGFR antibody comprises an antigen recognition domain having complementarity determining region (CDR) amino acid sequences as set forth in: SEQ ID NOs: 15 (CDR1), 16 (CDR2) and 17 (CDR3) (sequentially arranged from N to C on a light chain of said polypeptide) and 18 (CDR1), 19 (CDR2) and 20 (CDR3) (sequentially arranged from N to C on a heavy chain of said polypeptide) (Clone 565, CNCM-4262) and said anti-HER2 antibody comprises an antigen recognition domain having complementarity determining region (CDR) amino acid sequences as set forth in: SEQ ID NOs: 21 (CDR1), 22 (CDR2) and 23 (CDR3) (sequentially arranged from N to C on a light chain of said polypeptide) and 24 (CDR1), 25 (CDR2) and 26 (CDR3) (sequentially arranged from N to C on a heavy chain of said polypeptide) (Clone N12, CNCM-I-4112);

(iii) said anti-EGFR antibody comprises an antigen recognition domain having complementarity determining region (CDR) amino acid sequences as set forth in: SEQ ID NOs: 15 (CDR1), 16 (CDR2) and 17 (CDR3) (sequentially arranged from N to C on a light chain of said polypeptide) and 18 (CDR1), 19 (CDR2) and 20 (CDR3) (sequentially arranged from N to C on a heavy chain of said polypeptide) (Clone 565, CNCM-4262) and said anti-HER3 antibody comprises an antigen recognition domain having complementarity determining region (CDR) amino acid sequences as set forth in: SEQ ID NOs: 27 (CDR1), 28 (CDR2) and 29 (CDR3) (sequentially arranged from N to C on a light chain of said polypeptide) and 30 (CDR1), 31 (CDR2) and 32 (CDR3) (sequentially arranged from N to C on a heavy chain of said polypeptide) (Clone NG33);

(iv) said anti-HER2 antibody an antigen recognition domain having complementarity determining region (CDR) amino acid sequences as set forth in: SEQ ID NOs: 21 (CDR1), 22 (CDR2) and 23 (CDR3) (sequentially arranged from N to C on a light chain of said polypeptide) and 24 (CDR1), 25 (CDR2) and 26 (CDR3) (sequentially arranged from N to C on a heavy chain of said polypeptide) (Clone N12, CNCM-I-4112) and said anti-HER3 antibody comprises an antigen recognition domain having complementarity determining region (CDR) amino acid sequences as set forth in: SEQ ID NOs: 27 (CDR1), 28 (CDR2) and 29 (CDR3) (sequentially arranged from N to C on a light chain of said polypeptide) and 30 (CDR1), 31 (CDR2) and 32 (CDR3) (sequentially arranged from N to C on a heavy chain of said polypeptide) (Clone NG33);

(v) said anti-EGFR antibody comprises an antigen recognition domain having complementarity determining region (CDR) amino acid sequences as set forth in: SEQ ID NOs: 15 (CDR1), 16 (CDR2) and 17 (CDR3) (sequentially arranged from N to C on a light chain of said polypeptide) and 18 (CDR1), 19 (CDR2) and 20 (CDR3) (sequentially arranged from N to C on a heavy chain of said polypeptide) (Clone 565, CNCM-4262), said anti-HER2 antibody comprises an antigen recognition domain having complementarity determining region (CDR) amino acid sequences as set forth in: SEQ ID NOs: 21 (CDR1), 22 (CDR2) and 23 (CDR3) (sequentially arranged from N to C on a light chain of said polypeptide) and 24 (CDR1), 25 (CDR2) and 26 (CDR3) (sequentially arranged from N to C on a heavy chain of said polypeptide) (Clone N12, CNCM-I-4112) and said anti-HER3 antibody comprises an antigen recognition domain having complementarity determining region (CDR) amino acid sequences as set forth in: SEQ ID NOs: 27 (CDR1), 28 (CDR2) and 29 (CDR3) (sequentially arranged from N to C on a light chain of said polypeptide) and 30 (CDR1), 31 (CDR2) and 32 (CDR3) (sequentially arranged from N to C on a heavy chain of said polypeptide) (Clone NG33);

(vi) said anti-EGFR antibody comprises cetuximab; and said anti-HER3 antibody comprises an antigen recognition domain having complementarity determining region (CDR) amino acid sequences as set forth in: SEQ ID NOs: 27 (CDR1), 28 (CDR2) and 29 (CDR3) (sequentially arranged from N to C on a light chain of said polypeptide) and 30 (CDR1), 31 (CDR2) and 32 (CDR3) (sequentially arranged from N to C on a heavy chain of said polypeptide) (Clone NG33);

(vii) said anti-HER2 antibody comprises trastuzumab; and said anti-HER3 antibody comprises an antigen recognition domain having complementarity determining region (CDR) amino acid sequences as set forth in: SEQ ID NOs: 27 (CDR1), 28 (CDR2) and 29 (CDR3) (sequentially arranged from N to C on a light chain of said polypeptide) and 30 (CDR1), 31 (CDR2) and 32 (CDR3) (sequentially arranged from N to C on a heavy chain of said polypeptide) (Clone NG33); and/or (viii) said anti-EGFR antibody comprises cetuximab, said anti-HER2 antibody comprises trastuzumab; and said anti-HER3 antibody comprises an antigen recognition domain having complementarity determining region (CDR) amino acid sequences as set forth in: SEQ ID NOs: 27 (CDR1), 28 (CDR2) and 29 (CDR3) (sequentially arranged from N to C on a light chain of said polypeptide) and 30 (CDR1), 31 (CDR2) and 32 (CDR3) (sequentially arranged from N to C on a heavy chain of said polypeptide) (Clone NG33).

According to specific embodiments the article of manufacture or kit further comprises TKI.

As used herein, the term "separate containers" refers to at least two containers.

The packaging material may comprise at least one, at least two or at least three containers for packaging the antibodies. According to specific embodiments the packaging material comprises at least two containers for packaging the antibodies and optionally the TKI.

The article of manufacture or kit may be accompanied by instructions for use.

It will be appreciated that the antibodies and/or TKIs of the present invention can be provided to the individual with additional active agents to achieve an improved therapeutic effect as compared to treatment with the antibodies alone or with the combined antibody and TKIs treatment. In such therapy, measures (e.g., dosing and selection of the complementary agent) are taken to adverse side effects which may be associated with combination therapies.

Administration of such combination therapy can be simultaneous, such as in a single capsule having a fixed ration of these active agents or in multiple capsules for each agent.

In the treatment of lung cancer (e.g. NSCLC) standard methods of treatment which can be combined with the antibody treatment of the present invention include, surgery, chemotherapy, radiotherapy, laser therapy and photodynamic therapy.

It is expected that during the life of a patent maturing from this application many relevant therapies will be developed and the scope of the terms TKI, chemotherapy and radiation therapy is intended to include all such new technologies a priori.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

When reference is made to particular sequence listings, such reference is to be understood to also encompass sequences that substantially correspond to its complementary sequence as including minor sequence variations, resulting from, e.g., sequencing errors, cloning errors, or other alterations resulting in base substitution, base deletion or base addition, provided that the frequency of such variations is less than 1 in 50 nucleotides, alternatively, less than 1 in 100 nucleotides, alternatively, less than 1 in 200 nucleotides, alternatively, less than 1 in 500 nucleotides, alternatively, less than 1 in 1000 nucleotides, alternatively, less than 1 in 5,000 nucleotides, alternatively, less than 1 in 10,000 nucleotides.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Materials and Methods

Antibodies and reagents—Generation of anti-EGFR monoclonal antibodies (mAbs) 565 and 111 has been described (Friedman et al. Proceedings of the National Academy of Sciences of the United States of America (2005) 102: 1915-1920). The anti-HER2 mAbs 12 (N12) and 26 (L26) were generated as described (Klapper et al. Oncogene (1997) 14: 2099-2109). The anti-HER3 252 (XC252) was previously described (Chen et al. The Journal of biological chemistry (1996) 271, 7620-7629). Cetuximab and trastuzumab were purchased from Merck and Roche, respectively. Anti-HER2 and anti-HER3 antibodies (Santa Cruz Biotechnology), anti-Tubulin and anti-phospho-ERK antibodies (Sigma Aldrich), anti-EGFR antibody (Alexis), Anti-phosho-EGFR (Y1068), anti-HER2, anti-phosho-HER2 (Y1221/2), anti-phospho-HER3 (Y1289), anti-phospho-AKT (S473), and anti-AKT antibodies (Cell Signaling Technology) were used for western-blot analysis. Anti-Ki-67 antibody Cell Marque Cat#275R. Erlotinib was obtained from LC Laboratories; stock solutions (23 mmol/L) were prepared in DMSO and stored at −20° C. AZD-9291 and CO-1686 were obtained from Selleckchem Cat#57297 and Cat#57284, respectively.

Generation of mAb anti-HER3 NG33 (also referred to herein as 33)—Immunization of Balb/c mice with IgB3, fusion between NSO myeloma cells and splenocytes from IgB3-immunized mice, and the subsequent hybridoma subcloning was performed as previously described (Chen et al. The Journal of biological chemistry (1996) 271(13):7620-762.). Hybridoma supernatant screening, using ELISA, was performed on 96 well-plates coated with IgB3 (1 µg/ml) or with Panitumumab (1 µg/ml) to detect and subtract the non-specific antibodies directed to the human IgG Fc domain. The second step of the screening was performed by immunoprecipitation. Anti-mouse IgG agarose beads were incubated first with 100 µl of hybridoma supernatant and subsequently with whole cell lysate from HER3-expressing T47D cells. The mAbs directed to HER3 were then isotyped using the SBA Clonotyping System/HRP kit (SouthernBiotech). Large quantities of mAbs were produced by purification from hybridoma supernatant maintained in DCCM-2 medium supplemented with 1% FCS and loading on an Agarose-protein G column.

Cell cultures—The H1975 (ATCC; NCI-H1975_CRL-5908) lung cancer cell line (EGFR mutations: L858R and T790M, ATCC; Rockville, Md.), PC9 and erlotinib-resistant PC9ER lung cancer cells (de1746-750+T790M) (described in 16) were maintained in RPMI-1640 supplemented with 10% FCS (Life technology) and antibiotics. PC9ER cells resistant to AZD-9291, denoted as PC9ER-AZDR cells, were generated by incubating PC9ER cells with AZD-9291 for three months. The dose, initially provided at 0.5 nM, was increased every 4 days per 1.5 fold up to 2.5 µM. NL20 (ATCC; NL20_CRL-2503), an immortalized human bronchial epithelial cell line (ATCC, Rockville, Md.) was maintained in F12K medium as recommended by the ATCC. Co-cultures in a ratio of 1:1 of WI38 (ATCC; CCL-75) and PC9ER or H1975 cells were maintained in DME medium supplemented with sodium pyruvate and fetal calf serum (FCS 5%; Life Technology).

Cell growth and survival—Cell survival was assessed using the 3-(4,5-dimethylthiazol-2-yl)-2,5 diphenyl tetrazolium bromide (MTT) assay (Sigma Cat#M2003). Cells were plated on 96-wells plates (2,000 cells/well) in triplicates. The medium was changed the following day and cells were treated as indicated. Following 3-4 days of incubation, MTT reagent was added to the cells for one hour followed by dissolving of the formazan crystals in SDS-DMF solution. Absorbance was measured using a microplate reader, Biorad Model 680, at 570 nm.

Western blot analysis—Cells were grown under specified conditions or treated as indicated. Following the cells were washed twice with cold PBS and scraped into lysis buffer [50 mM Hepes (pH 7.5), 10% glycerol, 150 mM NaCl, 1% Triton X-100, 1 mM EDTA, 1 mM EGTA, 10 mM NaF, 0.1 mM Na3VO4, and a complete protease inhibitor cocktail]. Thereafter, lysates were centrifuged at 14,000 g for 15 minutes at 4° C. The supernatant was used for subsequent procedures. Western blot analyses were conducted following protein separation using gel electrophoresis and transfer to nitrocellulose membranes. Immunoblotting was performed according to the antibody manufacturers' recommendation. Blocking was done using 5% milk in PBST (0.5% Tween20 Sigma Cat#P9416). Antibody binding to membrane blots was detected using horseradish peroxidase—secondary antibodies (Jackson ImmunoResearch Laboratories), followed by treatment with ECL Western blotting detection reagents (GE Healthcare).

Real Time PCR (qPCR)—Total RNA was isolated using PerfectPure RNA Cultured Cell Kit (5-prime, Hamburg). Complementary DNA was synthesized using the miScript kit (QIAGEN). Specific primers to HER2, HER3 as well as the house keeping gene GAPDH were designed using Primer3 software:

```
HER2-Forward
                                    (SEQ ID NO: 7)
5'-gaggtggtacttcaattgcgactca-3';

HER2-Reverse
                                    (SEQ ID NO: 8
5'-agggaaggcggacgcctgat-3';

HER3-Forward
                                    (SEQ ID NO: 9)
5'-tgcagtggattcgagaagc-3';

HER3-Reverse
                                    (SEQ ID NO: 10)
5'-agttcaacatgacgaagatg-3';

GAPDH-Forward
                                    (SEQ ID NO: 11)
5'-acagttgccatgtagacc-3';

GAPDH-Reverse
                                    (SEQ ID NO: 12)
5'-tttttggttgagcacagg-3'.
```

Real-time quantitative PCR (qPCR) analyses were performed using SYBR Green kit (Qiagen or Applied Biosystems) and Step One Plus Real-Time PCR System from Thermo Fisher Scientific. qPCR signals (cT) were normalized to GAPDH.

Immunocytochemistry—Cells were grown on glass cover slips in 24-wells plates and treated with the indicated combination of antibodies in a total concentration of 10 µg/ml. For Ki67 staining, H1975 cells were fixed for 20 minutes at room temperature with 3.7% paraformaldehyde (PFA), followed by permeabilization in 0.3% Triton X-100 for 5 minutes and then rinsed three times in saline containing 0.1% Tween® (PBS-T). Cells were then incubated for 1 hour with 3% albumin in PBS-T, followed by overnight incubation at 4° C. with a primary antibody in PBS-T containing albumin (1%). Following incubation, the cells were washed in PBS-T and stained for one hour at room temperature with a fluorescently labeled secondary antibody (488 Alexa Fluor) and DAPI. Following three additional washes, the coverslips were placed, cell face down, onto 10 µl drops of ProLong Gold antifade reagent (Invitrogen) and were kept overnight protected from light. Samples were examined using a Delta Vision (Applied Precision) microscope. For HER2 and HER3 up-regulation analyses, cells were treated as indicated, acid washed at 4° C. for 30 minutes, rinsed in saline and fixed with 3.7% PFA for 20 minutes. The acid wash was performed using an acidic solution (150 mmol/L NaCl, 0.1 mmol/L glycine, pH=2.1). Samples were processed as previously described, with the exception that Triton X-100 or Tween® were used only after incubation with the primary antibody. Primary antibodies: anti-EGFR (cell signaling Cat#4267) used according to manufacturer's instructions; anti-HER2 (L26) and anti-HER3 (252) at a concentration of 0.25 µg/ml were prepared in our laboratory.

siRNA transfection—Specific On-target EGFR and scramble siRNA (siCTRL) as well as On-target HER2 and HER3 siRNAs were purchased from Dharmacon (GE Healthcare: HER3 siRNA Cat#L-003127, EGFR siRNA Cat#L-003114, HER2 siRNA Cat#L-003126, CTRL siRNA Cat#D-001810-10-05. siRNA oligonucleotides transfection was performed using Oligofectamine (Invitrogen).

Luciferase promoter reporter assay—Plasmids containing the HER2 (pNeuLite) or HER3 (HPRM23883) promoter regions were purchased, respectively, from Addgene and Genecopeia. The HER2 promoter region was amplified by PCR using Pfu-Turbo DNA polymerase (Stratagene) with the primer sequences: Forward: 5'-ggcgtcccggcgctag-gaaggcctgcgcagagag-3' (SEQ ID NO: 13) and Reverse: 5'-ctctcttcgcgcaggccttcctagcgccgggacgcc-3' (SEQ ID NO: 14), and cloned in pGM3-Basic-Vector (Promega) (pHER2-prom-LucFF). The HER3 promoter region was cloned into the pGM3-Basic-Vector using BglII and HindIII restriction enzymes (pHER3-prom-LucFF). Renilla luciferase coding region from the pRL plasmid (Promega) cloned into the 3' of mCherry coding region of the pmCherry-C1 vector (pmCheRNL) was a kind gift from Dr. Andrea Levi. The PC9ER and H1975 cell lines were co-transfected using Lipofectamine2000 (Invitrogen) with pHER2-prom-LucFF and pmCheRNL or pHER3-prom-LucRNL and pmCheRNL. Cells co-transfected with pmCheRNL and pGL3-Control-Vector (Promega) or pGL3-Basic-Vector served, respectively, as positive and negative controls. Cells were then selected for 3 weeks with puromycin (1 µg/ml). Stably co-transfected derivative cell lines were then treated with mAb 565 or Cetuximab. Specifically, 30.000 cells were plated on 24 well plates, 48 hours later cells were treated with 10 mg/ml of the indicated antibody for 8-24 hours as indicated. Luciferase activity was measured using VictorX Luminometer (Promega) and the Dual-Luciferase Reporter Assay (Promega).

Cell survival determined by luciferase assays—WI38 and NL20 cells were stably transfected with a pmCheRNL construct. Similarly, PC9ER and H1975 were infected with eGFP-Firefly Luciferase lentiviral particles. Following 3 weeks of drug selection, derivative labeled cell were treated with mAbs and relative Firefly or Renilla luciferase signals were determined using Renilla-Glo or Steady-Glo Luciferase Assay kits (Promega).

Flow cytometry analyses—NL20, WI38, H1975 and PC9ER cells were trypsinized and washed twice in saline containing 1% albumin (weight/volume). The cells were then incubated for 1-2 hours at 4° C. with 10 µg/ml anti-EGFR, anti-HER2 or anti-HER3 mAb (mAb 565, mAb L26 or mAb 252, respectively). Unstained cell served as control. Following two washes, the cells were incubated for one hour at 4° C. with an anti-mouse antibody coupled to AlexaFluor 488. Following staining cells were washed once and analyzed by BD LSRII flow cytometer (Becton Dickinson, Franklin Lakes, N.J.). Data was analyzed using the FlowJo software. For PI staining, following 48 h treatment as indicated in FIGS. 8A-B cells were washed once with PBS prior to tripsinization. Cells were then re-suspended in PBS and Propidium Iodide solution (Sigma Cat#P4864) was added according to manufacturer's instructions. Following staining cells were washed once and analyzed by BD LSRII flow cytometer (Becton Dickinson, Franklin Lakes, N.J.). Data was analyzed using the FlowJo software.

Tumorigenic growth in-vivo—The animal studies were approved by the Weizmann Institute's Review Board (IRB). CD1/nude mice (Harlan Laboratories) were randomized in groups of ten mice and injected subcutaneously in the right flank with H1975 lung cancer cells ($3 \times 10^6$ per mouse) or with PC9ER lung cancer cells ($4 \times 10^6$ per mouse). PBS or mAbs were injected intraperitoneally once every three days at a total dose of 200 µg per mouse per injection starting 11 days following cells injection, until tumors reached the size of 1,500 mm$^3$. In experiments evaluating the effect of the TKI AZD-9291, Vehicle (Vehicle formulation: HPMC 0.5% (sigma Cat#56340), Tween80 0.1% (Sigma Cat #P8074 in water), Erlotinib at a dose of 50 mg/kg per injection, or AZD9291 at a dose of 1 or 5 mg/kg per injection were injected daily intraperitoneally. In one experiment (FIG. 17), mice were treated daily with Erlotinib at a dose of 50 mg/kg per injection until tumors reached a size of 800 mm$^3$ and only then were treated as indicated. Tumor volume was evaluated twice a week and body weight was evaluated once a week. Mice were euthanized when tumor size reached 1,500 mm$^3$. Few of the tumors were harvested from mice at the indicated time points and taken for further evaluation. Survival of the tumor bearing mice was recorded and depicted by Kaplan-Meier analysis.

Statistical and data analyses—Data was represented using the Prism GraphPad software. Statistical analysis was performed using One-way ANOVA with Bonferroni's comparison test (*$p \leq 0.05$;  $p \leq 0.01$; *$p \leq 0.001$).

Example 1

Anti-EGFR Treatment Induces Up-Regulation of HER2 and HER3 Expression In-Vitro

Most non-small cell lung cancer (NSCLC) patients treated with EGFR-specific tyrosine kinase inhibitors (TKIs), acquire resistance within approximately one year and the most common mechanism involves a specific second site mutation within EGFR denoted T790M (6-10).

In order to elucidate the ability of anti-EGFR to overcome EGFR TKI resistance, three NSCLC cell lines were selected: patient-derived H1975 cells expressing a double mutant EGFR (L858R and T790M), PC9 cell line and PC9ER cell line, a derivative of PC9 (del746-750 EGFR, also called LREA deletion) that acquired in-vitro the T790M secondary mutation (16).

The survival of the cells was monitored following 3 days treatment with increasing doses of either EGFR TKI inhibitor erlotinib or the anti-EGFR monoclonal antibody (mAb) cetuximab (FIG. 1A). As expected, the parental PC9 cells were strongly inhibited by erlotinib and weakly inhibited by cetuximab. However, in accordance with a previous study (17), NSCLC cells expressing the EGFR T790M mutation (i.e. PC9ER and H1975) exhibited resistance to both treatments.

Concentrating on the resistant cell lines, as demonstrated in FIG. 1B, long-term exposure to cetuximab or to another anti-EGFR antibody, mAb 565, resulted in gradual decrease in the expression levels of EGFR in the treated cells. Interestingly, this was accompanied by up-regulation of HER2 and HER3, as well as their active tyrosine phosphorylated forms, suggesting emergence of positive feedback.

The delayed response in the up-regulation of HER2 and HER3 implied the regulation is at the transcriptional level, a scenario supported by the results presented in FIGS. 1C-E and FIG. 2:

(1) Quantitative PCR analyses performed on H1975 and PC9ER cells extracts displayed moderate, time-dependent up-regulation of HER2 and HER3 transcripts (FIG. 1C).
(2) PC9ER and H1975 cells transfected with promoter-reporter plasmids in which a luminescent reporter was driven by the promoter of HER2 or HER3, verified that cetuximab treatment strongly increases HER2 promoter activity and weakly increases HER3 promoter activity (FIGS. 1D-E).
(3) Similarly to mAb treatment, depletion of EGFR expression using small interfering RNA oligonucleotides (siRNAs) was followed by up-regulation of the HER2 and HER3 proteins (FIG. 2).

Taken together, this data indicated that downregulation of mutant EGFRs induces a compensatory feedback loop that up-regulates HER2 and HER3.

Example 2

Combined Treatment with Anti-EGFR, Anti-HER2 and Anti-HER3 Synergistically Downregulates Protein Expression of All Three Receptors In-Vitro The present inventors have assumed that preventing HER2/HER3 up-regulation might augment the effects of anti-EGFR mAbs on TKI-resistant tumors. As a first step the mAb 565, 12 and 33 against EGFR, HER2 and HER3, respectively, were selected on the basis of their superior ability to inhibit survival of cultured NSCLC cells (FIG. 3). Fluorescence microscopy revealed that none of the three mAbs or their double combinations was able to significantly downregulate protein expression of all three receptors. However, as demonstrated in FIG. 4 the triple combination almost completely depleted EGFR, HER2 and HER3 protein expression. The triple combination retained the ability to enhance HER2 and HER3 transcription, an activity attributable to the anti-EGFR antibody (FIGS. 5A-B).

A delayed positive feedback loop that engages HER2 and HER3 is expected to activate EGFR and downstream pathways, such as ERK or AKT. To this end, expression of EGFR, HER2, HER3, AKT, ERK and their phosphorylated forms was evaluated by western blot analysis in PC9ER cells treated with an anti-EGFR mAb, anti-HER2, anti-HER3 and combinations of the three. As demonstrated in FIG. 6, treatment of PC9ER cells with an anti-EGFR mAb initially reduced phosphorylation of the constitutively active mutant receptor. In parallel, EGFR gradually underwent degradation and almost disappeared 12 hours following treatment. Nevertheless, at this late time point a strikingly strong re-phosphorylation of the residual EGFR was observed. This hyper-activation might relate to the concomitant up-regulation of HER2 and HER3, as well as their active phosphorylated forms. As expected, the time course of EGFR phosphorylation was mirrored by the kinetics of ERK activation, including a late peak (at about 24 hours) of hyper-phosphorylation (FIG. 6). Surprisingly, however, AKT showed no similar effects and, like anti-EGFR, anti-HER2 antibodies induced ERK hyper-phosphorylation (FIG. 6). Importantly, as demonstrated in FIG. 6, although no double mAb combination completely prevented re-activation of ERK, this was entirely prevented by the triple mAb combination. FIG. 6 also clearly demonstrates that treatment with the triple mAb combination resulted in total depletion of EGFR, in accordance with the immunofluorescence analysis (FIG. 4).

Taken together, this data indicated that combined treatment with anti-EGFR, anti-HER2 and anti-HER3 synergistically reduces protein levels of all three receptors and their downstream pathways.

Example 3

Combined Treatment with Anti-EGFR, Anti-HER2 and Anti-HER3 Synergistically Affect Growth of Tumor Cells In-Vitro The effect of the triple mAb combination on inhibition of cell growth was evaluated in the NSCLC cell lines (H1975 and PC9ER). As can be seen in FIGS. 7A-B, a colorimetric MTT assay indicated that the anti-EGFR mAb most potently inhibited survival of both cell lines (approximately 40% following 4 days of incubation) as compared to anti-HER2 and anti-HER3 mAbs. However, a triple combination of the three mAbs inhibited survival of both cell lines more effectively (about 80% in the H1975 and about 60% in the PC9ER) than each of the mAb alone or any double combination of the three.

Immunocytochemistry analysis of the cells for Ki67 expression, a marker of proliferating cells, corroborated the synergistic effect of the triple mAbs treatment on cell growth and survival: whereas 93% of untreated H1975 cells stained positively for Ki67, only 19% of the cells remained positive following two days of treatment with the triple mAbs combination (FIG. 7C).

Despite this strong inhibition, treatment with the triple mAbs combination elicited no signs of apoptosis, as determined by either a dye exclusion assay or caspase-3 cleavage (FIGS. 8A-D).

To test whether treatment with the triple mAbs combination would enhance the toxic effects of conventional therapies, the combined effect of the triple mAbs and cis-platin, a chemotherapeutic drug used to treat NSCLC patients, was examined. As shown in FIGS. 9A-B, treatment with the three anti-EGFR, anti-HER2 and anti-HER3 mAbs augmented the growth inhibitory effect of cis-plain on both NSCLC cell lines (H1975 and PC9ER).

One concern associated with combining drugs is additive adverse effects primarily due to toxicity to non-cancerous cells. To study this and also address drug effects on tumor-stroma interactions, two human non-cancerous cell lines of lung origin: NL20 epithelial cells and WI38 fibroblasts were selected. Flow cytometry analysis ascertained endogenous expression of EGFR, HER2 and HER3 in the selected cell lines (FIG. 10). In the next step, fluorescent derivatives of the non-cancerous cell lines (NL20 and WI38) were established by stably expressing mCherry-Renilla (denoted herein as -CherryRNL); and similar derivatives of the cancerous cell lines (H1975 and PC9ER) were established by infecting the cells with GFP-Firefly (denoted herein as -GFPFF). As clearly demonstrated in FIG. 11, treatment of the labeled NSCLC cell lines with the triple mAbs combination induced dose-dependent inhibition of growth. On the contrary, the triple mAbs treatment had minimal effect on the two labeled non-cancerous cell lines, suggesting that the triple mAbs treatment might spare non-cancerous tissues. This attribute was further examined using tissue-like co-cultures consisting of cancerous and non-cancerous cells. First, the effect of the non-cancerous fibroblasts (W138) on growth of the NSCLC cells (H1975 and PC9ER) was evaluated. As can be seen in FIGS. 12A-B, co-culturing labeled NSCLC cells with either unlabeled NSCLC cells (control) or with unlabeled non-cancerous fibroblasts exemplified that the non-cancerous fibroblasts enhance growth of the two NSCLC cell lines. In contrast, reciprocal experiments indicated that the cancerous cells might inhibit growth of the non-cancerous fibroblasts (FIG. 12C).

These effects may be mediated, on the one hand, by growth factors secreted by stromal cells and, on the other hand, by growth inhibitory cytokines secreted by the tumor cells. Thus, the impact of the anti-EGFR, anti-HER2 and anti-HER2 mAbs on the bi-directional crosstalk was tested. As demonstrated in FIGS. 13A-B, treating the co-cultures with each of the mAbs reduced the ability of the stromal cells to enhance NSCLC cell growth while the triple mAbs combination further augmented this reduction. In addition, while mAb monotherapy had minimal effect on the suppressive effects that the NSCLC cells imposed on the stromal cells (data not shown) the triple mAbs combination significantly decreased the suppressive effects that the NSCLC cells imposed on the stromal cells.

Taken together, the data indicated the ability of the triple mAbs combination to strongly inhibit in-vitro growth of cancerous cells while sparing the non-cancerous cells and possibly depriving the tumor cells from the supportive effect of the stroma.

Example 4

Combined Treatment with Anti-EGFR, Anti-HER2 and Anti-HER3 Synergistically Affect Tumor Growth In-Vivo In the next step the effect of the triple mAbs combination on tumor growth in-vivo in a tumor-bearing mouse model was evaluated. To this end, H1975 NSCLC cells ($3 \times 10^6$) were subcutaneously inoculated in CD1-nu/nu mice. Eleven days following inoculation mice were treated once every three days with anti-EGFR, anti-HER2 anti-HER3 (mAb 565+mAb 12+mAb 33, respectively), as well as with all possible combinations of the three. In accordance with the in-vitro data, the results presented in FIGS. 14A-C demonstrate that mono-therapy using anti-EGFR mAb partly inhibited tumor growth, but neither anti-HER2, anti-HER3 nor combined anti-HER2 and anti-HER3 treatment repressed tumor growth. Although combined treatment consisting of anti-EGFR with either anti-HER2 or anti-HER3 partly inhibited tumor growth, only the triple mAbs combination exerted strong and lasting inhibitory effects on tumor growth, as well as on animal survival. This nearly complete tumor eradication observed may be attributed to the ability of the triple mAbs combination to target TKI-resistant EGFRs to degradation and to simultaneously block the positive feedback loop that re-activates not only EGFR, HER2 and HER3, but also the RAS-ERK pathway (FIG. 6).

Example 5

Combined Treatment with Cetuximab, Trastuzumab and Anti-HER3 Synergistically Affect Tumor Growth In-Vivo The effect of combined antibody treatment on in-vivo tumor growth was tested using the triple mAbs combination composed of the commercial antibodies cetuximab (anti-EGFR), trastuzumab (anti-HER2) and the anti-HER3 mAb 33 and was evaluated in a tumor-bearing mouse model. To this end, PC9ER NSCLC cells ($4 \times 10^6$) were subcutaneously inoculated into CD1-nu/nu mice. Eleven days following inoculation, mice were treated once every three days with cetuximab, trastuzumab and anti-HER3 mAb 33 as well as with all possible combinations of the three. The results presented in FIG. 15 demonstrate that combined treatment consisting of two antibodies had an increased effect on tumor growth inhibition as compared to each of the antibodies alone. Furthermore, the triple mAbs combination exerted strong and lasting inhibitory effects on tumor growth, almost completely abolishing tumor growth.

Second and third generation TKIs are being developed (Liao et al. Current Opinion Oncology, 2015); for example, the commercially available AZD-9291, CO-1686, and HM-61713 inhibit both EGFR activating and resistance mutations, while sparing wild-type EGFR. To compare the effect of such third-generation TKI to the triple antibody combination, CD1-nu/nu mice were subcutaneously inoculated with H1975 NSCLC cells ($3 \times 10^6$) and treated with the irreversible TKI AZD-9291 or the triple mAbs combination cetuximab, trastuzumab and the anti-HER3 mAb 33. The results presented in FIGS. 16A-B, demonstrate that the two treatments, although utilizing very different mechanisms of action, comparably inhibited growth of the erlotinib-resistant human NSCLC. Importantly, AZD-9291 slightly inhibited body weight gain compared with the triple mAb combination (FIG. 16C), which might suggests higher toxicity in animals.

In the next step, a combination of the triple mixture of mAbs (cetuximab+Trastuzumab+mAb33) and AZD9291 was evaluated in CD1-nu/nu mice subcutaneously inoculated with H1975 NSCLC cells ($3 \times 10^6$). As shown in FIG. 17, the combination of the triple mAb and a low dose AZD-9291 had an improved anti-tumor effect as compared to the triple mAb therapy or to a high dose AZD-9291 therapy. These results raise the possibility of combining the two treatment modalities (i.e. triple mAb therapy and TKI) using sub-dosing of the TKI in order to limit adverse effects.

Example 6

NSCLC Develop Resistance to AZD-9291 Therapy While Maintaining Sensitivity to Combined Treatment with Cetuximab, Trastuzumab and Anti-HER3

To evaluate the effect of the triple antibody combination therapy on cells resistant to third-generation TKI, PC9ER NSCLC cells were incubated with AZD-9291 for three months. The surviving cells, denoted herein as PC9ER-AZDR, lost sensitivity to AZD-9291, as evaluated by MTT assay (FIG. 18); and their EGFR remained phosphorylated when exposed to both AZD-9291 and another third generation TKI, CO-1686 (FIG. 19).

On the contrary, the colorimetric MTT assay indicated that treatment with cetuximab, trastuzumab and antiHER3 mAB33 most potently inhibited survival of both PC9ER cells and PC9ER-AZDR cells (FIG. 18).

Taken together, these results indicate that the third-generation TKIs might evoke new resistance mechanisms but the offered treatment using three mAbs can overcome emergence of this resistance.

Taken together, HER2, HER3 and their downstream target are upregulated in response to EGFR-targeting antibody.

Combined treatment with anti-EGFR, anti-HER2 and anti-HER3 mAbs synergistically deplete all three receptors and inhibits growth of TKI resistant NSCLC cells expressing the EGFR T790M mutation both in-vitro and in-vivo.

Example 7

Analysis of EGFR Mutations

Real-time PCR using the TaqMan assay (Applied Biosystems) was performed according to the manufacturer's instructions. Briefly, 10 μL reactions were run, comprising 5 μL of TaqMan universal genotyping master mix, 0.5 μL of TaqMan 20× SNP assay, 3.5 μL ultrapure water, and 1 μL DNA (10 nd/μL) per reaction. Each run included non-template controls (NTC). The real-time PCR reactions were run using a StepOne Plus Real-Time PCR system (Applied Biosystems). The SNP assay included the following primer: EGFR C797S (T→A): forward primer: 5'-GCCT-GCTGGGCATCTG-3' (SEQ ID NO: 33), reverse, 5'-TCTTTGTGTTCCCGGACATAGTC-3' (SEQ ID NO: 34). Probe sequences were as follows: 5'-VIC-TTCGGCT-GCCTCCTG-MGB-NFQ-3' (SEQ ID NO: 35), 5'-FAM-TTCGGCAGCCTCC-MGB-NFQ-3' (SEQ ID NO: 36).

Running protocol: Cycling conditions: 95° C.×10 min (1 cycle), 40 cycles of 94° C.×30 s and 56° C.×1 min. followed by 10° C. hold.

Example 8

The Triple Antibody Combination Can Overcome Acquired Resistance to AZD9291, a Third Generation TKI Considering the recently uncovered mechanisms of resistance to the third generation TKIs (Thress, et al. (2015). Acquired EGFR C797S mutation mediates resistance to AZD9291 in non-small cell lung cancer harboring EGFR T790M. Nature medicine 21, 560-562), which involves a new EGFR mutation, C797S, the present inventors aimed at developing an in-vitro model to closely study emergence of resistance and evaluate the triple antibody strategy for the treatment of resistant tumors. To this end, an AZD9291-resistant derivative cell line from PC9ER cells was established. Following four months of continuous exposure to the drug, resistant cells, hereinafter PC9ER-AZDR cells, were established and compared side by side with PC9ER cells. Using a dose-response experiment that tested sensitivity to AZD9291, PC9ER-AZDR cells clearly demonstrated resistance to the drug compared to the parental cells. Importantly, sensitivity toward the 3×mAbs treatment remained unaltered (FIG. 18).

Immunoblot analysis of sensitive and resistant cell lines confirmed that third generation drugs, both AZD9291 and CO-1686, failed to inhibit EGFR phosphorylation and consequent activation of downstream pathways in PC9ER-AZDR (FIG. 19). Aiming at precisely characterizing the mechanism of drug resistance, a mutational analysis was performed to detect EGFR alterations, specifically the recently reported C797S mutation. As expected, PC9ER-AZDR cells were scored positive for the C797S mutation (FIG. 20).

PC9ER-AZDR cells were inoculated in CD1 nu/nu mice to address the possibility that acquisition of resistance to the third generation TKI (AZD9291) was maintained in an animal setting. Neither erlotinib nor AZD9291 (at both low and high doses) were able to significantly inhibit tumor growth in animals; on the contrary the 3×mAbs treatment strongly reduced tumor volume (FIG. 21). In conclusion, in vitro appearance of the resistance conferring mutation, C797S, is associated with loss of sensitivity of the EGFR's kinase domain toward third generation inhibitors. When tested in animals, the corresponding cells displayed the expected resistance to kinase inhibitors, but they retained unaltered sensitivity to the triple combination of antibodies, implying that the antibodies can overcome resistance to all EGFR kinase domain mutations.

Example 9

The Triple Antibody Combination Can Prevent Relapse of Tumore in an Animal Model, Especially When Combined with a Kinase Inhibitor To establish an animal model that recapitulates the clinical setting, PC9ER tumor xenografts were implanted in immune compromised mice. All animals, but the control group, were subjected to erlotinib treatment (50 mg/kg/d), but as expected no differences were noted at this phase ($1^{st}$ line phase). When tumors reached palpable volumes (approximately 550 $mm^3$), a $2^{nd}$ line phase was applied: each group received one of the following treatments: erlotinib (50 mg/kg/d), 3×mAbs (triple antibody combination; CTX, TRZ, 33; 0.2 mg/mouse/injection), and either low AZD9291 (L; 1 mg/kg/d) or high AZD9291 (H; 5 mg/kg/d). In addition, two combination groups were tested: low AZD9291 (L; 1 mg/kg/d) plus 3×mAbs and high AZD9291 (H; 5 mg/kg/d) plus 3×mAbs. This second phase ended at day 50, such that no further treatment, other than animal inspection, followed. As shown in FIGS. 22A-C, right at the beginning of the post-treatment phase a relapse of tumors in the groups pre-treated with the kinase inhibitor was observed. By contrast, the group of antibody-treated mice exemplified no relapse. The effect of the antibody was further increased when combined with the kinase inhibitor: already the low dose of the inhibitor caused complete disappearance of tumors when combined with the mixture of antibodies. This effect was sustained; no relapse occurred even though animals were left untreated for 40 more days.

In summary, the combination of three antibodies clearly superseded the therapeutic effect of a third generation kinase inhibitor. This was reflected by the ability of the antibody mixture to inhibit lung cancer cells that acquired, in vitro, resistance to AZD9291. Likewise, treatment with the antibodies for a short period of time (30 days) prevented tumor relapse, but a similar length treatment with AZD9291 was followed by a rapid and dramatic relapse once treatment was halted. Despite inferiority, the third generation inhibitor, when combined with antibodies, completely protected animals from tumor relapse and this effect appears to be sustained.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

REFERENCES

Other References are Cited Throughout the Application

1. R. Siegel, J. Ma, Z. Zou, A. Jemal, Cancer statistics, 2014. *CA: a cancer journal for clinicians* 64, 9-29 (2014); published online EpubJan-Feb (10.3322/caac.21208).
2. T. J. Lynch, D. W. Bell, R. Sordella, S. Gurubhagavatula, R. A. Okimoto, B. W. Brannigan, P. L. Harris, S. M. Haserlat, J. G. Supko, F. G. Haluska, D. N. Louis, D. C. Christiani, J. Settleman, D. A. Haber, Activating mutations in the epidermal growth factor receptor underlying responsiveness of non-small-cell lung cancer to gefitinib. *The New England journal of medicine* 350, 2129-2139 (2004); published online EpubMay 20.
3. J. G. Paez, P. A. Janne, J. C. Lee, S. Tracy, H. Greulich, S. Gabriel, P. Herman, F. J. Kaye, N. Lindeman, T. J. Boggon, K. Naoki, H. Sasaki, Y. Fujii, M. J. Eck, W. R. Sellers, B. E. Johnson, M. Meyerson, EGFR mutations in lung cancer: correlation with clinical response to gefitinib therapy. *Science* 304, 1497-1500 (2004); published online EpubJun 4.
4. W. Pao, V. Miller, M. Zakowski, J. Doherty, K. Politi, I. Sarkaria, B. Singh, R. Heelan, V. Rusch, L. Fulton, E. Mardis, D. Kupfer, R. Wilson, M. Kris, H. Varmus, EGF receptor gene mutations are common in lung cancers from "never smokers" and are associated with sensitivity of tumors to gefitinib and erlotinib. *Proceedings of the National Academy of Sciences of the United States of America* 101, 13306-13311 (2004); published online EpubSep 7.
5. Y. Yarden, G. Pines, The ERBB network: at last, cancer therapy meets systems biology. *Nature reviews. Cancer* 12, 553-563 (2012); published online EpubAug (10.1038/nrc3309).
6. T. S. Mok, Y. L. Wu, S. Thongprasert, C. H. Yang, D. T. Chu, N. Saijo, P. Sunpaweravong, B. Han, B. Margono, Y. Ichinose, Y. Nishiwaki, Y. Ohe, J. J. Yang, B. Chewaskulyong, H. Jiang, E. L. Duffield, C. L. Watkins, A. A. Armour, M. Fukuoka, Gefitinib or carboplatin-paclitaxel in pulmonary adenocarcinoma. *The New England journal of medicine* 361, 947-957 (2009); published online EpubSep 3.
7. R. Rosell, T. Moran, C. Queralt, R. Porta, F. Cardenal, C. Camps, M. Majem, G. Lopez-Vivanco, D. Isla, M. Provencio, A. Insa, B. Massuti, J. L. Gonzalez-Larriba, L. Paz-Ares, I. Boyer, R. Garcia-Campelo, M. A. Moreno, S. Catot, C. Rolfo, N. Reguart, R. Palmero, J. M. Sanchez, R. Bastus, C. Mayo, J. Bertran-Alamillo, M. A. Molina, J. J. Sanchez, M. Taron, G. Spanish Lung Cancer, Screening for epidermal growth factor receptor mutations in lung cancer. *The New England journal of medicine* 361, 958-967 (2009); published online EpubSep 3.
8. G. R. Oxnard, M. E. Arcila, J. Chmielecki, M. Ladanyi, V. A. Miller, W. Pao, New strategies in overcoming acquired resistance to epidermal growth factor receptor tyrosine kinase inhibitors in lung cancer. *Clinical cancer research: an official journal of the American Association for Cancer Research* 17, 5530-5537 (2011); published online EpubSep 1 (10.1158/1078-0432.CCR-10-2571).
9. W. Pao, V. A. Miller, K. A. Politi, G. J. Riely, R. Somwar, M. F. Zakowski, M. G. Kris, H. Varmus, Acquired resistance of lung adenocarcinomas to gefitinib or erlotinib is associated with a second mutation in the EGFR kinase domain. *PLoS medicine* 2, e73 (2005); published online EpubMar.
10. S. Kobayashi, T. J. Boggon, T. Dayaram, P. A. Janne, O. Kocher, M. Meyerson, B. E. Johnson, M. J. Eck, D. G. Tenen, B. Halmos, EGFR mutation and resistance of non-small-cell lung cancer to gefitinib. *The New England journal of medicine* 352, 786-792 (2005); published online EpubFeb 24.
11. J. A. Engelman, K. Zejnullahu, T. Mitsudomi, Y. Song, C. Hyland, J. O. Park, N. Lindeman, C. M. Gale, X. Zhao, J. Christensen, T. Kosaka, A. J. Holmes, A. M. Rogers, F. Cappuzzo, T. Mok, C. Lee, B. E. Johnson, L. C. Cantley, P. A. Janne, MET amplification leads to gefitinib resistance in lung cancer by activating ERBB3 signaling. *Science* 316, 1039-1043 (2007); published online EpubMay 18 (10.1126/science.1141478).
12. J. Bean, C. Brennan, J. Y. Shih, G. Riely, A. Viale, L. Wang, D. Chitale, N. Motoi, J. Szoke, S. Broderick, M. Balak, W. C. Chang, C. J. Yu, A. Gazdar, H. Pass, V. Rusch, W. Gerald, S. F. Huang, P. C. Yang, V. Miller, M. Ladanyi, C. H. Yang, W. Pao, MET amplification occurs with or without T790M mutations in EGFR mutant lung tumors with acquired resistance to gefitinib or erlotinib. *Proceedings of the National Academy of Sciences of the United States of America* 104, 20932-20937 (2007); published online EpubDec 26 (10.1073/pnas.0710370104).
13. K. Ohashi, Y. E. Maruvka, F. Michor, W. Pao, Epidermal growth factor receptor tyrosine kinase inhibitor-resistant disease. *Journal of clinical oncology: official journal of the American Society of Clinical Oncology* 31, 1070-1080 (2013); published online EpubMar 10 (10.1200/JCO.2012.43.3912).
14. F. R. Hirsch, P. A. Janne, W. E. Eberhardt, F. Cappuzzo, N. Thatcher, R. Pirker, H. Choy, E. S. Kim, L. Paz-Ares, D. R. Gandara, Y. L. Wu, M. J. Ahn, T. Mitsudomi, F. A. Shepherd, T. S. Mok, Epidermal growth factor receptor inhibition in lung cancer: status 2012. *Journal of thoracic oncology: official publication of the International Association for the Study of Lung Cancer* 8, 373-384 (2013); published online EpubMar (10.1097/JTO.0b013e31827ed0ff).
15. R. Pirker, J. R. Pereira, A. Szczesna, J. von Pawel, M. Krzakowski, R. Ramlau, I. Vynnychenko, K. Park, C. T. Yu, V. Ganul, J. K. Roh, E. Bajetta, K. O'Byrne, F. de Marinis, W. Eberhardt, T. Goddemeier, M. Emig, U. Gatzemeier, Cetuximab plus chemotherapy in patients with advanced non-small-cell lung cancer (FLEX): an open-label randomised phase III trial. *Lancet* 373, 1525-1531 (2009); published online EpubMay 2 (S0140-6736(09)60569-9.
16. E. C. de Bruin, C. Cowell, P. H. Warne, M. Jiang, R. E. Saunders, M. A. Melnick, S. Gettinger, Z. Walther, A. Wurtz, G. J. Heynen, D. A. Heideman, J. Gomez-Roman, A. Garcia-Castano, Y. Gong, M. Ladanyi, H. Varmus, R. Bernards, E. F. Smit, K. Politi, J. Downward, Reduced NF1 expression confers resistance to EGFR inhibition in lung cancer. *Cancer discovery* 4, 606-619 (2014); published online EpubMay (10.1158/2159-8290.CD-13-0741).
17. J. Cho, L. Chen, N. Sangji, T. Okabe, K. Yonesaka, J. M. Francis, R. J. Flavin, W. Johnson, J. Kwon, S. Yu, H. Greulich, B. E. Johnson, M. J. Eck, P. A. Janne, K. K. Wong, M. Meyerson, Cetuximab response of lung cancer- 18. R. Maron, B. Schechter, M. Mancini, G. Mahlknecht, Y. Yarden, M. Sela, Inhibition of pancreatic carcinoma by homo- and heterocombinations of antibodies against EGF-receptor and its kin HER2/ErbB-2. *Proceedings of the National Academy of Sciences of the United States of America* 110, 15389-15394 (2013); published online EpubSep 17 (10.1073/pnas.1313857110).
19. D. A. Ferraro, N. Gaborit, R. Maron, H. Cohen-Dvashi, Z. Porat, F. Pareja, S. Lavi, M. Lindzen, N. Ben-Chetrit, M. Sela, Y. Yarden, Inhibition of triple-negative breast cancer models by combinations of antibodies to EGFR. *Proceedings of the National Academy of Sciences of the United States of America*, (2013); published online EpubJan 14 (10.1073/pnas.1220763110).
20. V. Serra, M. Scaltriti, L. Prudkin, P. J. Eichhorn, Y. H. Ibrahim, S. Chandarlapaty, B. Markman, O. Rodriguez, M. Guzman, S. Rodriguez, M. Gili, M. Russillo, J. L. Parra, S. Singh, J. Arribas, N. Rosen, J. Baselga, PI3K inhibition results in enhanced HER signaling and acquired ERK dependency in HER2-overexpressing breast cancer. *Oncogene* 30, 2547-2557 (2011); published online EpubJun 2 (10.1038/onc.2010.626).
21. I. Amit, R. Wides, Y. Yarden, Evolvable signaling networks of receptor tyrosine kinases: relevance of robustness to malignancy and to cancer therapy. *Mol Syst Biol* 3, 151 (2007).
22. B. N. Kholodenko, J. F. Hancock, W. Kolch, Signalling ballet in space and time. *Nat Rev Mol Cell Biol* 11, 414-426 (2010); published online EpubJun (nrm2901[pii] 10.1038/nrm2901).
23. N. V. Sergina, M. Rausch, D. Wang, J. Blair, B. Hann, K. M. Shokat, M. M. Moasser, Escape from HER-family tyrosine kinase inhibitor therapy by the kinase-inactive HER3. *Nature* 445, 437-441 (2007); published online EpubJan 25 (nature05474 [pii]10.1038/nature05474).
24. C. Montero-Conde, S. Ruiz-Llorente, J. M. Dominguez, J. A. Knauf, A. Viale, E. J. Sherman, M. Ryder, R. A. Ghossein, N. Rosen, J. A. Fagin, Relief of feedback inhibition of HER3 transcription by RAF and MEK inhibitors attenuates their antitumor effects in BRAF-mutant thyroid carcinomas. *Cancer discovery* 3, 520-533 (2013); published online EpubMay (10.1158/2159-8290.CD-12-0531).
25. K. Takezawa, V. Pirazzoli, M. E. Arcila, C. A. Nebhan, X. Song, E. de Stanchina, K. Ohashi, Y. Y. Janjigian, P. J. Spitzler, M. A. Melnick, G. J. Riely, M. G. Kris, V. A. Miller, M. Ladanyi, K. Politi, W. Pao, HER2 amplification: a potential mechanism of acquired resistance to EGFR inhibition in EGFR-mutant lung cancers that lack the second-site EGFRT790M mutation. *Cancer discovery* 2, 922-933 (2012); published online EpubOct (10.1158/2159-8290.CD-12-0108).
26. K. Shtiegman, B. S. Kochupurakkal, Y. Zwang, G. Pines, A. Starr, A. Vexler, A. Citri, M. Katz, S. Lavi, Y. Ben-Basat, S. Benjamin, S. Corso, J. Gan, R. B. Yosef, S. Giordano, Y. Yarden, Defective ubiquitinylation of EGFR mutants of lung cancer confers prolonged signaling. *Oncogene* 26, 6968-6978 (2007); published online EpubOct 25.
27. J. L. Pujol, R. Pirker, T. J. Lynch, C. A. Butts, R. Rosell, F. A. Shepherd, J. Vansteenkiste, K. J. O'Byrne, B. de Blas, J. Heighway, A. von Heydebreck, N. Thatcher, Meta-analysis of individual patient data from randomized trials of chemotherapy plus cetuximab as first-line treatment for advanced non-small cell lung cancer. *Lung Cancer* 83, 211-218 (2014); published online EpubFeb (10.1016/j.lungcan.2013.11.006).
28. J. C. Yang, V. Hirsh, M. Schuler, N. Yamamoto, K. J. O'Byrne, T. S. Mok, V. Zazulina, M. Shahidi, J. Lungershausen, D. Massey, M. Palmer, L. V. Sequist, Symptom control and quality of life in LUX-Lung 3: a phase III study of afatinib or cisplatin/pemetrexed in patients with advanced lung adenocarcinoma with EGFR mutations. *Journal of clinical oncology: official journal of the American Society of Clinical Oncology* 31, 3342-3350 (2013); published online EpubSep 20 (10.1200/JCO.2012.46.1764).
29. J. Baselga, J. Cortes, S. B. Kim, S. A. Im, R. Hegg, Y. H. Im, L. Roman, J. L. Pedrini, T. Pienkowski, A. Knott, E. Clark, M. C. Benyunes, G. Ross, S. M. Swain, Pertuzumab plus trastuzumab plus docetaxel for metastatic breast cancer. *The New England journal of medicine* 366, 109-119 (2012); published online EpubJan 12 (10.1056/NEJMoa1113216).

What is claimed is:

1. A method of treating a subject having lung cancer exhibiting a resistance to a tyrosine kinase inhibitor (TKI), wherein said TKI is directed to an ErbB family member and wherein cells of the cancer express said ErbB family member, the method comprising administering to the subject a therapeutically effective amount of antibodies comprising an anti-EGFR antibody, an anti-HER2 antibody and an anti-HER3 antibody, wherein:

(i) said anti-EGFR antibody comprises an antigen recognition domain having complementarity determining region (CDR) amino acid sequences as set forth in: SEQ ID NOs: 15 (CDR1), 16 (CDR2) and 17 (CDR3) (sequentially arranged from N to C on a light chain of said polypeptide) and 18 (CDR1), 19 (CDR2) and 20 (CDR3) (sequentially arranged from N to C on a heavy chain of said polypeptide) (Clone 565, CNCM-4262);

(ii) said anti-HER2 antibody comprises an antigen recognition domain having complementarity determining region (CDR) amino acid sequences as set forth in: SEQ ID NOs: 21 (CDR1), 22 (CDR2) and 23 (CDR3) (sequentially arranged from N to C on a light chain of said polypeptide) and 24 (CDR1), 25 (CDR2) and 26 (CDR3) (sequentially arranged from N to C on a heavy chain of said polypeptide) (Clone N12, CNCM-I-4112);

(iii) said anti-HER3 antibody comprises an antigen recognition domain having complementarity determining region (CDR) amino acid sequences as set forth in: SEQ ID NOs: 27 (CDR1), 28 (CDR2) and 29 (CDR3) (sequentially arranged from N to C on a light chain of said polypeptide) and 30 (CDR1), 31 (CDR2) and 32 (CDR3) (sequentially arranged from N to C on a heavy chain of said polypeptide) (Clone NG33);

(iv) said anti-EGFR antibody comprises an antigen recognition domain having complementarity determining region (CDR) amino acid sequences as set forth in: SEQ ID NOs: 15 (CDR1), 16 (CDR2) and 17 (CDR3) (sequentially arranged from N to C on a light chain of said polypeptide) and 18 (CDR1), 19 (CDR2) and 20 (CDR3) (sequentially arranged from N to C on a heavy chain of said polypeptide) (Clone 565, CNCM-4262) and said anti-HER2 antibody comprises an antigen recognition domain having complementarity determining region (CDR) amino acid sequences as set forth in: SEQ ID NOs: 21 (CDR1), 22 (CDR2) and 23 (CDR3) (sequentially arranged from N to C on a light chain of said polypeptide) and 24 (CDR1), 25 (CDR2) and 26 (CDR3) (sequentially arranged from N to C on a heavy chain of said polypeptide) (Clone N12, CNCM-I-4112);

(v) said anti-EGFR antibody comprises an antigen recognition domain having complementarity determining region (CDR) amino acid sequences as set forth in: SEQ ID NOs: 15 (CDR1), 16 (CDR2) and 17 (CDR3) (sequentially arranged from N to C on a light chain of said polypeptide) and 18 (CDR1), 19 (CDR2) and 20 (CDR3) (sequentially arranged from N to C on a heavy chain of said polypeptide) (Clone 565, CNCM-4262) and said anti-HER3 antibody comprises an antigen recognition domain having complementarity determining region (CDR) amino acid sequences as set forth in: SEQ ID NOs: 27 (CDR1), 28 (CDR2) and 29 (CDR3) (sequentially arranged from N to C on a light chain of said polypeptide) and 30 (CDR1), 31 (CDR2) and 32 (CDR3) (sequentially arranged from N to C on a heavy chain of said polypeptide) (Clone NG33);

(vi) said anti-HER2 antibody comprises an antigen recognition domain having complementarity determining region (CDR) amino acid sequences as set forth in: SEQ ID NOs: 21 (CDR1), 22 (CDR2) and 23 (CDR3) (sequentially arranged from N to C on a light chain of said polypeptide) and 24 (CDR1), 25 (CDR2) and 26 (CDR3) (sequentially arranged from N to C on a heavy chain of said polypeptide) (Clone N12, CNCM-I-4112); and said anti-HER3 antibody comprises an antigen recognition domain having complementarity determining region (CDR) amino acid sequences as set forth in: SEQ ID NOs: 27 (CDR1), 28 (CDR2) and 29 (CDR3) (sequentially arranged from N to C on a light chain of said polypeptide) and 30 (CDR1), 31 (CDR2) and 32 (CDR3) (sequentially arranged from N to C on a heavy chain of said polypeptide) (Clone NG33);

(vii) said anti-EGFR antibody comprises an antigen recognition domain having complementarity determining region (CDR) amino acid sequences as set forth in: SEQ ID NOs: 15 (CDR1), 16 (CDR2) and 17 (CDR3) (sequentially arranged from N to C on a light chain of said polypeptide) and 18 (CDR1), 19 (CDR2) and 20 (CDR3) (sequentially arranged from N to C on a heavy chain of said polypeptide) (Clone 565, CNCM-4262), said anti-HER2 antibody comprises an antigen recognition domain having complementarity determining region (CDR) amino acid sequences as set forth in: SEQ ID NOs: 21 (CDR1), 22 (CDR2) and 23 (CDR3) (sequentially arranged from N to C on a light chain of said polypeptide) and 24 (CDR1), 25 (CDR2) and 26 (CDR3) (sequentially arranged from N to C on a heavy chain of said polypeptide) (Clone N12, CNCM-I-4112); and said anti-HER3 antibody comprises an antigen recognition domain having complementarity determining region (CDR) amino acid sequences as set forth in: SEQ ID NOs: 27 (CDR1), 28 (CDR2) and 29 (CDR3) (sequentially arranged from N to C on a light chain of said polypeptide) and 30 (CDR1), 31 (CDR2) and 32 (CDR3) (sequentially arranged from N to C on a heavy chain of said polypeptide) (Clone NG33);

(viii) said anti-EGFR antibody comprises cetuximab; and said anti-HER3 antibody comprises an antigen recognition domain having complementarity determining region (CDR) amino acid sequences as set forth in: SEQ ID NOs: 27 (CDR1), 28 (CDR2) and 29 (CDR3) (sequentially arranged from N to C on a light chain of said polypeptide) and 30 (CDR1), 31 (CDR2) and 32 (CDR3) (sequentially arranged from N to C on a heavy chain of said polypeptide) (Clone NG33);

(ix) said anti-HER2 antibody comprises trastuzumab; and said anti-HER3 antibody comprises an antigen recognition domain having complementarity determining region (CDR) amino acid sequences as set forth in: SEQ ID NOs: 27 (CDR1), 28 (CDR2) and 29 (CDR3) (sequentially arranged from N to C on a light chain of said polypeptide) and 30 (CDR1), 31 (CDR2) and 32 (CDR3) (sequentially arranged from N to C on a heavy chain of said polypeptide) (Clone NG33); and/or (x) said anti-EGFR antibody comprises cetuximab, said anti-HER2 antibody comprises trastuzumab; and said anti-HER3 antibody comprises an antigen recognition domain having complementarity determining region (CDR) amino acid sequences as set forth in: SEQ ID NOs: 27 (CDR1), 28 (CDR2) and 29 (CDR3) (sequentially arranged from N to C on a light chain of said polypeptide) and 30 (CDR1), 31 (CDR2) and 32 (CDR3) (sequentially arranged from N to C on a heavy chain of said polypeptide) (Clone NG33), thereby treating the lung cancer exhibiting resistance to a TKI of an ErbB family member in the subject.

2. The method of claim 1, further comprising administering said TKI to said subject.

3. The method of claim 1, further comprising administering an additional TKI to said subject which is different from said TKI.

4. The method of claim 1, wherein said ErbB family member is EGFR.

5. The method of claim 1, wherein said TKI is selected from the group consisting of erlotinib, gefitinib and lapatinib.

6. The method of claim 1, wherein said lung cancer is a non-small cell lung cancer (NSCLC).

7. The method of claim 1, wherein said cells of said cancer express an ErbB receptor having a mutation in a kinase domain of said receptor.

8. The method of claim 7, wherein said mutation does not substantially affect a kinase activity of said ErhB as compared to said kinase activity of said ErbB devoid of said mutation.

9. The method of claim 7, wherein said ErbB is EGFR.

10. The method of claim 9, wherein said mutation comprises a substitution of Threonine to Methionine at position 790 (T790M) or a Cysteine to Serine at position 797 (C797S).

11. The method of claim 1, further comprising subjecting the subject to a therapy selected from the group consisting of a radiotherapy and a chemotherapy.

12. The method of claim 1, wherein said administering comprises multiple administrations.

13. The method of claim 12, wherein said multiple administrations comprise bi-weekly administrations.

14. The method of claim 1, wherein said antibodies are selected causing at least 50% reduction in tumor volume as compared to a control in a xenograft mouse model.

15. The method of claim 1, wherein said resistance is acquired resistance.

* * * * *

SEQUENCE LISTING

<160> NUMBER OF SEQ ID NOS: 36

<210> SEQ ID NO 1
<211> LENGTH: 120
<212> TYPE: PRT
<213> ORGANISM: Artificial Sequence
<220> FEATURE:
<223> OTHER INFORMATION: anti-EGFR 565 VH amino acid sequence

<400> SEQUENCE: 1

Gln Val Gln Leu Gln Gln Ser Gly Ala Glu Leu Val Lys Pro Gly Ala
1               5                   10                  15

Ser Val Lys Leu Ser Cys Lys Ala Ser Gly Tyr Thr Phe Thr Asn Tyr
            20                  25                  30

Trp Ile His Trp Val Lys Gln Arg Pro Gly Gln Gly Leu Glu Trp Ile
        35                  40                  45

Gly Glu Ile Gly Pro Ile Asn Gly Arg Ser Asn Tyr Ile Glu Lys Phe
    50                  55                  60

```
Lys Thr Lys Ala Thr Leu Thr Val Asp Lys Ser Ser Thr Thr Tyr
 65                  70                  75                  80

Leu His Leu Ser Ser Leu Thr Ser Glu Asp Ser Ala Val Tyr Tyr Cys
                 85                  90                  95

Ala Arg Glu Asp Asp Tyr Asp Gly Lys Ala Met Asp Tyr Trp Gly Gln
            100                 105                 110

Gly Thr Ser Val Thr Val Ser Ser
            115                 120

<210> SEQ ID NO 2
<211> LENGTH: 106
<212> TYPE: PRT
<213> ORGANISM: Artificial Sequence
<220> FEATURE:
<223> OTHER INFORMATION: EGFR 565  kappa amino acid sequence
<220> FEATURE:
<221> NAME/KEY: misc_feature
<222> LOCATION: (11)..(11)
<223> OTHER INFORMATION: Xaa can be any naturally occurring amino acid

<400> SEQUENCE: 2

Asp Ile Val Met Thr Gln Ser His Lys Phe Xaa Ser Thr Ser Val Gly
  1               5                  10                  15

Asp Arg Val Ser Ile Thr Cys Lys Ala Ser Gln Asn Val Gly Thr Ala
                 20                  25                  30

Val Ala Trp Tyr Gln Gln Lys Pro Gly Gln Ser Pro Lys Leu Leu Ile
             35                  40                  45

Tyr Trp Thr Ser Thr Arg His Thr Gly Val Pro Asp Arg Phe Thr Gly
 50                  55                  60

Thr Gly Ser Gly Thr Glu Phe Thr Leu Thr Ile Asn Asn Val Gln Ser
 65                  70                  75                  80

Glu Asp Leu Ala Asp Tyr Phe Cys Gln Gln Tyr Ser Gly Tyr Ser Phe
                 85                  90                  95

Gly Gly Gly Thr Lys Leu Glu Leu Lys Arg
            100                 105

<210> SEQ ID NO 3
<211> LENGTH: 117
<212> TYPE: PRT
<213> ORGANISM: Artificial Sequence
<220> FEATURE:
<223> OTHER INFORMATION: of anti-HER2 N12 VH amino acid sequence

<400> SEQUENCE: 3

Gln Val Gln Leu Gln Gln Ser Gly Ala Glu Leu Val Arg Pro Gly Asp
  1               5                  10                  15

Ser Val Asn Leu Ser Cys Lys Ala Ser Gly Tyr Thr Phe Thr Ser Tyr
                 20                  25                  30

Trp Met Tyr Trp Ile Lys Gln Arg Pro Asp Gln Gly Leu Glu Ser Ile
             35                  40                  45

Gly Asn Ile His Pro Asn Asn Gly Gly Thr Asn Tyr Ser Gly Lys Phe
 50                  55                  60

Lys Asn Lys Ala Ser Leu Thr Val Asp Lys Ser Ser Thr Thr Ala Tyr
 65                  70                  75                  80

Met Gln Leu Ser Ser Leu Thr Ser Glu Asp Ser Ala Val Tyr Phe Cys
                 85                  90                  95
```

```
Ala Arg Leu Thr Gly Ile Gly Met Asp Tyr Trp Gly Gln Gly Thr Ser
            100                 105                 110
Val Ile Val Ser Ser
        115

<210> SEQ ID NO 4
<211> LENGTH: 106
<212> TYPE: PRT
<213> ORGANISM: Artificial Sequence
<220> FEATURE:
<223> OTHER INFORMATION: anti-HER2 N12 Vkappa amino acid sequence

<400> SEQUENCE: 4

Asp Ile Val Met Thr Gln Ser His Lys Phe Met Ser Thr Ser Val Gly
1               5                   10                  15

Asp Arg Val Ser Ile Thr Cys Lys Ala Ser Gln Asn Val Gly Thr Ala
            20                  25                  30

Val Ala Trp Tyr Gln Gln Lys Pro Gly Gln Ser Pro Lys Leu Leu Ile
        35                  40                  45

Tyr Trp Thr Ser Thr Arg His Thr Gly Val Pro Asp Arg Phe Thr Gly
    50                  55                  60

Thr Gly Ser Gly Thr Glu Phe Thr Leu Thr Ile Asn Asn Val Gln Ser
65                  70                  75                  80

Glu Asp Leu Ala Asp Tyr Phe Cys Gln Gln Tyr Ser Gly Tyr Ser Phe
                85                  90                  95

Gly Gly Gly Thr Arg Leu Glu Ile Lys Leu
            100                 105

<210> SEQ ID NO 5
<211> LENGTH: 120
<212> TYPE: PRT
<213> ORGANISM: Artificial Sequence
<220> FEATURE:
<223> OTHER INFORMATION: anti-HER3 33 VH amino acid sequence

<400> SEQUENCE: 5

Asp Val Gln Leu Gln Glu Ser Gly Pro Gly Leu Val Lys Pro Ser Gln
1               5                   10                  15

Ser Leu Ser Leu Thr Cys Ser Val Thr Gly Tyr Ser Ile Thr Ser Gly
            20                  25                  30

Phe Tyr Trp Ser Trp Ile Arg Gln Phe Pro Gly Asn Lys Leu Glu Trp
        35                  40                  45

Met Gly Tyr Ile Ala Tyr Asp Gly Thr Ser Asn Tyr Asn Pro Ser Leu
    50                  55                  60

Lys Asn Arg Ile Ser Ile Thr Arg Asp Thr Ser Lys Asn Gln Phe Phe
65                  70                  75                  80

Leu Lys Leu Lys Ser Val Thr Asn Glu Asp Thr Pro Thr Tyr Tyr Cys
                85                  90                  95

Ala Arg Gly Gly Gly Tyr Tyr Gly Gln Leu Leu Asp Tyr Trp Gly Gln
            100                 105                 110

Gly Thr Ser Val Thr Val Ser Ser
        115                 120

<210> SEQ ID NO 6
<211> LENGTH: 107
<212> TYPE: PRT
<213> ORGANISM: Artificial Sequence
<220> FEATURE:
<223> OTHER INFORMATION: anti-HER3 33 Vkappa amino acid sequence
```

<400> SEQUENCE: 6

Asp Ala Arg Met Thr Gln Ser Pro Ser Leu Ser Ala Ser Leu Gly
1               5                  10                 15

Asp Arg Val Thr Ile Ser Cys Arg Ala Ser Gln Asp Ile Ser Asn Tyr
            20                  25                 30

Leu Asn Trp Tyr Gln Gln Lys Pro Asp Gly Thr Val Lys Val Leu Ile
        35                  40                  45

Tyr Asn Thr Ala Lys Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65              70                  75                  80

Glu Asp Phe Ala Thr Tyr Phe Cys Gln Gln Gly Lys Thr Leu Pro Trp
                85                  90                  95

Thr Phe Gly Gly Gly Thr Lys Leu Glu Leu Lys
            100                 105

<210> SEQ ID NO 7
<211> LENGTH: 25
<212> TYPE: DNA
<213> ORGANISM: Artificial Sequence
<220> FEATURE:
<223> OTHER INFORMATION: Single strand DNA oligonucleotide

<400> SEQUENCE: 7
gaggtggtac ttcaattgcg actca                                     25

<210> SEQ ID NO 8
<211> LENGTH: 20
<212> TYPE: DNA
<213> ORGANISM: Artificial Sequence
<220> FEATURE:
<223> OTHER INFORMATION: Single strand DNA oligonucleotide

<400> SEQUENCE: 8
agggaaggcg gacgcctgat                                           20

<210> SEQ ID NO 9
<211> LENGTH: 19
<212> TYPE: DNA
<213> ORGANISM: Artificial Sequence
<220> FEATURE:
<223> OTHER INFORMATION: Single strand DNA oligonucleotide

<400> SEQUENCE: 9
tgcagtggat tcgagaagc                                            19

<210> SEQ ID NO 10
<211> LENGTH: 20
<212> TYPE: DNA
<213> ORGANISM: Artificial Sequence
<220> FEATURE:
<223> OTHER INFORMATION: Single strand DNA oligonucleotide

<400> SEQUENCE: 10
agttcaacat gacgaagatg                                           20

<210> SEQ ID NO 11
<211> LENGTH: 18
<212> TYPE: DNA
<213> ORGANISM: Artificial Sequence
<220> FEATURE:
<223> OTHER INFORMATION: Single strand DNA oligonucleotide

<400> SEQUENCE: 11
acagttgcca tgtagacc                                                          18

<210> SEQ ID NO 12
<211> LENGTH: 18
<212> TYPE: DNA
<213> ORGANISM: Artificial Sequence
<220> FEATURE:
<223> OTHER INFORMATION: Single strand DNA oligonucleotide

<400> SEQUENCE: 12
tttttggttg agcacagg                                                          18

<210> SEQ ID NO 13
<211> LENGTH: 34
<212> TYPE: DNA
<213> ORGANISM: Artificial Sequence
<220> FEATURE:
<223> OTHER INFORMATION: Single strand DNA oligonucleotide

<400> SEQUENCE: 13
ggcgtcccgg cgctaggaag gcctgcgcag agag                                        34

<210> SEQ ID NO 14
<211> LENGTH: 36
<212> TYPE: DNA
<213> ORGANISM: Artificial Sequence
<220> FEATURE:
<223> OTHER INFORMATION: Single strand DNA oligonucleotide

<400> SEQUENCE: 14
ctctcttcgc gcaggccttc ctagcgccgg gacgcc                                      36

<210> SEQ ID NO 15
<211> LENGTH: 8
<212> TYPE: PRT
<213> ORGANISM: Artificial sequence
<220> FEATURE:
<223> OTHER INFORMATION: CDR peptide sequence

<400> SEQUENCE: 15

Gly Tyr Thr Phe Thr Asn Tyr Trp
1               5

<210> SEQ ID NO 16
<211> LENGTH: 8
<212> TYPE: PRT
<213> ORGANISM: Artificial sequence
<220> FEATURE:
<223> OTHER INFORMATION: CDR peptide sequence

<400> SEQUENCE: 16

Ile Gly Pro Ile Asn Gly Arg Ser
1               5

<210> SEQ ID NO 17
<211> LENGTH: 13
<212> TYPE: PRT
<213> ORGANISM: Artificial sequence
<220> FEATURE:
<223> OTHER INFORMATION: CDR peptide sequence

<400> SEQUENCE: 17

Ala Arg Glu Asp Asp Tyr Asp Gly Lys Ala Met Asp Tyr
1               5                   10

```
<210> SEQ ID NO 18
<211> LENGTH: 6
<212> TYPE: PRT
<213> ORGANISM: Artificial sequence
<220> FEATURE:
<223> OTHER INFORMATION: CDR peptide sequence

<400> SEQUENCE: 18

Gln Asn Val Gly Thr Ala
1               5

<210> SEQ ID NO 19
<211> LENGTH: 3
<212> TYPE: PRT
<213> ORGANISM: Artificial sequence
<220> FEATURE:
<223> OTHER INFORMATION: CDR peptide sequence

<400> SEQUENCE: 19

Trp Thr Ser
1

<210> SEQ ID NO 20
<211> LENGTH: 7
<212> TYPE: PRT
<213> ORGANISM: Artificial sequence
<220> FEATURE:
<223> OTHER INFORMATION: CDR peptide sequence

<400> SEQUENCE: 20

Gln Gln Tyr Ser Gly Tyr Ser
1               5

<210> SEQ ID NO 21
<211> LENGTH: 8
<212> TYPE: PRT
<213> ORGANISM: Artificial sequence
<220> FEATURE:
<223> OTHER INFORMATION: CDR peptide sequence

<400> SEQUENCE: 21

Gly Tyr Thr Phe Thr Ser Tyr Trp
1               5

<210> SEQ ID NO 22
<211> LENGTH: 8
<212> TYPE: PRT
<213> ORGANISM: Artificial sequence
<220> FEATURE:
<223> OTHER INFORMATION: CDR peptide sequence

<400> SEQUENCE: 22

Ile His Pro Asn Asn Gly Gly Thr
1               5

<210> SEQ ID NO 23
<211> LENGTH: 10
<212> TYPE: PRT
<213> ORGANISM: Artificial sequence
<220> FEATURE:
<223> OTHER INFORMATION: CDR peptide sequence

<400> SEQUENCE: 23

Ala Arg Leu Thr Gly Ile Gly Met Asp Tyr
1               5                   10
```

```
<210> SEQ ID NO 24
<211> LENGTH: 6
<212> TYPE: PRT
<213> ORGANISM: Artificial sequence
<220> FEATURE:
<223> OTHER INFORMATION: CDR peptide sequence

<400> SEQUENCE: 24

Gln Asn Val Gly Thr Ala
1               5

<210> SEQ ID NO 25
<211> LENGTH: 3
<212> TYPE: PRT
<213> ORGANISM: Artificial sequence
<220> FEATURE:
<223> OTHER INFORMATION: CDR peptide sequence

<400> SEQUENCE: 25

Trp Thr Ser
1

<210> SEQ ID NO 26
<211> LENGTH: 7
<212> TYPE: PRT
<213> ORGANISM: Artificial sequence
<220> FEATURE:
<223> OTHER INFORMATION: CDR peptide sequence

<400> SEQUENCE: 26

Gln Gln Tyr Ser Gly Tyr Ser
1               5

<210> SEQ ID NO 27
<211> LENGTH: 9
<212> TYPE: PRT
<213> ORGANISM: Artificial sequence
<220> FEATURE:
<223> OTHER INFORMATION: CDR peptide sequence

<400> SEQUENCE: 27

Gly Tyr Ser Ile Thr Ser Gly Phe Tyr
1               5

<210> SEQ ID NO 28
<211> LENGTH: 7
<212> TYPE: PRT
<213> ORGANISM: Artificial sequence
<220> FEATURE:
<223> OTHER INFORMATION: CDR peptide sequence

<400> SEQUENCE: 28

Ile Ala Tyr Asp Gly Thr Ser
1               5

<210> SEQ ID NO 29
<211> LENGTH: 13
<212> TYPE: PRT
<213> ORGANISM: Artificial sequence
<220> FEATURE:
<223> OTHER INFORMATION: CDR peptide sequence

<400> SEQUENCE: 29

Ala Arg Gly Gly Gly Tyr Tyr Gly Gln Leu Leu Asp Tyr
1               5                   10
```

-continued

```
<210> SEQ ID NO 30
<211> LENGTH: 6
<212> TYPE: PRT
<213> ORGANISM: Artificial sequence
<220> FEATURE:
<223> OTHER INFORMATION: CDR peptide sequence

<400> SEQUENCE: 30

Gln Asp Ile Ser Asn Tyr
1               5

<210> SEQ ID NO 31
<211> LENGTH: 3
<212> TYPE: PRT
<213> ORGANISM: Artificial sequence
<220> FEATURE:
<223> OTHER INFORMATION: CDR peptide sequence

<400> SEQUENCE: 31

Asn Thr Ala
1

<210> SEQ ID NO 32
<211> LENGTH: 9
<212> TYPE: PRT
<213> ORGANISM: Artificial sequence
<220> FEATURE:
<223> OTHER INFORMATION: CDR peptide sequence

<400> SEQUENCE: 32

Gln Gln Gly Lys Thr Leu Pro Trp Thr
1               5

<210> SEQ ID NO 33
<211> LENGTH: 16
<212> TYPE: DNA
<213> ORGANISM: Artificial Sequence
<220> FEATURE:
<223> OTHER INFORMATION: Single strand DNA oligonucleotide

<400> SEQUENCE: 33
gcctgctggg catctg                                                     16

<210> SEQ ID NO 34
<211> LENGTH: 23
<212> TYPE: DNA
<213> ORGANISM: Artificial Sequence
<220> FEATURE:
<223> OTHER INFORMATION: Single strand DNA oligonucleotide

<400> SEQUENCE: 34
tctttgtgtt cccggacata gtc                                             23

<210> SEQ ID NO 35
<211> LENGTH: 15
<212> TYPE: DNA
<213> ORGANISM: Artificial Sequence
<220> FEATURE:
<223> OTHER INFORMATION: Single strand DNA oligonucleotide
<220> FEATURE:
<221> NAME/KEY: misc_signal
<222> LOCATION: (1)..(1)
<223> OTHER INFORMATION: VIC labeled
<220> FEATURE:
<221> NAME/KEY: misc_signal
<222> LOCATION: (15)..(15)
<223> OTHER INFORMATION: 3' conjugated with MGB-NFQ
```

```
<400> SEQUENCE: 35
ttcggctgcc tcctg                                               15

<210> SEQ ID NO 36
<211> LENGTH: 13
<212> TYPE: DNA
<213> ORGANISM: Artificial Sequence
<220> FEATURE:
<223> OTHER INFORMATION: Single strand DNA oligonucleotide
<220> FEATURE:
<221> NAME/KEY: misc_feature
<222> LOCATION: (1)..(1)
<223> OTHER INFORMATION: FAM labeled
<220> FEATURE:
<221> NAME/KEY: misc_feature
<222> LOCATION: (13)..(13)
<223> OTHER INFORMATION: 3' conjugated with MGB-NFQ

<400> SEQUENCE: 36
ttcggcagcc tcc                                                 13
```